US008163754B2

(12) United States Patent
Fairhurst et al.

(10) Patent No.: US 8,163,754 B2
(45) Date of Patent: Apr. 24, 2012

(54) PURINE DERIVATIVES FOR USE AS ADENOSINE A-2A RECEPTOR AGONISTS

(75) Inventors: Robin Alec Fairhurst, Horsham (GB); Roger John Taylor, Horsham (GB); Harinder Pal Singh, Horsham (GB)

(73) Assignee: Novartis AG, Basel (CH)

( * ) Notice: Subject to any disclaimer, the term of this patent is extended or adjusted under 35 U.S.C. 154(b) by 340 days.

(21) Appl. No.: 11/576,607

(22) PCT Filed: Oct. 21, 2005

(86) PCT No.: PCT/EP2005/011344

§ 371 (c)(1), (2), (4) Date: Jan. 4, 2008

(87) PCT Pub. No.: WO2006/045552

PCT Pub. Date: May 4, 2006

(65) Prior Publication Data

US 2008/0200483 A1 Aug. 21, 2008

(30) Foreign Application Priority Data

Oct. 22, 2004 (GB) .................................. 0423551.1
Jul. 15, 2005 (GB) .................................. 0514619.6

(51) Int. Cl.

| | |
|---|---|
| *C07D 473/16* | (2006.01) |
| *C07D 473/40* | (2006.01) |
| *C07D 473/34* | (2006.01) |
| *A61K 31/52* | (2006.01) |
| *A61P 11/06* | (2006.01) |

(52) U.S. Cl. ........... 514/252.16; 514/263.2; 514/263.22; 514/263.23; 514/263.4; 544/277

(58) Field of Classification Search ........................ None
See application file for complete search history.

(56) References Cited

U.S. PATENT DOCUMENTS

| | | | | |
|---|---|---|---|---|
| 4,008,125 | A | 2/1977 | Kurozumi et al. | |
| 4,738,954 | A | 4/1988 | Hamilton et al. | |
| 4,873,360 | A | 10/1989 | Johnson et al. | |
| 4,954,504 | A | 9/1990 | Chen et al. | |
| 5,688,774 | A | 11/1997 | Jacobson et al. | |
| 6,307,054 | B1 | 10/2001 | Truesdale et al. | |
| 6,376,472 | B1 | 4/2002 | Myers et al. | |
| 6,403,567 | B1 | 6/2002 | Zablocki et al. | |
| 6,429,315 | B1 | 8/2002 | Sledeski et al. | |
| 6,492,348 | B1 | 12/2002 | Bays et al. | |
| 6,559,313 | B2 | 5/2003 | Myers et al. | |
| 6,677,316 | B2 | 1/2004 | Bays et al. | |
| 7,553,823 | B2 | 6/2009 | Zablocki et al. | |
| 7,737,126 | B2 | 6/2010 | Blatcher et al. | |
| 2003/0092668 | A1 | 5/2003 | Liang et al. | |
| 2003/0176390 | A1 | 9/2003 | Herling et al. | |
| 2004/0106572 | A1 | 6/2004 | Fishman et al. | |
| 2004/0162422 | A1* | 8/2004 | Hall et al. | 536/27.3 |
| 2005/0101551 | A1 | 5/2005 | Sevillano et al. | |
| 2005/0182018 | A1 | 8/2005 | Linden et al. | |
| 2006/0142237 | A1 | 6/2006 | Fishman et al. | |
| 2006/0189636 | A1* | 8/2006 | Critchley et al. | 514/263.22 |
| 2007/0099865 | A1 | 5/2007 | Fishman et al. | |
| 2007/0191293 | A1* | 8/2007 | Langston et al. | 514/43 |
| 2007/0232626 | A1 | 10/2007 | Jacobson et al. | |
| 2008/0027022 | A1 | 1/2008 | Linden et al. | |
| 2008/0051364 | A1 | 2/2008 | Fishman et al. | |
| 2008/0051404 | A1* | 2/2008 | Claiborne et al. | 514/245 |
| 2008/0207648 | A1* | 8/2008 | Fairhurst et al. | 514/263.22 |
| 2008/0214581 | A1 | 9/2008 | Allen et al. | |
| 2008/0242683 | A1 | 10/2008 | Fairhurst et al. | |
| 2008/0262001 | A1 | 10/2008 | Kranenburg et al. | |
| 2008/0300213 | A1 | 12/2008 | Fishman | |
| 2008/0312160 | A1 | 12/2008 | Guerrant et al. | |
| 2009/0012035 | A1 | 1/2009 | Jacobson et al. | |
| 2009/0054476 | A1 | 2/2009 | Goblyos et al. | |

(Continued)

FOREIGN PATENT DOCUMENTS

EP 0 267 878 A1 5/1988

(Continued)

OTHER PUBLICATIONS

Ghosh, Journal of Organic Chemistry (1995), 60(18), 5808-13.*
Hegde, Journal of Organic Chemistry (1998), 63(20), 7092-7094.*
Chemical Abstracts Index entry for Journal of Organic Chemistry (1998), 63(20), 7092-7094.*
Barnard, Antiviral Chemistry & Chemotherapy (2001), 12(4), 241-250.*
Cowart, J. Org. Chem. 1999, 64, 2240-2249.*
Yang, Bioorganic & Medicinal Chemistry 13 (2005) 877-882.*
Kerns, Edward et al, Drug-like Properties: Concepts, Structure Design and Methods: from ADME to Toxicity Optimization, (Elsevier, 2008) pp. 92-93.*
Goosen et al., Pharmaceutical Research vol. 19, No. 1, 13-19 (Jan. 2002).*

(Continued)

*Primary Examiner* — Mark Berch
(74) *Attorney, Agent, or Firm* — Paul D. Strain; Strain & Strain PLLC

(57) ABSTRACT

Compounds of formula I

I

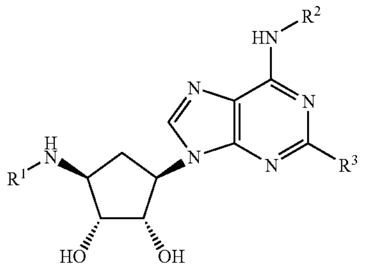

in free or salt form, wherein $R^1$, $R^2$ and $R^3$ have the meanings as indicated in the specification, are useful for treating conditions mediated by activation of the adenosine $A_{2A}$ receptor, especially inflammatory or obstructive airways diseases. Pharmaceutical compositions that contain the compounds and a process for preparing the compounds are also described.

6 Claims, No Drawings

U.S. PATENT DOCUMENTS

| | | | | |
|---|---|---|---|---|
| 2009/0081764 | A1 | 3/2009 | Pausch et al. | |
| 2009/0093633 | A1* | 4/2009 | Fairhurst et al. | 544/277 |
| 2009/0099214 | A1* | 4/2009 | Fairhurst et al. | 514/263.22 |
| 2009/0105476 | A1* | 4/2009 | Fairhurst et al. | 544/277 |
| 2009/0123510 | A1 | 5/2009 | Cronstein et al. | |
| 2009/0181920 | A1 | 7/2009 | Watkins et al. | |
| 2009/0181934 | A1* | 7/2009 | Fairhurst | 514/171 |
| 2009/0240045 | A1 | 9/2009 | Fairhurst et al. | |
| 2009/0281126 | A1* | 11/2009 | Fairhurst et al. | 514/263.2 |
| 2009/0281127 | A1* | 11/2009 | Fairhurst et al. | 514/263.4 |
| 2009/0325967 | A1 | 12/2009 | Fairhurst et al. | |
| 2010/0041918 | A1 | 2/2010 | Laumen | |
| 2010/0190784 | A1 | 7/2010 | Fairhurst et al. | |
| 2010/0197914 | A1 | 8/2010 | Fairhurst | |
| 2010/0240680 | A1 | 9/2010 | Fairhurst et al. | |
| 2010/0286126 | A1 | 11/2010 | Fairhurst et al. | |

FOREIGN PATENT DOCUMENTS

| | | | |
|---|---|---|---|
| JP | 63-219387 | | 9/1988 |
| WO | WO 92/05177 | A1 | 4/1992 |
| WO | WO 93/22328 | A1 | 11/1993 |
| WO | WO 98/50047 | A1 | 11/1998 |
| WO | WO 99/67263 | A1 | 12/1999 |
| WO | WO 99/67265 | A1 | 12/1999 |
| WO | WO 99/67266 | A1 | 12/1999 |
| WO | WO 00/23457 | A1 | 4/2000 |
| WO | WO 00/78774 | A2 | 12/2000 |
| WO | WO 00/78779 | A2 | 12/2000 |
| WO | WO 01/60835 | A1 | 8/2001 |
| WO | WO 02/22630 | A1 | 3/2002 |
| WO | WO 02/055085 | A2 | 7/2002 |
| WO | WO 02/070534 | A1 | 9/2002 |
| WO | WO 03/029264 | A2 | 4/2003 |
| WO | WO 03/086408 | A1 | 10/2003 |
| WO | WO 2005/063246 | A1 | 7/2005 |
| WO | WO 2005/084653 | A2 | 9/2005 |
| WO | WO 2005/107463 | A1 | 11/2005 |
| WO | WO 2005/116037 | A1 | 12/2005 |
| WO | WO 2006/011130 | A1 | 2/2006 |
| WO | WO 2006/045552 | A1 | 5/2006 |
| WO | WO 2006/074925 | A1 | 7/2006 |
| WO | WO 2006/097260 | A1 | 9/2006 |
| WO | WO 2007/121917 | A2 | 11/2007 |
| WO | WO 2007/121919 | A1 | 11/2007 |
| WO | WO 2007/121920 | A2 | 11/2007 |
| WO | WO 2007/121921 | A2 | 11/2007 |
| WO | WO 2007/121923 | A1 | 11/2007 |
| WO | WO 2007/121924 | A2 | 11/2007 |
| WO | WO 2007/147659 | A1 | 12/2007 |
| WO | WO 2008/006563 | A1 | 1/2008 |

OTHER PUBLICATIONS

Fourie, International Journal of Pharmaceutics vol. 279, Issues 1-2, Jul. 26, 2004, pp. 59-66.*

Edwards, J. Med. Chem. 39 (1996), pp. 1112-1124.*

Rautio, Eur. J. Pharm. Sci. 11:157-163 (2000).*

M. Yang et al., "Amino substituted derivatives of 5'-amino-5'-deoxy-5'-noraristeromycin", Bioroganic & Medicinal Chemistry, vol. 13, No. 3, pp. 877-882, (2005).

M. Cowart et al., "Synthesis of novel carboxyclic adenosine analogs as inhibitors of adenosine kinase", Journal of Organic Chemistry, vol. 64, No. 7, pp. 2240-2249, (1999).

Baraldi et al., "Recent improvements in the field of A3 adenosine receptor ligands", Expert Opinion on Therapeutic Patents, vol. 15, No. 11 (2005), pp. 1507-1519.

Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.

Curran et al., "The Preparation of Optically Active 2, Cyclopenten-1,4-Diol Derivatives from Furfuryl Alcohol", Tetrahedron, vol. 53, No. 6 (1997), pp. 1983-2004.

Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.

Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.

Kikugawa et al., "Platelet Aggregation Inhibitors. 6. 12-Thioadenosine Derivatives", Journal of Medicinal Chemistry, vol. 16, No. 12 (1973), pp. 1381-1388.

Marlene A Jacobsen, "Adenosine receptor agonists", Expert Opinion Therapeutic Targets, vol. 12, No. 4 (2002), pp. 489-501.

Marumoto et al., "Synthesis and Coronary Vasodilating Activity of 2-Substituted Adenosines", Chemical and Pharmaceutical Bulletin, vol. 23, No. 4 (1975), pp. 759-774.

Oriyama et al., "Catalytic Asymmetrization of CIS-2-Cyclopentene-1,4-Diol. Highly Efficient and Practical Synthesis . . . ", Heterocycles, vol. 52, No. 3 (2000), pp. 1055-1069.

Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.

Silverman J, Rheumatol, vol. 35, No. 4(2008), pp. 1-8.

Terashima et al., "Novel Use of Meso-Compound for the Preparation of Optically Active Compounds . . . ", Tetrahedron Letters, vol. 11 (1977), pp. 1001-1004.

Fairhurst, U.S. PTO Office Action, U.S. Appl. No. 11/722,835, Dec. 22, 2009, 37 pgs.

Fairhurst, U.S. PTO Office Action, U.S. Appl. No. 11/722,835, Jul. 16, 2010, 32 pgs.

Fairhurst, U.S. PTO Office Action, U.S. Appl. No. 12/296,714, Jan. 5, 2010, 4 pgs.

Fairhurst, U.S. PTO Office Action, U.S. Appl. No. 12/296,714, May 19, 2010, 63 pgs.

Fairhurst, U.S. PTO Office Action, U.S. Appl. No. 12/296,714, Dec. 23, 2009, 12 pgs.

Fairhurst, U.S. PTO Office Action, U.S. Appl. No. 12/296,714, Dec. 30, 2009, 10 pgs.

Fairhurst, U.S. PTO Office Action, U.S. Appl. No. 12/297,373, Dec. 22, 2009, 8 pgs.

Fairhurst, U.S. PTO Office Action, U.S. Appl. No. 12/297,373, Jul. 15, 2010, 8 pgs.

Fairhurst, U.S. PTO Office Action, U.S. Appl. No. 12/297,404, Dec. 30, 2009, 18 pgs.

Fairhurst, U.S. PTO Office Action, U.S. Appl. No. 12/297,404, Jul. 15, 2010, 38 pgs.

Fairhurst, U.S. PTO Office Action, U.S. Appl. No. 12/297,940, Jan. 22, 2010, 15 pgs.

Fairhurst, U.S. PTO Office Action, U.S. Appl. No. 12/297,007, Dec. 23, 2009, 11 pgs.

Fairhurst, U.S. PTO Office Action, U.S. Appl. No. 12/297,007, Jul. 15, 2010, 32 pgs.

International Search Report, PCT/EP2007/006156, Oct. 12, 2007, 3 pgs.

International Search Report, PCT/EP2007/059666, Jan. 18, 2008, 3 pgs.

Unpublished Pending U.S. Appl. No. 12/297,291, Fairhurst et al., filed Oct. 15, 2008.

Unpublished Pending U.S. Appl. No. 12/297,491, Fairhurst et al., filed Oct. 17, 2008.

Fairhurst, U.S. PTO Office Action, U.S. Appl. No. 12/297,727, Oct. 4, 2010, 13 pgs.

Fairhurst, U.S. PTO Office Action, U.S. Appl. No. 11/722,835, Jan. 3, 2011, 12 pgs.

Fairhurst, U.S. PTO Office Action, U.S. Appl. No. 12/296,714, Jan. 3, 2011, 16 pgs.

Fairhurst, U.S. PTO Office Action, U.S. Appl. No. 12/297,291, Dec. 1, 2010, 21 pgs.

Bressi et al., "Adenosine Analogues as Inhibitors of Trypanosoma brucei Phosphoglycerate Kinase: Elucidation of a Novel Binding Mode for a 2-Amino-N6-Substituted Adenosine", Journal of Medicinal Chemistry, vol. 43, No. 22 (2000), pp. 4135-4150.

Fairhurst, U.S. PTO Office Action, U.S. Appl. No. 12/296,714, Apr. 28, 2011, 7 pgs.

Fairhurst, U.S. PTO Office Action, U.S. Appl. No. 12/297,291, Mar. 21, 2011, 41 pgs.

Fairhurst, U.S. PTO Office Action, U.S. Appl. No. 12/297,491, Mar. 24, 2011, 20 pgs.

Fairhurst, U.S. PTO Office Action, U.S. Appl. No. 12/308,637, Feb. 24, 2011, 23 pgs.

Fairhurst, U.S. PTO Office Action, U.S. Appl. No. 12/310,254, Mar. 24, 2011, 18 pgs.
Fairhurst, U.S. PTO Office Action, U.S. Appl. No. 12/679,663, Feb. 28, 2011, 21 pgs.
Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.
Wanner et al., "Synthesis and properties of 2-nitrosoadenosine", J. Chem. Soc., Perkin Trans., vol. 1 (2001), pp. 1908-1915.
Fairhurst, U.S. PTO Notice of Allowance, U.S. Appl. No. 11/722,835, May 27, 2011, 7 pgs.
Fairhurst, U.S. Notice of Allowance, U.S. Appl. No. 12/297,291, Jul. 14, 2011, 9 pgs.
Fairhurst, U.S. PTO Restriction Requirement, U.S. Appl. No. 12/247,764, Jul. 15, 2011, 14 pgs.
International Search Report, PCT/EP2008/063869, Jul. 21, 2009, 7 pgs.
Laumen, U.S. PTO Office Action, U.S. Appl. No. 12/312,311, Aug. 9, 2011, 20 pgs.
Siddiqi et al., "Enantiospecific Synthesis of the Fluoro and Epimeric Derivatives of 5'Noraristeromycin", J. Chem. Soc., Chem. Commun., 1993, pp. 708-709.
Unpublished pending U.S. Appl. No. 13/218,865, Robin Alec Fairhurst et al., filed Aug. 26, 2011.
Unpublished pending U.S. Appl. No. 13/218,887, Robin Alec Fairhurst et al., filed Aug. 26, 2011.
Fairhurst, U.S. PTO Notice of Allowance, U.S. Appl. No. 11/722,835, Oct. 21, 2011, 10 pgs.
Fairhurst, U.S. PTO Notice of Allowance, U.S. Appl. No. 12/308,637, Sep. 26, 2011, 13 pgs.
Fairhurst, U.S. PTO Office Action, U.S. Appl. No. 12/297,491, Oct. 12, 2011, 11 pgs.
Fairhurst, U.S. PTO Office Action, U.S. Appl. No. 12/310,254, Oct. 12, 2011, 11 pgs.
Fairhurst, U.S. PTO Office Action, U.S. Appl. No. 12/247,764, Oct. 26, 2011, 17 pgs.
Fairhurst, U.S. PTO Notice of Allowance, U.S. Appl. No. 12/297,491, Feb. 1, 2012, 7 pgs.
Fairhurst, U.S. PTO Notice of Allowance, U.S. Appl. No. 12/310,254, Feb. 2, 2012, 7 pgs.
Fairhurst, U.S. PTO Office Action, U.S. Appl. No. 13/218,865, Jan. 27, 2012, 21 pgs.
Fairhurst, U.S. PTO Office Action, U.S. Appl. No. 13/218,887, Feb. 1, 2012, 21 pgs.
Fairhurst, U.S. PTO Advisory Action, U.S. Appl. No. 12/297,491, Jan. 18, 2012, 15 pgs.
Fairhurst, U.S. PTO Advisory Action, U.S. Appl. No. 12/310,254, Jan. 18, 2012, 10 pgs.

* cited by examiner

PURINE DERIVATIVES FOR USE AS ADENOSINE A-2A RECEPTOR AGONISTS

This invention relates to organic compounds, their preparation and use as pharmaceuticals.

In one aspect, the present invention provides compounds of formula I

I

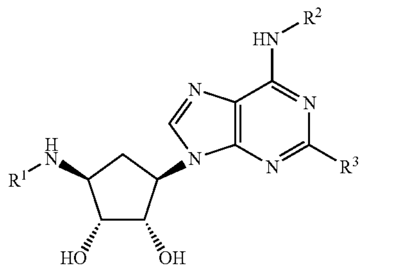

in free or salt form, wherein $R^1$ is hydrogen, $C_1$-$C_8$-alkylcarbonyl, $C_3$-$C_8$-cycloalkylcarbonyl, —$SO_2$—$C_1$-$C_8$-alkyl, $C_7$-$C_{14}$-aralkylcarbonyl or —C(═O)—C(═O)—NH—$C_1$-$C_8$-alkyl optionally substituted by $R^4$;

$R^2$ is hydrogen or $C_1$-$C_8$-alkyl optionally substituted by $C_6$-$C_{10}$-aryl;

$R^3$ is hydrogen, halo, $C_2$-$C_8$-alkenyl or $C_2$-$C_8$-alkynyl, or $R^3$ is amino optionally substituted by $C_3$-$C_8$-cycloalkyl optionally substituted by amino, or $R^3$ is $C_1$-$C_8$-alkylamino optionally substituted by hydroxy, $C_6$-$C_{10}$-aryl or by $R^5$, or $R^3$ is $R^6$ optionally substituted by amino or —NH—C(═O)—NH—$R^7$, or $R^3$ is —NH—$R^6$ optionally substituted —NH—C(═O)—NH—$R^7$, or $R^3$ is $C_1$-$C_8$-alkylaminocarbonyl or $C_3$-$C_8$-cycloalkylamino-carbonyl optionally substituted by amino, $C_1$-$C_8$-alkylamino, di($C_1$-$C_8$-alkyl)amino or —NH—C(═O)—NH—$R^8$;

$R^4$, $R^5$ and $R^6$ are independently a 5- or 6-membered heterocyclic ring containing at least one ring heteroatom selected from the group consisting of nitrogen, oxygen and sulphur, said 5- or 6-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl or $C_1$-$C_8$-alkoxy optionally substituted by aminocarbonyl; and $R^7$ and $R^8$ are independently a 5- or 6-membered heterocyclic ring containing at least one ring heteroatom selected from the group consisting of nitrogen, oxygen and sulphur, said 5- or 6-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulphur, said ring also being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl.

Terms used in the specification have the following meanings:

"Optionally substituted" means the group referred to can be substituted at one or more positions, preferably one or two positions, by any one or any combination of the radicals listed thereafter.

"Halo" or "halogen" as used herein may be fluorine, chlorine, bromine or iodine. Preferably halo is chlorine. When $R^3$ is halo it is preferably chloro. When $R^3$ is $R^6$ substituted by —NH—C(═O)—NH—$R^7$, where $R^7$ is a 5- or 6-membered heterocyclic ring containing at least one ring heteroatom selected from the group consisting of nitrogen, oxygen and sulphur substituted by halo, that heterocyclic ring is substituted at two positions by chloro.

"$C_1$-$C_8$-alkyl" as used herein denotes straight chain or branched alkyl having 1 to 8 carbon atoms. Preferably $C_1$-$C_8$-alkyl is $C_1$-$C_6$-alkyl. When $R^2$ is $C_1$-$C_8$-alkyl optionally substituted by $C_6$-$C_{10}$-aryl, $R^2$ is preferably either unsubstituted $C_1$-$C_6$-alkyl, especially pentyl or hexyl, more especially —$CH(C_2H_5)_2$ or —$CH_2CH_2C(CH_3)_3$, or $R^2$ is $C_1$-$C_8$-alkyl substituted by $C_6$-$C_{10}$-aryl, especially $C_2$-$C_5$-alkyl (more especially pentyl) substituted at one position by naphthyl or at two positions by phenyl.

"$C_2$-$C_8$-alkenyl" as used herein denotes straight chairs or branched hydrocarbon chains that contain 2 to 8 carbon atoms and one or more carbon-carbon double bonds. Preferably $C_2$-$C_8$-alkenyl is $C_2$-$C_4$-alkenyl".

"$C_2$-$C_8$-alkynyl" as used herein denotes straight chain or branched hydrocarbon chains that contain 2 to 8 carbon atoms and one or more carbon-carbon triple bonds and optionally one or more carbon-carbon double bonds. Preferably $C_2$-$C_8$-alkynyl is $C_2$-$C_6$-alkynyl. When $R^3$ is $C_2$-$C_8$-alkynyl it is preferably $C_2$-$C_6$-alkynyl, especially hexynyl, more especially —C≡C—$C_4H_9$.

"$C_1$-$C_8$-alkoxy" as used herein denotes straight chain or branched alkoxy having 1 to 8 carbon atoms. Preferably $C_1$-$C_8$-alkoxy is $C_1$-$C_4$-alkoxy.

"$C_3$-$C_8$-cycloalkyl" as used herein denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably $C_3$-$C_8$-cycloalkyl" is $C_3$-$C_6$-cycloalkyl. When $R^3$ is amino substituted by $C_3$-$C_8$-cycloalkyl, $C_3$-$C_8$-cycloalkyl is preferably $C_3$-$C_6$-cycloalkyl, more especially cyclohexyl.

"$C_1$-$C_8$-alkylamino" and "di($C_1$-$C_9$-alkyl)amino" as used herein denote amino substituted respectively by one or two $C_1$-$C_8$-alkyl groups as hereinbefore defined, which may be the same or different. Preferably $C_1$-$C_8$-alkylamino and di($C_1$-$C_8$-alkyl)amino are respectively $C_1$-$C_4$-alkylamino and di($C_1$-$C_4$-alkyl)amino. When $R^3$ is optionally substituted by $C_1$-$C_8$-alkylamino, $C_1$-$C_8$-alkylamino is preferably $C_1$-$C_4$-alkylamino, especially ethylamino or propylamino.

"$C_1$-$C_8$-alkylcarbonyl" and "$C_1$-$C_8$-alkoxycarbonyl" as used herein denote $C_1$-$C_8$-allyl or $C_1$-$C_8$-alkoxy respectively as hereinbefore defined attached by a carbon atom to a carbonyl group. Preferably $C_1$-$C_8$-alkylcarbonyl and $C_1$-$C_8$-alkoxycarbonyl are $C_1$-$C_4$-alkylcarbonyl and $C_1$-$C_4$-alkoxycarbonyl respectively.

"$C_3$-$C_8$-cycloalkylcarbonyl" as used herein denotes $C_3$-$C_8$-cycloalkyl as hereinbefore defined attached by a carbon atom to a carbonyl group. Preferably $C_3$-$C_8$-cycloalkylcarbonyl is $C_3$-$C_8$-cycloalkylcarbonyl. When $R^1$ is $C_3$-$C_8$-cycloalkylcarbonyl, it is preferably $C_3$-$C_8$-cycloalkylcarbonyl, especially cyclopropylcarbonyl or cyclobutylcarbonyl.

"$C_3$-$C_8$-cycloalkylamino" as used herein denotes $C_3$-$C_8$-cycloalkyl as hereinbefore defined attached by a carbon atom to the nitrogen atom of an amino group. Preferably $C_3$-$C_8$-cycloalkylamino is $C_3$-$C_8$-cycloalkylamino.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is phenyl or naphthyl. When $R^2$ is $C_1$-$C_8$-alkyl substituted by $C_6$-$C_{10}$-aryl, $C_6$-$C_{10}$-aryl is preferably phenyl or naphthyl.

"$C_7$-$C_{14}$-aralkyl" as used herein denotes alkyl, for example $C_1$-$C_4$-alkyl as hereinbefore defined, substituted by $C_6$-$C_{10}$-aryl as hereinbefore defined. Preferably $C_7$-$C_{14}$-aralkyl is $C_7$-$C_{10}$-aralkyl such as phenyl-$C_1$-$C_4$-alkyl, especially benzyl.

"$C_1$-$C_8$-alkylaminocarbonyl" and "$C_3$-$C_8$-cycloalkylaminocarbonyl" as used herein denote $C_1$-$C_8$-alkylamino and $C_3$-$C_8$-cycloalkylamino respectively as hereinbefore defined attached by a carbon atom to a carbonyl group. Preferably $C_1$-$C_8$-alkylaminocarbonyl and $C_3$-$C_8$-cycloalkyl-aminocarbonyl are $C_1$-$C_4$-alkylaminocarbonyl and $C_3$-$C_8$-cycloalkylaminocarbonyl respectively. When $R^3$ is $C_1$-$C_8$-alkylaminocarbonyl it is preferably $C_1$-$C_3$-alkylaminocarbonyl, especially propylaminocarbonyl.

"$C_6$-$C_{10}$-arylcarbonyl" and "$C_7$-$C_{14}$-arylkylcarbonyl" as used herein denote $C_6$-$C_{10}$-aryl and $C_7$-$C_{14}$-aryalkyl respectively as hereinbefore defined attached by a carbon atom to a carbonyl group. Preferably $C_6$-$C_{10}$-arylcarbonyl and $C_7$-$C_{14}$-aralkylcarbonyl are $C_6$-$C_8$-arylcarbonyl and $C_7$-$C_{10}$-aralkylcarbonyl respectively. When $R^1$ is $C_7$-$C_{14}$-aralkylcarbonyl it is preferably $C_7$-$C_{10}$-aralkylcarbonyl, especially benzylcarbonyl i.e. phenylacetamido.

"5- or 6-membered heterocyclic ring containing at least one ring heteroatom selected from the group consisting of nitrogen, oxygen and sulphur" as used herein may be, for example, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole. Preferred heterocyclic rings include piperazine, pyrrolidine, morpholino, imidazole, isotriazole, pyrazole, tetrazole, thiazole, thiadiazole, pyridine, piperidine, pyrazine, furan, oxazole, isoxazole, oxadiazole and azetidine. The 5- or 6-membered heterocyclic ring can be unsubstituted or it can be substituted at one or more positions, preferably one or two positions, by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl or $C_1$-$C_8$-alkoxy optionally substituted at one or more positions, preferably one or two positions, by aminocarbonyl. Especially preferred substituents include methyl, ethyl, d propyl) and amino. When $R^3$ is $C_1$-$C_8$-alkylamino optionally substituted by $R^5$, $R^5$ is preferably unsubstituted imidazolyl, unsubstituted piperidinyl, or imidazolyl substituted at one position by $C_1$-$C_3$-alkyl. When $R^3$ is $R^6$ optionally substituted by —NH—C(═O)—NH—$R^7$, $R^6$ is preferably pyrrolidinyl, piperidinyl or piperazinyl and, where relevant, $R^7$ is preferably unsubstituted thiophenyl, unsubstituted pyridinyl, unsubstituted pyrrolidinyl, pyridinyl disubstituted by chloro, piperazinyl substituted at one position by methyl, piperidinyl substituted at one position by pyridinyl, or piperidinyl substituted at one position by pyridinyl. When $R^3$ is —NH—$R^6$ optionally substituted —NH—C(═O)—NH—$R^7$, $R^6$ is preferably unsubstituted pyrrolidinyl or $R^6$ is pyrrolidinyl substituted at one position by —NH—C(═O)—NH—$R^7$ where $R^7$ is unsubstituted pyridinyl. When $R^3$ is $C_1$-$C_8$-alkylaminocarbonyl substituted by —NH—C(═O)—NH—$R^8$, $R^8$ is preferably unsubstituted piperidinyl, piperidinyl substituted at one position by methylsulfonyl, piperidinyl substituted at one position by pyridinyl, or pyrrolidinyl substituted at one position by pyridinyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of formula I in free or salt form include those where $R^1$ is $C_1$-$C_8$-alkylcarbonyl, $C_3$-$C_8$-cycloalkylcarbonyl, —$SO_2$—$C_1$-$C_8$-alkyl, $C_7$-$C_{14}$-aralkylcarbonyl or —C(═O)—C(═O)—NH—$C_1$-$C_8$-alkyl optionally substituted by $R^4$;

$R^2$ is hydrogen or $C_1$-$C_8$-alkyl optionally substituted by $C_6$-$C_{10}$-aryl;

$R^3$ is halo or $C_2$-$C_8$-alkynyl, or $R^3$ is amino optionally substituted by $C_3$-$C_8$-cycloalkyl optionally substituted by amino, or $R^3$ is $C_1$-$C_8$-alkylamino optionally substituted by hydroxy, $C_6$-$C_{10}$-aryl or by $R^5$, or $R^3$ is $R^6$ optionally substituted by amino or —NH—C(═O)—NH—$R^7$, or $R^3$ is —NH—$R^6$ optionally substituted —NH—C(═O)—NH—$R^7$, or $R^3$ is $C_1$-$C_8$-alkylaminocarbonyl optionally substituted by —NH—C(═O)—NH—$R^8$;

$R^4$, $R^5$ and $R^6$ are independently a 5- or 6-membered heterocyclic ring containing at least one ring heteroatom selected from the group consisting of nitrogen, oxygen and sulphur, said 5- or 6-membered heterocyclic ring being optionally substituted by $C_1$-$C_8$-alkyl; and $R^7$ and $R^8$ are independently a 5- or 6-membered heterocyclic ring containing at least one ring heteroatom selected from the group consisting of nitrogen, oxygen and sulphur, said 5- or 6-membered heterocyclic ring being optionally substituted by halo, $C_1$-$C_8$-alkyl, $C_1$-$C_8$-alkyl-sulfonyl, or a 5- or 6-membered heterocyclic ring containing at least one ring heteroatom selected from the group consisting of nitrogen, oxygen and sulphur.

Especially preferred compounds of formula I in free or salt form include those where $R^1$ is $C_1$-$C_4$-alkylcarbonyl, $C_3$-$C_8$-cycloalkylcarbonyl, —$SO_2$—$C_1$-$C_4$-alkyl, $C_7$-$C_{10}$-aralkylcarbonyl or —C(═O)—C(═O)—NH—$C_1$-$C_4$-alkyl optionally substituted at one position by $R^4$;

$R^2$ is hydrogen, unsubstituted $C_1$-$C_6$-alkyl or $C_1$-$C_8$-alkyl substituted at one position by $C_6$-$C_{10}$-aryl;

$R^3$ is halo or $C_2$-$C_6$-alkynyl, or $R^3$ is amino optionally substituted at one position by $C_3$-$C_6$-cycloalkyl optionally substituted at one position by amino, or $R^3$ is $C_1$-$C_4$-alkylamino substituted at one or two positions by hydroxy, phenyl or by $R^5$, or $R^3$ is $R^6$ optionally substituted at one position by amino or —NH—C(═O)—NH—$R^7$, or $R^3$ is —NH—$R^6$ optionally substituted at one position by —NH—C(═O)—NH—$R^7$, or $R^3$ is $C_1$-$C_4$-alkylaminocarbonyl substituted at one position by —NH—C(═O)—NH—$R^8$;

$R^4$, $R^5$ and $R^6$ are independently a 5- or 6-membered heterocyclic ring containing at least one ring heteroatom selected from the group consisting of nitrogen, oxygen and sulphur, said 5- or 6-membered heterocyclic ring being optionally substituted at one position by $C_1$-$C_4$-alkyl; and $R^7$ and $R^8$ are independently a 5- or 6-membered heterocyclic ring containing at least one ring heteroatom selected from the group consisting of nitrogen, oxygen and sulphur, said 5- or 6-membered heterocyclic ring being optionally substituted at one or two positions by halo, $C_1$-$C_4$-alkyl, $C_1$-$C_4$-alkylsulfonyl, or a 5- or 6-membered N-heterocyclic ring.

In a second aspect, the present invention provides compounds of formula I, in which $R^1$ is hydrogen, $C_1$-$C_8$-alkylcarbonyl, $C_3$-$C_8$-cycloalkylcarbonyl, —$SO_2$—$C_1$-$C_8$-alkyl, $C_7$-$C_{14}$-aralkylcarbonyl or —C(═O)—C(═O)—NH—$C_1$-$C_8$-alkyl optionally substituted by $R^4$;

$R^2$ is hydrogen or $C_1$-$C_8$-alkyl optionally substituted by $C_6$-$C_{10}$-aryl;

$R^3$ is hydrogen, halo, $C_2$-$C_8$-alkenyl or $C_2$-$C_9$-alkynyl, or $R^3$ is amino optionally substituted by $C_3$-$C_8$-cycloalkyl optionally substituted by amino, or $R^3$ is $C_1$-$C_8$-alkylamino optionally substituted by hydroxy, $C_6$-$C_{10}$-aryl or by $R^5$, or $R^3$ is $R^6$ optionally substituted by amino or —NH—C(═O)—NH—$R^7$, or $R^3$ is $C_1$-$C_8$-alkylaminocarbonyl or $C_3$-$C_8$-cyclo alkylamino-carbonyl optionally substituted by amino, $C_1$-$C_8$-alkylamino, di($C_1$-$C_8$-alkyl)amino or —NH—C(═O)—NH—$R^8$;

$R^4$, $R^5$ and $R^6$ are independently a 5- or 6-membered heterocyclic ring containing at least one ring heteroatom selected from the group consisting of nitrogen, oxygen and sulphur; and $R^7$ and $R^8$ are independently a S— or 6-membered heterocyclic ring containing at least one ring heteroatom selected from the group consisting of nitrogen, oxygen and sulphur, said 5- or 6-membered heterocyclic ring being optionally substituted by a 5- or 6-membered heterocyclic ring containing at least one ring heteroatom selected from the group consisting of nitrogen, oxygen and sulphur.

Preferred compounds of formula I in free or salt form include those where $R^1$ is $C_1$-$C_8$-alkylcarbonyl, $C_3$-$C_8$-cycloalkylcarbonyl, —$SO_2$—$C_1$-$C_8$-alkyl, $C_7$-$C_{14}$-aralkylcarbonyl or —C(═O)—C(═O)—NH—$C_1$-$C_8$-alkyl optionally substituted by $R^4$;

$R^2$ is hydrogen or $C_1$-$C_8$-alkyl optionally substituted by $C_6$-$C_{10}$-aryl;

$R^3$ is halo or $C_2$-$C_8$-alkynyl, or $R^3$ is amino optionally substituted by $C_3$-$C_8$-cycloalkyl optionally substituted by amino, or $R^3$ is $C_1$-$C_8$-alkylamino optionally substituted by hydroxy, $C_6$-$C_{10}$-aryl or by $R^5$—, or $R^3$ is $R^6$ optionally substituted by amino or —NH—C(═O)—NH—$R^7$, or $R^3$ is —NH—$R^6$ optionally substituted —NH—C(═O)—NH—$R^7$, or $R^3$ is $C_1$-$C_8$-alkylaminocarbonyl optionally substituted by —NH—C(═O)—NH—$R^8$;

$R^4$, $R^5$, and $R^6$ are independently a 5- or 6-membered heterocyclic ring containing at least one ring heteroatom selected from the group consisting of nitrogen, oxygen and sulphur; and $R^7$ and $R^8$ are independently a 5- or 6-membered heterocyclic ring containing at least one ring heteroatom selected from the group consisting of nitrogen, oxygen and sulphur, said 5- or 6-membered heterocyclic ring being optionally substituted by a 5- or 6-membered heterocyclic ring containing at least one ring heteroatom selected from the group consisting of nitrogen, oxygen and sulphur.

Especially preferred compounds of formula I in free or salt form include those where $R^1$ is $C_1$-$C_4$-alkylcarbonyl, $C_3$-$C_6$-cycloalkylcarbonyl, —$SO_2$—$C_1$-$C_4$-alkyl, $C_7$-$C_{10}$-aralkylcarbonyl or —C(═O)—C(═O)—NH—$C_1$-$C_4$-alkyl optionally substituted at one position by $R^4$;

$R^2$ is hydrogen or $C_1$-$C_6$-alkyl optionally substituted by $C_6$-$C_{10}$-aryl;

$R^3$ is halo or $C_2$-$C_8$-alkynyl, or $R^3$ is amino optionally substituted by $C_3$-$C_8$-cycloalkyl optionally substituted by amino, or $R^3$ is $C_1$-$C_4$-alkylamino optionally substituted by hydroxy, $C_6$-$C_8$-aryl or by $R^5$, or $R^3$ is $R^6$ optionally substituted by amino or —NH—C(═O)—NH—$R^7$, or $R^3$ is —NH—$R^6$ optionally substituted —NH—C(═O)—NH—$R^7$, or $R^3$ is $C_1$-$C_4$-alkylaminocarbonyl optionally substituted by —NH—C(═O)—NH—$R^8$;

$R^4$, $R^5$, and $R^6$ are independently a 5- or 6-membered heterocyclic ring containing at least one ring heteroatom selected from the group consisting of nitrogen, oxygen and sulphur; and $R^7$ and $R^8$ are independently a 5- or 6-membered heterocyclic ring containing at least one ring heteroatom selected from the group consisting of nitrogen, oxygen and sulphur, said 5- or 6-membered heterocyclic ring being optionally substituted by a 5- or 6-membered heterocyclic ring containing at least one ring heteroatom selected from the group consisting of nitrogen, oxygen and sulphur.

Especially preferred specific compounds of formula I are those described hereinafter in the Examples.

The compounds represented by formula I are capable of forming acid addition salts, particularly pharmaceutically acceptable acid addition salts. Pharmaceutically acceptable acid addition salts of the compound of formula Ia include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid, para-biphenyl benzoic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, cinnamic acids such as 3-(2-naphthalenyl)propenoic acid, para-methoxy cinnamic acid or para-methyl cinnamic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula Ia by known salt-forming procedures.

In those compounds where there is an asymmetric carbon atom the compounds exist in individual optically active isomeric forms or as mixtures thereof, e.g. as diastereomeric mixtures. The present invention embraces both individual optically active R and S isomers as well as mixtures thereof.

The invention provides, in another aspect, a method of preparing a compound of formula Ia in free or salt form which comprises (i) (A) for the preparation of compounds of formula I, reacting a compound of formula II

II

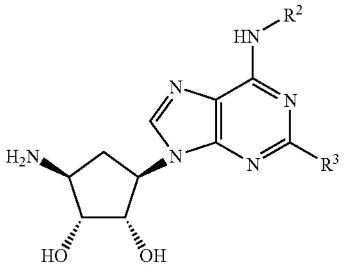

wherein $R^2$ and $R^3$ are as hereinbefore defined, with a compound of formula III $R^1—X^a$ III or a formula IIIa IIIa

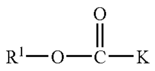

wherein $R^1$ is hydrogen, $C_1$-$C_8$-alkylcarbonyl, $C_3$-$C_8$-cycloalkylcarbonyl or $C_7$-$C_{14}$-aralkylcarbonyl, $X^a$ is a leaving group and K is hydrogen, $C_1$-$C_8$-alkyl or $C_1$-$C_8$-alkoxy, in the presence of a base;

(B) for the preparation of compounds of formula I where $R^3$ is amino substituted by $C_3$-$C_8$-cycloalkyl optionally substituted by amino or $R^3$ is $C_1$-$C_8$-alkylamino optionally substituted by hydroxy, $C_6$-$C_{10}$-aryl or by $R^5$, or $R^3$ is $R^6$ optionally substituted by amino or —NH—C(═O)—NH—$R^7$, reacting a compound of formula IV

IV

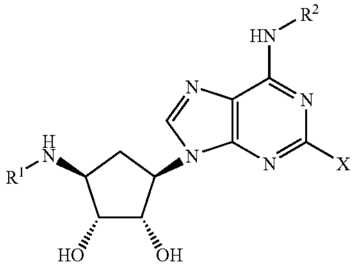

wherein $R^1$ and $R^2$ are as hereinbefore defined and X is halo, with a compound of formula Va or formula Vb $H_2N—R^{3a}$ Va Vb

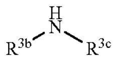

wherein $R^{3a}$ is $C_3$-$C_8$-cycloalkyl optionally substituted by amino or $R^3$ is $C_1$-$C_8$-alkyl optionally substituted by hydroxy, $C_1$-$C_{10}$-aryl or by $R^5$, where $R^5$ is as hereinbefore defined, and $R^{3b}$ and $R^{3c}$ together form a 5- or 6-membered heterocyclic ring that contains one or more nitrogen atoms and is optionally substituted amino or —NH—C(═O)—NH—$R^7$, where $R^7$ is as hereinbefore defined;

(C) for the preparation of compounds of formula I, reacting a compound of formula VI

VI

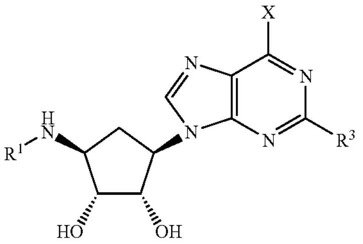

wherein $R^1$ and $R^3$ are as hereinbefore defined and X is halo, with a compound of formula VII $H_2N—R^2$ VII wherein $R^2$ is as hereinbefore defined, in the presence of a base;

(D) for the preparation of compounds of formula I, deprotecting a compound of formula VIII

VIII

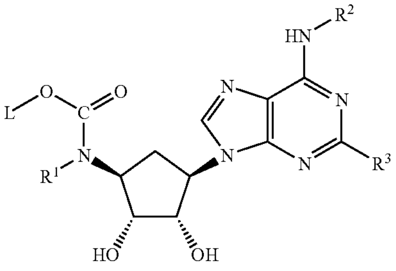

wherein $R^1$, $R^2$ and $R^3$ are as hereinbefore defined and L is $C_1$-$C_8$-alkyl;

(E) for the preparation of compounds of formula I wherein $R^3$ is $C_1$-$C_8$-alkylamino-carbonyl or $C_3$-$C_8$-cycloalkylaminocarbonyl substituted by —NH—C(═O)—NH—$R^8$, where $R^8$ is as hereinbefore defined, reacting a compound of formula IX

IX

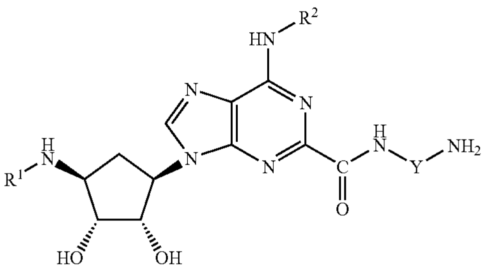

wherein $R^1$ and $R^2$ are as hereinbefore defined and Y is $C_1$-$C_8$-alkyl or $C_3$-$C_8$-cycloalkyl in the presence of a base, with either a compound of formula X

X

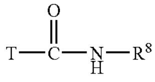

or a compound of formula XI $O{=}C{=}N{-}R^8$ XI wherein T is $C_6$-$C_{10}$-aryloxy or a 5- or 6-membered heterocyclic ring containing at least one ring heteroatom selected from the group consisting of nitrogen, oxygen and sulphur and $R^8$ is as hereinbefore defined;

(F) for the preparation of compounds of formula I wherein $R^3$ is $C_2$-$C_8$-alkynyl, reacting a compound of formula IV where $R^1$ and $R^2$ are as hereinbefore defined, with a compound of formula XII $R^x{-}C{\equiv}C{-}H$ XII wherein $R^x$ is $C_1$-$C_8$-alkyl, in the presence of a base and a catalyst;

(G) for the preparation of compounds of formula I wherein or $R^3$ is $C_1$-$C_8$-alkylaminocarbonyl optionally substituted —NH—C(═O)—NH—$R^8$, reacting a compound of formula XIIa XIIa

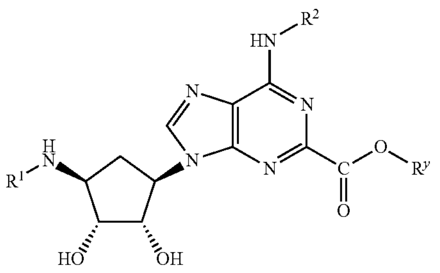

wherein $R^1$ and $R^2$ are as hereinbefore defined and $R^y$ is $C_1$-$C_8$-alkyl, optionally in the presence of a base, with a compound of formula XIIb XIIb

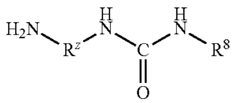

wherein $R^z$ is $C_1$-$C_8$-alkyl and —NH—C(═O)—NH—$R^8$ is as hereinbefore defined; or (H) for the preparation of compounds of formula I wherein $R^3$ is $C_1$-$C_8$-alkylaminocarbonyl substituted by —NH—C(═O)—NH—$R^8$, where $R^8$ is a 5- or 6-membered heterocyclic ring containing at least one ring heteroatom selected from the group consisting of nitrogen, oxygen and sulphur, that ring being substituted by $C_1$-$C_8$-alkylsulfonyl, reacting a compound of formula I wherein $R^3$ is $C_1$-$C_8$-alkylaminocarbonyl substituted by —NH—C(═O)—NH—$R^8$, where $R^8$ is a 5- or 6-membered heterocyclic ring containing at least one ring heteroatom selected from the group consisting of nitrogen, oxygen and sulphur with a sulfonylating agent in the presence of a base;

(I) for the preparation of compounds of formula I wherein $R^3$ is $R^6$ substituted by —NH—C(═O)—NH—$R^7$, where $R^7$ is as hereinbefore defined, reacting a compound of formula XIIc XIIc

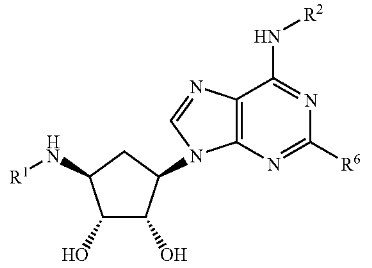

where $R^1$ and $R^2$ are as hereinbefore defined and $R^6$ is a 5- or 6-membered heterocyclic ring containing at least one ring heteroatom selected from the group consisting of nitrogen, oxygen and sulphur, substituted at one position by amino, with either a compound of formula Xa Xa

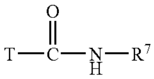

or a compound of formula XIa $O{=}C{=}N{-}R^7$ XIa wherein T is $C_6$-$C_{10}$-aryloxy or a 5- or 6-membered heterocyclic ring containing at least one ring heteroatom selected from the group consisting of nitrogen, oxygen and sulphur and $R^5$ is as hereinbefore defined;

(J) for the preparation of compounds of formula I wherein $R^3$ is $R^6$ substituted by —NH—C(═O)—NH—$R^7$, where $R^7$ is as hereinbefore defined, reacting a compound of formula XIId or XIIe or a protected form thereof XIId

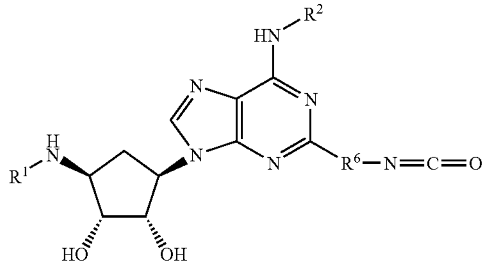

-continued

XIIe

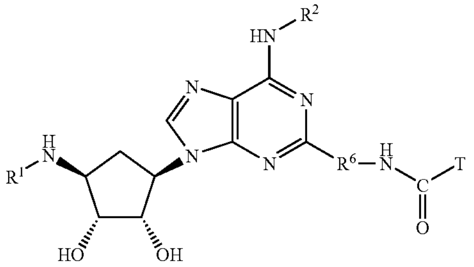

where $R^1$, $R^2$ are $R^6$ are as hereinbefore defined and T is $C_6$-$C_{10}$-aryloxy or a 5- or 6-membered heterocyclic ring containing at least one ring heteroatom selected from the group consisting of nitrogen, oxygen and sulphur, with a compound of formula XIIf XIIf

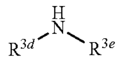

and $R^{3d}$ and $R^{3e}$ together form a 5- or 6-membered N-heterocyclic ring containing at least one ring heteroatom selected from the group consisting of nitrogen, oxygen and sulphur, said 5- or 6-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulphur; or (K) for the preparation of compounds of formula I wherein $R^3$ is $R^6$ substituted by —NH—C(═O)—NH—$R^7$, where $R^7$ is as hereinbefore defined, reacting a compound of formula XIId or XIIe, where $R^1$, $R^2$ are $R^6$ are as hereinbefore defined and T is $C_6$-$C_{10}$-aryloxy or a 5- or 6-membered heterocyclic ring containing at least one ring heteroatom selected from the group consisting of nitrogen, oxygen and sulphur, with a compound of formula XIIg $H_2N—R^7$ XIIg where $R^7$ is as hereinbefore defined; and (ii) removing any protecting groups and recovering the resultant compound of foritula Ia in free or salt form.

Process variant (A) may be carried out using known procedures for reacting amines with acid halides, acid anhydrides or mixed anhydrides e.g. carboxylic and carbonic anhydrides (or amide-forming derivatives thereof such as carboxylic acids) or sulfonyl halides e.g. mesyl halides, or analogously as hereinafter described in the Examples. The leaving group may be any suitable leaving group, for example halo, —$SO_2$—$C_1$-$C_8$-alkyl or —$SO_2$—$C_6$-$C_{10}$-aryl. The reaction is conveniently carried out using an organic solvent, for example tetrahydrofuran (THF), in the presence of a base, for example diisopropylethylamine (DIPEA). Suitable reaction temperatures are from 10° C. to 40° C., preferably room temperature.

Process variant (B) may be carried out using known procedures for reacting halides, especially aromatic halides, with amines, or analogously as hereinafter described in the Examples. The reaction is conveniently carried out using an organic solvent, for example dichlorobenzene, dimethylsulfoxide, acetonitrile or N-methyl-pyrrolidone (NMP) or mixtures thereof optionally in the presence of a catalyst, such as sodium iodide, and a base, such as triethylamine. Suitable reaction temperatures are from 100° C. to 250° C., preferably between 120° C. to 220° C., especially about 170° C., for example by heating with microwave radiation.

Process variant (C) may be carried out using known procedures for reacting halides with amines, or analogously as hereinafter described in the Examples. The reaction is conveniently carried out using an organic solvent, for example tetrahydrofuran, preferably in an inert atmosphere, for example argon, optionally in the presence of a base, for example diisopropyl-ethylamine. Suitable reaction temperatures from 0° C. to 70° C., preferably between 40° C. to 60° C., especially about 50° C.

Process variant (D) may be carried out using known procedures for cleaving ester bonds, for example using a strong organic acid, such as trifluoroacetic acid. The reaction is conveniently carried out using an organic solvent, for example dichloromethane (DCM). Suitable reaction temperatures are from 0° C. to 40° C., preferably room temperature.

Process variant (E) may be carried out using known procedures for reacting amines with acyl-imidazoles or isocyanates, or analogously as hereinafter described in the Examples. T in formula X is preferably imidazolyl. The reaction is conveniently carried out using an organic solvent, for example toluene and/or isopropyl alcohol. Suitable reaction temperatures are from 0° C. to 40° C., preferably room temperature.

Process variant (F) may be carried out using known procedures for reacting halides with alkynes, or analogously as hereinafter described in the Examples. The catalyst is preferably a palladium catalyst (together with a CuI salt) and the base is preferably butylamine. The reaction is conveniently carried out using an organic solvent, such as dimethylformamide (DMF). Suitable reaction temperatures are from 40° C. to 200° C., preferably 80° C. to 160° C., especially about 120° C.

Process variant (G) may be carried out using known procedures for reacting carboxylic acid alkyl esters with amines, or analogously as hereinafter described in the Examples. The base is preferably is preferably imidazole. The reaction is conveniently carried out using an organic solvent, such 1,2-dichloroethane, iso-propanol or a mixture thereof. Suitable reaction temperatures are from room temperature to 250° C., preferably 50° C. to 100° C.

Process variant (H) may be carried out using known procedures for sulfonylating heterocycles, or analogously as hereinafter described in the Examples. The sulphonylating agent is preferably an alkylsulfonylhalide, for example mesylchloride. The base is preferably triethylamine. The reaction is conveniently carried out using an organic solvent, such as dimethylformamide (DMF), preferably in an inert atmosphere. Suitable reaction temperatures are from 0° C. to 40° C., preferably room temperature.

Process variant (I) may be carried out using known procedures for reacting amines with acylimidazoles, isocyanates or arylcarbamates, or analogously as hereinafter described in the Examples. T in formula X is preferably imidazolyl. The reaction is conveniently carried out using an organic solvent, for example tetrahydrofuran or N-methyl-pyrrolidone (NMP), preferably in the presence of a base, for example triethylamine. When the amine is reacted with an acyl-imidazole or an isocyanates suitable reaction temperatures are from 0° C. to 40° C., preferably room temperature. When the amine is reacted with an arylcarbamate, for example phenyl carbamate, suitable reaction temperatures are from room temperature to 120° C., preferably 80° C. to 110° C., especially about 110° C.

Process variant (J) may be carried out using known procedures for reacting N-heterocycles with acyl-imidazoles, isocyanates or arylcarbamates, or analogously as hereinafter described in the Examples. T in formula XIIe is preferably imidazolyl. The reaction is conveniently carried out using an organic solvent, for example tetrahydrofuran or N-methylpyrrolidone (NMP). When the N-heterocycle is reacted with an acyl-imidazole or an isocyanates suitable reaction temperatures are from 0° C. to 40° C., preferably room temperature. When the N-heterocycle is reacted with an arylcarbamate, for example phenyl carbamate, suitable reaction temperatures are from room temperature to 120° C., preferably 80° C. to 110° C., especially about 110° C.

Process variant (K) may be carried out using known procedures for reacting amines with acyl-imidazoles, isocyanates or arylcarbamates, or analogously as hereinafter described in the Examples. The reaction is conveniently carried out using an organic solvent, for example tetrahydrofuran. When the amine is reacted with an acyl-imidazole or an isocyanates suitable reaction temperatures are from 0° C. to 40° C., preferably room temperature. When the amine is reacted with an arylcarbamate, for example phenyl carbamate, suitable reaction temperatures are from room temperature to 120° C., preferably 80° C. to 110° C., especially about 110° C.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula II may be prepared by deprotecting a compound of formula XIII

XIII

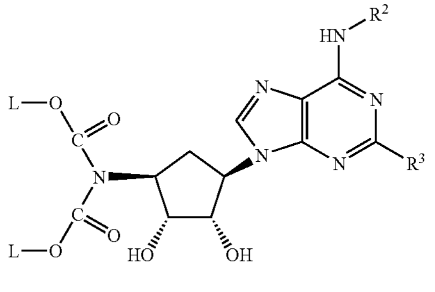

where $R^2$ and $R^3$ are as hereinbefore defined, and each L is $C_1$-$C_8$-alkyl, using known procedures for cleaving ester bonds, or analogously as herein described in the Examples. Preferably the reaction is carried out using a strong organic acid, such as trifluoroacetic acid. Each L is preferably t-butyl. The reaction is conveniently carried out using an organic solvent, for example dichloromethane. Suitable reaction temperatures from 0° C. to 40° C., preferably room temperature.

Compounds of formula III or IIIa are commercially available or may be obtained by known procedures for preparing such compounds, or analogously as herein described in the Examples.

Compounds of formula IV may be prepared by reacting a compound of formula II where $R^3$ is halo, with a compound of formula III or IIIa wherein $R^1$ is as hereinbefore defined, X is a leaving group, preferably halo, and K is hydrogen or $C_1$-$C_8$-alkyl, in the presence of a base, or analogously as herein described in the Examples. The reaction is conveniently carried out using an organic solvent, for example tetrahydrofuran. The base is preferably diisopropylethylamine. Suitable reaction temperatures from 0° C. to 40° C., preferably room temperature.

Compounds of formula Va or formula Vb are either commercially available or may be obtained by known procedures for preparing such compounds, or analogously as herein described in the Examples.

Compounds of formula VI may be prepared by reacting a compound of formula XIV

XIV

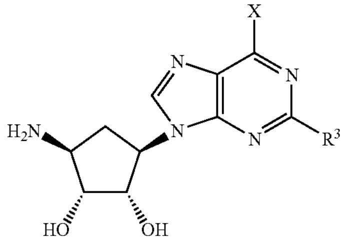

where $R^3$ is as hereinbefore defined and X is halo, with a compound of formula III or IIIa, wherein $R^1$ is as hereinbefore defined, X is a leaving group, preferably halo, and K is hydrogen or $C_1$-$C_8$-alkyl, in the presence of a base, wherein $R^1$ is as hereinbefore defined and X is halo, or analogously as herein described in the Examples. The reaction is conveniently carried out using an organic solvent, for example tetrahydrofuran, preferably in the presence of a base, for example diisopropylethylamine. Suitable reaction temperatures from 0° C. to 40° C., preferably room temperature.

Compounds of formula VII are either commercially available or may be obtained by known procedures for preparing such compounds, or analogously as herein described in the Examples.

Compounds of formula VIII may be prepared by reacting a compound of formula XV

XV

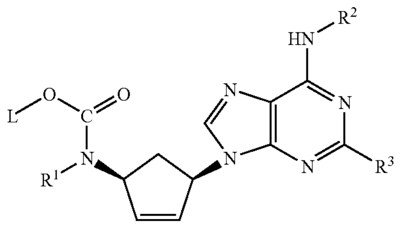

where $R^1$, $R^2$ and $R^3$ are as hereinbefore defined and L is $C_1$-$C_8$-alkyl, with a dehydroxylating agent, such as osmium tetroxide ($O_5O_4$), either in a stoichiometrical amount or a catalytic amount, preferably together with a re-oxidant, such as N-methylmorpholine N-oxide (NMO), or alternatively using AD-mix-α or AD-mix-β, or analogously as herein described in the Examples. L is preferably t-butyl. The reaction is conveniently carried out using an organic solvent, for example THF. Suitable reaction temperatures from 0° C. to 40° C., preferably room temperature.

Compounds of formula IX may be prepared by reacting a compound of formula XVI

XVI

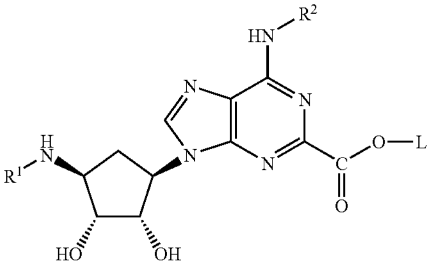

where $R^1$ and $R^2$ are as hereinbefore defined and L is $C_1$-$C_8$-alkyl, is reacted with a compound of formula XVII

XVII

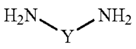

wherein Y is $C_1$-$C_8$-alkyl or $C_3$-$C_8$-cycloalkyl, or analogously as herein described in the Examples. Suitable reaction temperatures from 80° C. to 130° C., preferably 90° C. to 120° C. room temperature, especially about 105° C.

Compounds of formula X, Xa, XI or XIa are commercially available or may be obtained by known procedures for preparing such compounds, or analogously as herein described in the Examples.

Compounds of formula XII are commercially available or may be obtained by known procedures for preparing such compounds, or analogously as herein described in the Examples.

Compounds of formula XIIa may be prepared using the process described herein for preparing compounds of formula XVI, or analogously as herein described in the Examples.

Compounds of formula XIIb are commercially available or may be obtained by known procedures for preparing such compounds, or analogously as herein described in the Examples.

Compounds of formula XIIc may be prepared using a process described herein for preparing compounds of formula I when $R^3$ is $R^6$, or analogously as herein described in the Examples.

Compounds of formula XIId or XIIe may be prepared by reacting a compound of formula I where $R^3$ is $R^6$ substituted by amino, with a suitable acylating agent, or analogously as herein described in the Examples.

Compounds of formula XIIf of XIIg are commercially available or may be obtained by known procedures for preparing such compounds, or analogously as herein described in the Examples.

Compounds of formula XIII may be prepared by reacting a compound of formula XVIII

XVIII

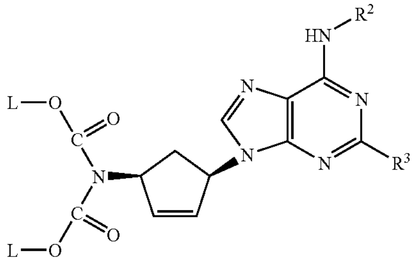

where $R^2$ and $R^3$ are as hereinbefore defined, and each L is $C_1$-$C_8$-alkyl or benzyl, with a hydroxylating agent, such as osmium tetroxide ($O_5O_4$), either in a stoichiometrical amount or a catalytic amount, preferably together with a re-oxidant, such as N-methylmorpholirie N-oxide (NMO), or alternatively using AD-mix-α or AD-mix-β, or analogously as herein described in the Examples. $L^1$ and $L^2$ are preferably t-butyl. The reaction is conveniently carried out using an organic solvent, for example tetrahydrofuran. Suitable reaction temperatures from 0° C. to 40° C., preferably room temperature.

Compounds of formula XIV may be prepared by reacting a compound of formula XIX

XIX

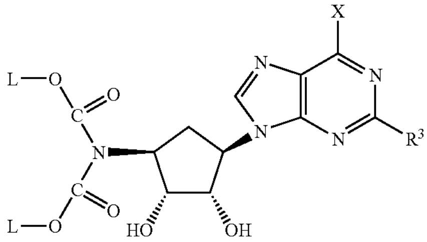

where $R^3$ and X are as hereinbefore defined, and each L is $C_1$-$C_8$-alkyl or benzyl, with a strong organic acid, such as trifluoroacetic acid, or analogously as herein described in the Examples. Each L is preferably t-butyl. The reaction is conveniently carried out using an organic solvent, for example dichloromethane. Suitable reaction temperatures from 0° C. to 40° C., preferably room temperature.

Compounds of formula XV may be prepared by reacting a compound of formula XX

XX

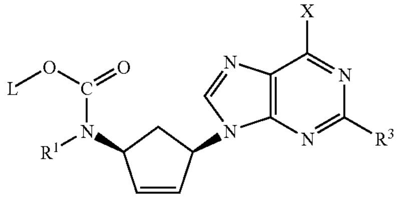

where $R^3$ is as hereinbefore defined, X is halo and L is $C_1$-$C_8$-alkyl or benzyl, with a compound of formula VII, wherein $R^2$ is as hereinbefore defined, or analogously as herein described in the Examples. The reaction is conveniently carried out using an organic solvent, for example tetrahydrofuran, preferably in an inert atmosphere, for example in argon. Suitable reaction temperatures from 30° C. to 70° C., preferably from 40° C. to 60° C., especially about 50° C.

Compounds of XVI may be prepared by reacting a compound of formula XXI

XXI

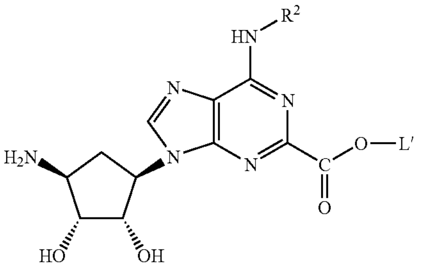

where $R^2$ is as hereinbefore defined and L' is $C_1$-$C_8$-alkyl or benzyl but preferably methyl, with a compound of formula III or IIIa, wherein $R^1$ is as hereinbefore defined, X is a leaving group, preferably halo, and K is hydrogen or $C_1$-$C_8$-alkyl, or analogously as herein described in the Examples. The reaction is conveniently carried out using an organic solvent, for example tetrahydrofuran, preferably in the presence of a base, for example diisopropylethylamine. Suitable reaction temperatures from 0° C. to 40° C., preferably room temperature.

Compounds of formula XVII are commercially available or may be obtained by known procedures for preparing such compounds, or analogously as herein described in the Examples.

Compounds of formula XVIII may be prepared by reacting a compound of formula XXII

XXII

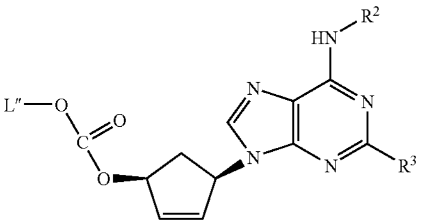

where $R^2$ and $R^3$ are as hereinbefore defined, and L" is $C_1$-$C_8$-alkyl preferably rmethyl or ethyl, with a compound of formula XXIII

XXIII

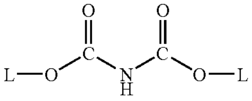

where each L is $C_1$-$C_8$-alkyl or benzyl, preferably benzyl, and preferably in the presence of a catalyst, such as that generated from tetrakis(triphenylphosphine)palladium and triphenylphosphine, or analogously as herein described in the Examples. Preferably each L is t-butyl or benzyl. The reaction is conveniently carried out in an inert environment, for example in argon, using an organic solvent, for example deoxygenated tetrahydrofuran. Suitable reaction temperatures from 0° C. to 40° C., preferably room temperature.

Compounds of formula XIX may be prepared by reacting a compound of formula XXIV

XXIV

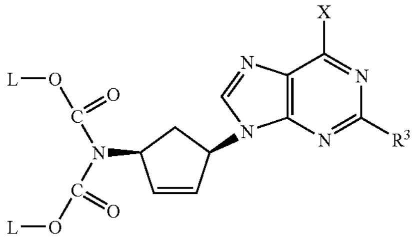

where $R^3$ and X are as hereinbefore defined, and each L is $C_1$-$C_8$-alkyl or benzyl, with a hydroxylating agent, such as osmium tetroxide ($OsO_4$), either in a stoichiometrical amount or a catalytic amount, preferably together with a re-oxidant, such as N-methylmorpholine N-oxide (NMO), or alternatively using AD-mix-α or AD-mix-β, or analogously as herein described in the Examples. Each L is preferably t-butyl. The reaction is conveniently carried out using an organic solvent, for example tetrahydrofuran. Suitable reaction temperatures from 0° C. to 40° C., preferably room temperature.

Compounds of formula XX may be prepared by reacting a compound of formula XXV

XXV

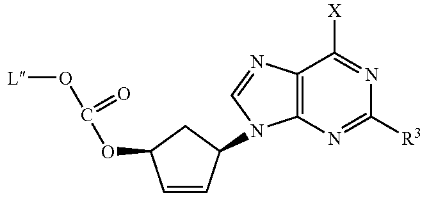

where $R^3$ is as hereinbefore defined, and L" is $C_1$-$C_8$-alkyl, with a compound of formula XXVa XXVa

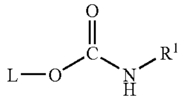

where $R^1$ is as hereinbefore defined, and L is $C_1$-$C_8$-alkyl or benzyl, preferably in the presence of a catalyst, such as that generated from tetrakis(triphenyl-phosphine)palladium and triphenylphosphine, or analogously as herein described in the Examples. Preferably L is t-butyl or benzyl. The reaction is conveniently carried out in an inert environment, for example in argon, using an organic solvent, for example deoxygenated tetrahydrofuran. Suitable reaction temperatures from 0° C. to 40° C., preferably room temperature.

Compounds of XXI may be prepared by reacting a compound of formula XXVI

XXVI

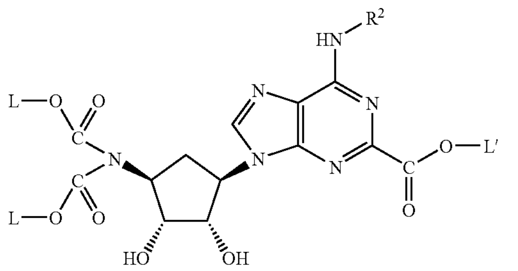

where $R^2$ is as hereinbefore defined, each L is $C_1$-$C_8$-alkyl or benzyl and L' is $C_1$-$C_4$-alkyl, is reacted with a strong acid, for example hydrochloric acid using known procedures for cleaving esters bonds, or analogously as herein described in the Examples. Preferably each L is t-butyl or benzyl and $L^a$ is methyl or ethyl. The reaction is conveniently carried out in an inert environment, for example in argon, using an organic solvent, for example dioxane. Suitable reaction temperatures from 0° C. to 40° C., preferably room temperature.

Compounds of formula XXII may be prepared by reacting a compound of formula XXVII

XXVII

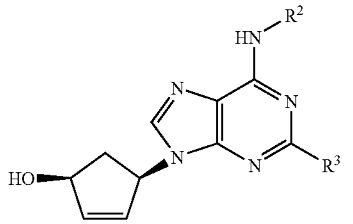

where $R^2$ and $R^3$ are as hereinbefore defined, with an acylating agent such as a carboxylic acid $C_1$-$C_8$-alkyl ester, for example 3-oxy-benzotriazole-1-carboxylic acid ethyl ester, in the presence of a base, such as diisopropylamine, and a catalyst, such as 4-dimethylaminopyridine (DMAP), or analogously as herein described in the Examples. The reaction is conveniently carried out in an inert environment, for example in argon, using an organic solvent, for example deoxygenated THF. Suitable reaction temperatures from 0° C. to 40° C., preferably room temperature.

Compounds of formula XXIII are commercially available or may be obtained by known procedures for preparing such compounds, or analogously as herein described in the Examples.

Compounds of formula XXIV may be prepared by reacting a compound of formula XXVIII

XXVIII

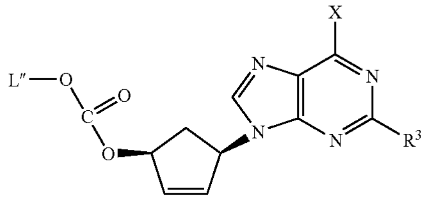

where $R^3$ and X are as hereinbefore defined, and L" is $C_1$-$C_8$-alkyl, with a compound of formula XXIII where each L is $C_1$-$C_8$-alkyl or benzyl, preferably in the presence of a catalyst, such as that generated from tetrakis(triphenylphosphine) palladium and triphenylphosphine, or analogously as herein described in the Examples. Preferably each L is t-butyl or benzyl. The reaction is conveniently carried out in an inert environment, for example in argon, using an organic solvent, for example deoxygenated tetrahydrofuran. Suitable reaction temperatures from 0° C. to 40° C., preferably room temperature.

Compounds of formula XXV may be prepared by reacting a compound of formula XXIX

XXIX

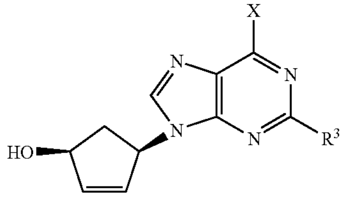

where $R^3$ and X are as hereinbefore defined, with an acylating agent such as a carboxylic acid $C_1$-$C_8$-alkyl ester, for example 3-oxy-benzotriazole-1-carboxylic acid ethyl ester, in the presence of a base, such as diisopropylamine, and a catalyst, such as 4-dimethylaminopyridine (DMAP), or analogously as herein described in the Examples. The reaction is conveniently carried out in an inert environment, for example in argon, using an organic solvent, for example deoxygenated tetrahydrofuran. Suitable reaction temperatures from 0° C. to 40° C., preferably room temperature.

Compounds of formula XXVa are commercially available or may be obtained by known procedures for preparing such compounds, for example as described by Ken-ichi Takana et al in *Chem. Pharm. Bull.* 1988, 36, 3125, or analogously as herein described in the Examples.

Compounds of XXVI may be prepared by reacting a compound of formula XXX

XXX

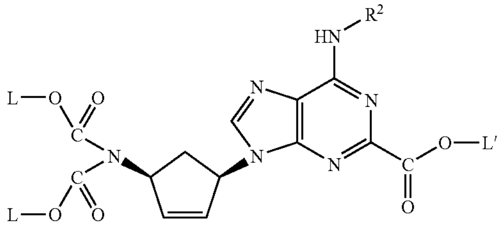

where $R^2$ is as hereinbefore defined, each L is $C_1$-$C_8$-alkyl and L' is $C_1$-$C_4$-alkyl or benzyl, preferably benzyl, is reacted with a hydroxylating agent, such as osmium tetroxide ($OsO_4$), either in a stoichiometrical amount or a catalytic amount, preferably together with a re-oxidant, such as N-methylmorpholine N-oxide (NMO), or alternatively using AD-mix-α or AD-mix-β, or analogously as herein described in the Examples. Preferably each L is t-butyl and $L^a$ is methyl or ethyl. The reaction is conveniently carried out using an organic solvent, for example tetrahydrofuran. Suitable reaction temperatures from 0° C. to 40° C., preferably room temperature.

Compounds of formula XXVII may be prepared by reacting a compound of formula XXXI

XXXI

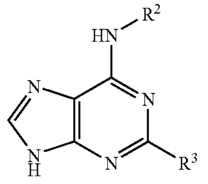

where $R^2$ and $R^3$ are as hereinbefore defined, with (1S,4R)-cis 4-acetoxy-2-cyclopenten-1-ol in the presence of a base, such as sodium hydride, and a catalyst, such as that generated from tetrakis(triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethylsulfoxide (DMSO). Suitable reaction temperatures from 40° C. to 60° C., preferably about 50° C.

Compounds of formula XXVIII may be prepared by reacting a compound of formula XXIX where $R^3$ and X are as hereinbefore defined, with an acylating agent such as a carboxylic acid $C_1$-$C_8$-alkyl ester, for example 3-oxy-benzotriazole-1-carboxylic acid ethyl ester, in the presence of a base, such as diisopropylamine, and a catalyst, such as 4-dimethylaminopyridine (DMAP), or analogously as herein described in the Examples. The reaction is conveniently carried out in an inert environment, for example in argon, using an organic solvent, for example THF. Suitable reaction temperatures from 0° C. to 40° C., preferably room temperature.

Compounds of formula XXIX may be prepared by reacting a compound of formula XXXII

XXXII

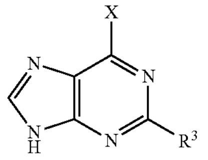

where $R^3$ and X are as hereinbefore defined, with (1S,4R)-cis 4-Acetoxy-2-cyclopenten-1-ol in the presence of a base, such sodium hydride, and a catalyst, such as that generated from tetrakis(triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethylsulfoxide (DMSO). Suitable reaction temperatures from 40° C. to 60° C., preferably about 50° C.

Compounds of formula XXX may be prepared by reacting a compound of formula XXXIII

XXXIII

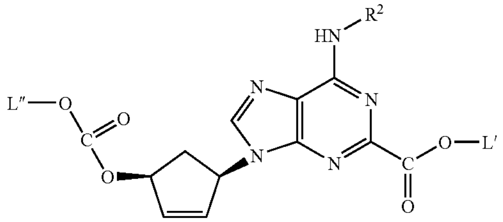

where $R^2$ is as hereinbefore defined, L" is $C_1$-$C_8$-alkyl or benzyl, and L' is $C_1$-$C_4$-alkyl, with a compound of formula XXIII where each L is $C_1$-$C_8$-alkyl, preferably in the presence of a catalyst, such as that generated from tetrakis(triphenylphosphine)palladium and triphenylphosphine, or analogously as herein described in the Examples. Preferably each L" is t-butyl or benzyl and L' is methyl or ethyl. The reaction is conveniently carried out in an inert environment, for example in argon, using an organic solvent, for example deoxygenated tetrahydrofuran. Suitable reaction temperatures from 0° C. to 40° C., preferably room temperature.

Compounds of formula XXXI may be prepared by reacting a compound of formula XXXII where $R^3$ is as hereinbefore defined and X is halo, with a compound of formula VII where $R^2$ is as hereinbefore defined, or analogously as herein described in the Examples. The reaction is conveniently carried out in an inert environment, for example in argon, using an organic solvent, for example tetrahydrofuran. Suitable reaction temperatures from 40° C. to 60° C., preferably about 50° C.

Compounds of formula XXXII are commercially available or may be obtained by known procedures for preparing such compounds, or analogously as herein described in the Examples.

Compounds of formula XXXIII may be prepared by reacting a compound of formula XXXIV

XXXIV

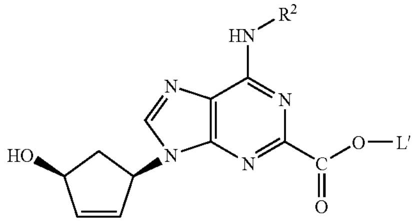

where $R^2$ and L' are as hereinbefore defined, with a compound of formula XXXV

XXXV

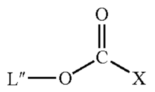

where L" is $C_1$-$C_8$-alkyl, preferably methyl or ethyl, and X is halo, preferably chloro, or analogously as herein described in the Examples. The reaction is conveniently carried out in an inert environment, for example in argon, using an organic solvent, for example deoxygenated tetrahydrofuran, preferably in the presence of a base, for example pyridine. Suitable reaction temperatures from 0° C. to 40° C., preferably room temperature.

Compounds of formula XXXIV may be prepared by reacting a compound of formula XXXVI

XXXVI

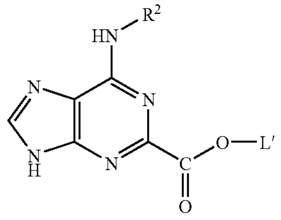

where $R^2$ is as hereinbefore defined and L' is $C_1$-$C_4$-alkyl, preferably methyl or ethyl, with (1S,4R)-cis 4-acetoxy-2-cyclopenten-1-ol in the presence of a base, such sodium hydride, and a catalyst, such as that generated from tetrakis (triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethyl sulfoxide. Suitable reaction temperatures from 60° C. to 100° C., preferably about 80° C.

Compounds of formula XXXV are commercially available or may be obtained by known procedures for preparing such compounds, or analogously as herein described in the Examples.

Compounds of formula XXXVI may be prepared by reacting a salt compound of formula XXXVI where $R^3$ is as hereinbefore defined and L is $C_1$-$C_8$-alkyl, with a silating agent, for example (N,O-bis(trimethylsilyl)acetamide), or analogously as herein described in the Examples. The reaction is conveniently carried out in an inert environment, for example in argon, using an organic solvent, for example dry chloroform. Suitable reaction temperatures from 60° C. to 100° C., preferably about 80° C. The silylated intermediate thus formed is treated with methanol to give the free base.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as stereoisomers, may be obtained in a conventional manner, e.g. by fractional crystallisation or asymmetric synthesis from correspondingly asymmetrically substituted, e.g. optically active, starting materials.

Compounds of formula I and their pharmaceutically acceptable salts are useful as pharmaceuticals. In particular, they activate the adenosine $A_{2A}$ receptor, i.e. they act as $A_{2A}$ receptor agonists. Their properties as $A_{2A}$ agonists may be demonstrated using the method described by L. J. Murphree et al in *Molecular Pharmacology* 61, 455-462 (2002).

Compounds of the Examples hereinbelow have $K_i$ values below 1.0 μM in the above assay. For example, the compounds of Examples 1, 2, 4, 6, 12, 14, 20, 33, 38, 39, 42, 47, 55 and 61 have $K_i$ values of 0.582, 0.018, 0.057, 0.008, 0.003, 0.690, 0.008, 0.052, 0.002, 0.003, 0.002, 0.002, 0.004 and 0.009 μM respectively.

Having regard to their activation of the adenosine $A_{2A}$ receptor, compounds of formula I in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Other diseases or conditions which may be treated with agents of the invention include diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterised by elevated intraocular pressure or secretion of ocular aqueous humor, such as glaucoma, ischemic tissue/organ damage from reperfusion and bedsores.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; Cernadas et al (1999) *Am. J. Respir. Cell Mol. Biol.* 20:1-8; and Fozard et al (2002) *European Journal of Pharmacological* 438, 183-188.

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BILL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/U565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine $A_{2B}$ receptor antagonists such as those described ir-WO 02/42298; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

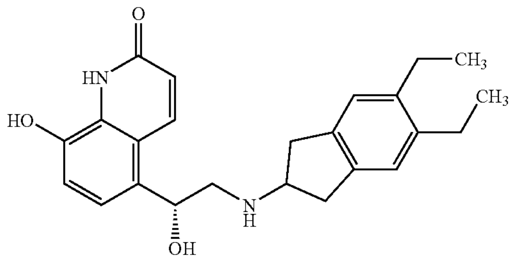

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140 and WO 05/07908.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. Nos. 3,714,357, 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to activation of the adenosine $A_{2A}$ receptor, for example an inflammatory or allergic condition, particularly an inflammatory or obstructive airways disease, which comprises administering to a subject, particularly a human subject, in need thereof a compound of formula I in free form or in the form of a pharmaceutically acceptable salt. In another aspect the invention provides a compound of formula I, in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) a compound of formula I in inhalable form, e.g. in an aerosol or other atomisable composition or in inhalable particulate, e.g. micronised, form, (B) an inhalable medicament comprising a compound of formula I in inhalable form; (C) a pharmaceutical product comprising a compound of formula I in inhalable form in association with an inhalation device; and (D) an inhalation device containing a compound of formula I in inhalable form.

Dosages of compounds of formula I employed in practicing the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLES

Preferred compounds of formula I

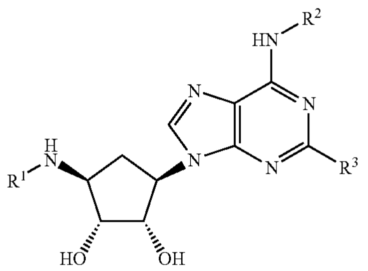

include those shown in Table 1 below. Methods for preparing such compounds are described hereinafter. The table also shows mass spectrometry, MH+ {ESMS}, data. The Examples are in free form, except for Examples 1-3, 7, 9-11 and 17-37, which are trifluoroacetate salts.

TABLE 1
| Ex. | R[1] | R[2] | R[3] | MH+ or MH+/2 |
|---|---|---|---|---|
| 1 | 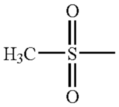 | —H | —Cl | 363.10 |
| 2 | 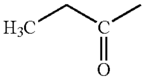 | —H | 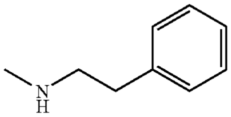 | 426.27 |
| 3 | 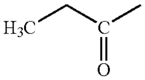 | —H | 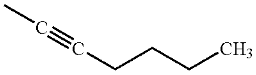 | 387.25 |
| 4 | 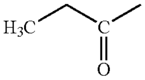 | 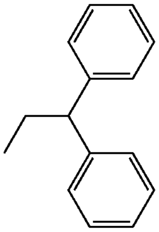 | —Cl | 521.30 |
| 5 | 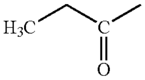 | 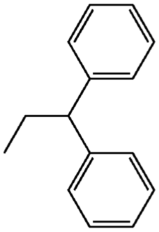 | 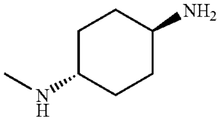 | 599.28<br>599.41 |
| 6 | 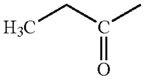 | 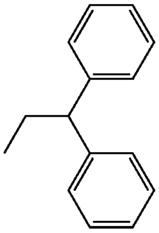 | 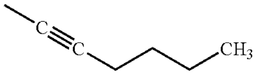 | 567.24 |
| 7 | 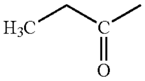 | 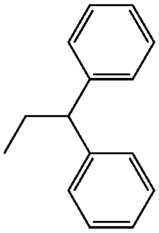 | 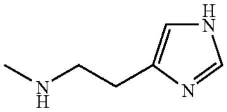 | 596.36 |
| 8 | 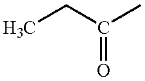 | 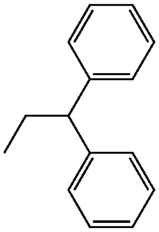 | 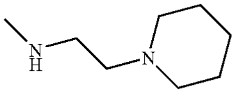 | 613.42<br>613.43 |

TABLE 1-continued
| Ex. | $R^1$ | $R^2$ | $R^3$ | MH+ or MH+/2 |
|---|---|---|---|---|
| 9 | 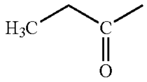 | 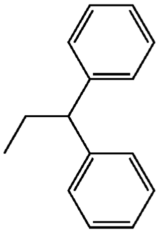 | 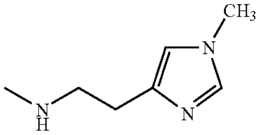 | 610.35 |
| 10 | 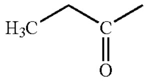 | 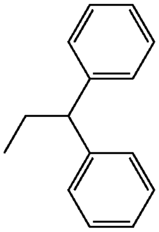 | 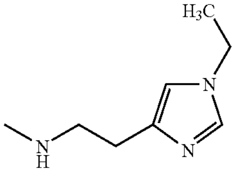 | 624.38 |
| 11 | 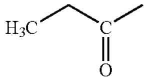 | 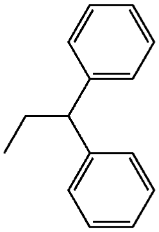 | 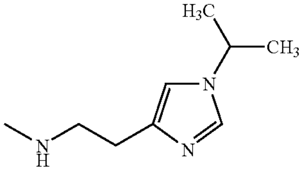 | 638.39 |
| 12 | 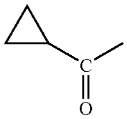 | 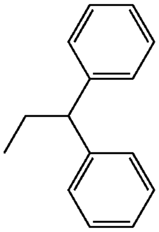 | —Cl | 533.25 |
| 13 | 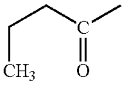 | 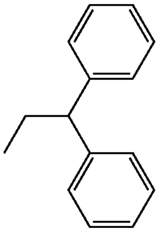 | —Cl | 535.26 |
| 14 | 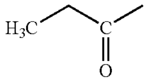 | 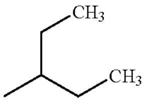 | —Cl | 411.21 |
| 15 | 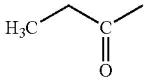 | 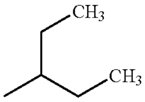 | 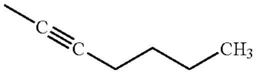 | 457.30 |

TABLE 1-continued
| Ex. | $R^1$ | $R^2$ | $R^3$ | MH+ or MH+/2 |
|---|---|---|---|---|
| 16 | 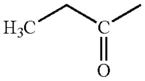 | 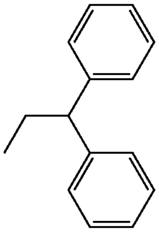 | 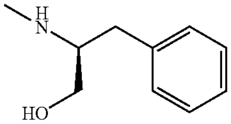 | 636.37 |
| 17 | 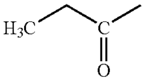 | 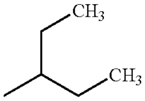 | 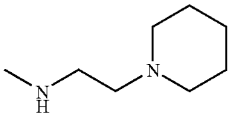 | 503.34 |
| 18 | 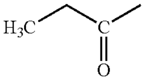 | 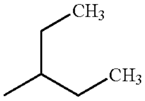 | 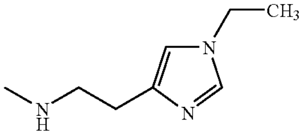 | 514.30 |
| 19 | 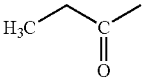 | 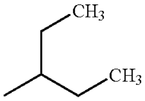 | 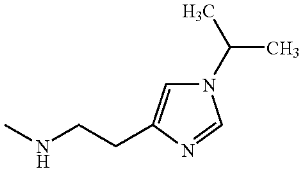 | 528.33 |
| 20 | 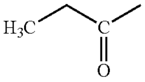 | 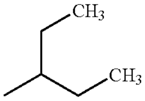 | 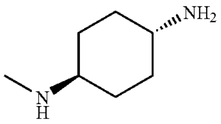 | 489.33 |
| 21 | 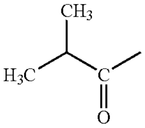 | —H | 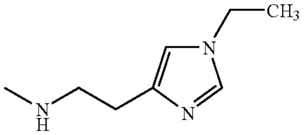 | 458.26 |
| 22 | 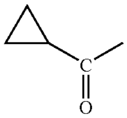 | 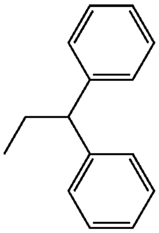 | 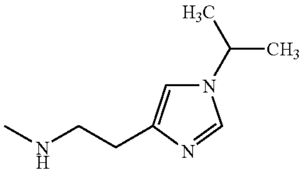 | 650.22 |
| 23 | 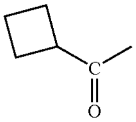 | 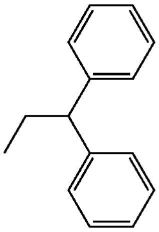 | 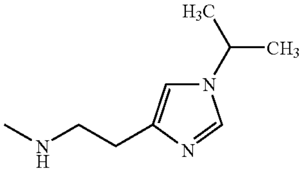 | 664.45 |

TABLE 1-continued
| Ex. | $R^1$ | $R^2$ | $R^3$ | MH+ or MH+/2 |
|---|---|---|---|---|
| 24 | 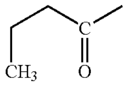 | 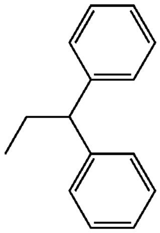 | 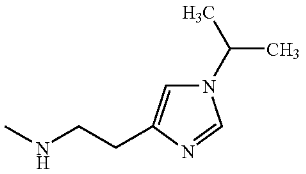 | 652.45 |
| 25 | 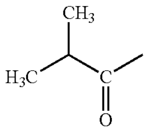 | 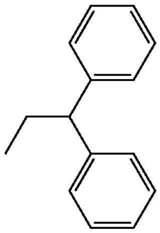 | 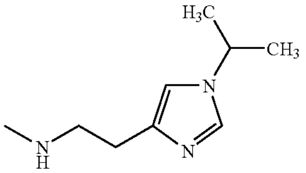 | 652.44 |
| 26 | 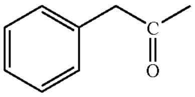 | 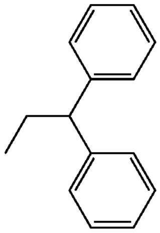 | 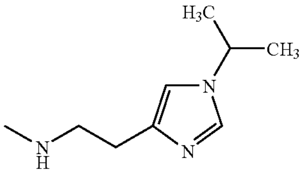 | 700.45 |
| 27 | 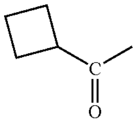 | 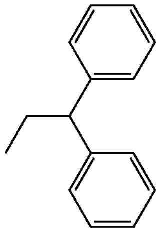 | 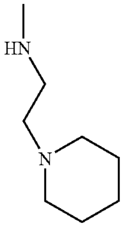 | 639.46 |
| 28 | 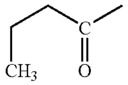 | 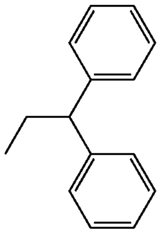 | 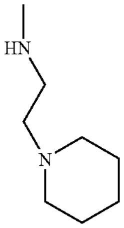 | 627.45 |
| 29 | 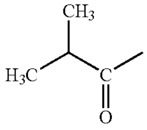 | 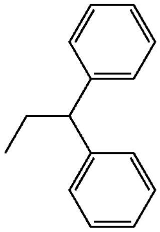 | 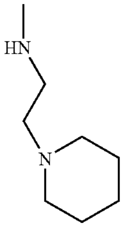 | 627.45 |

TABLE 1-continued
| Ex. | $R^1$ | $R^2$ | $R^3$ | MH+ or MH+/2 |
|---|---|---|---|---|
| 30 | 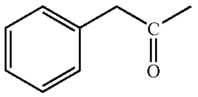 | 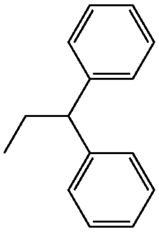 | 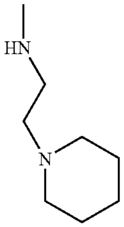 | 675.47 |
| 31 | 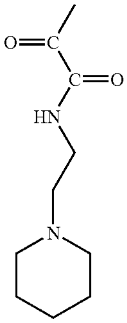 | 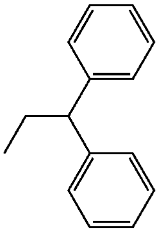 | 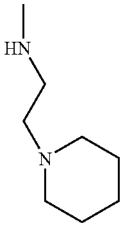 | 739.55 |
| 32 | 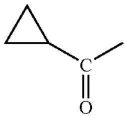 | 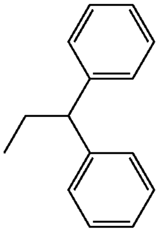 | 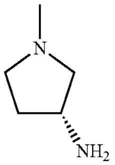 | 538.42 |
| 33 | 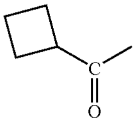 | 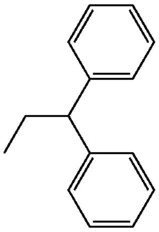 | 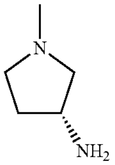 | 597.45 |
| 34 | 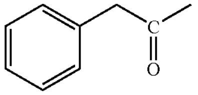 | 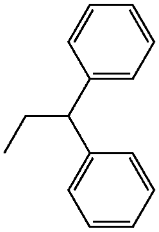 | 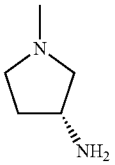 | 633.46 |
| 35 | 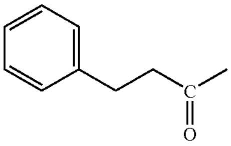 | 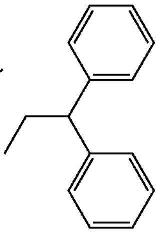 | 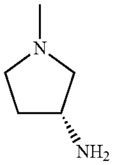 | 647.47 |

TABLE 1-continued
| Ex. | $R^1$ | $R^2$ | $R^3$ | MH+ or MH+/2 |
|---|---|---|---|---|
| 36a | 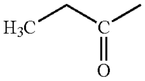 | 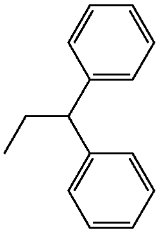 | 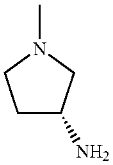 | 571.41 |
| 36b | 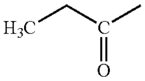 | 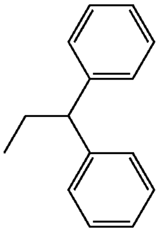 | 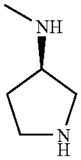 | 571.41 |
| 37a | 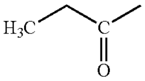 | 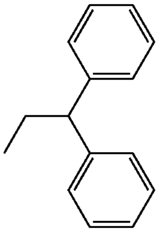 | 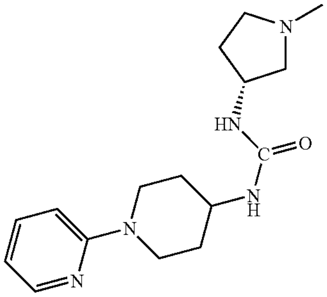 | 596.42 |
| 37b | 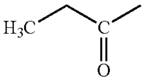 | 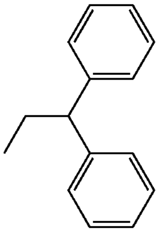 | 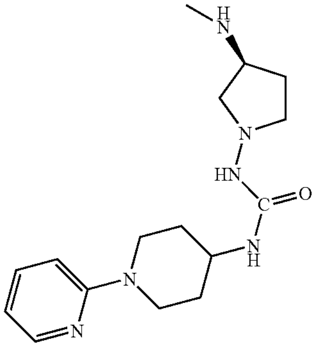 | 596.42 |
| 38 | 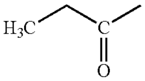 | 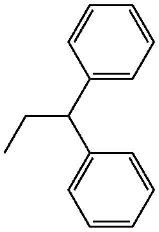 | 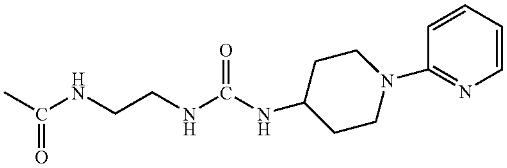 | 388.7<br>338.8 |

Further preferred examples of compounds of formula I are shown in Table 2 below. Methods for preparing such compounds are described hereinafter. The table also shows mass spectrometry, MH+ {ESMS}, data. The compounds of the examples are trifluoroacetate salts, except for the compounds of Examples 41, 48, 52 and 53 are in free form and the compound of Examples 44 is an hydrochloride salt.

TABLE 2

| Ex. | $R^1$ | $R^2$ | $R^3$ | MH+ or MH+/2 |
|---|---|---|---|---|
| 39 | 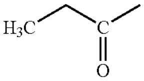 | 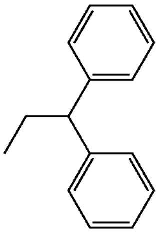 | 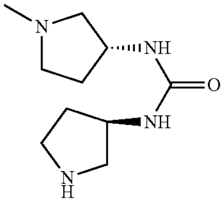 | 683.6 |
| 40 | 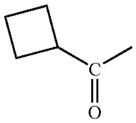 | 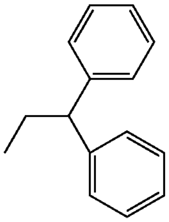 | 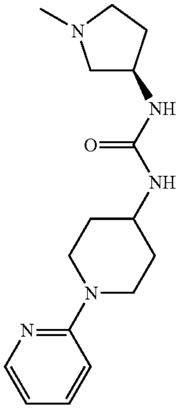 | 800.6 |
| 41 | 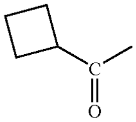 | 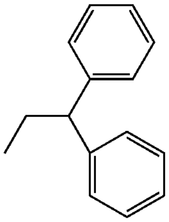 | 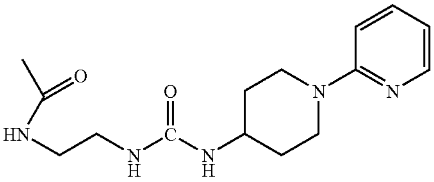 | 802.6 |
| 42 | 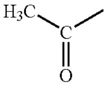 | 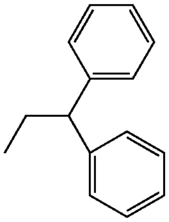 | 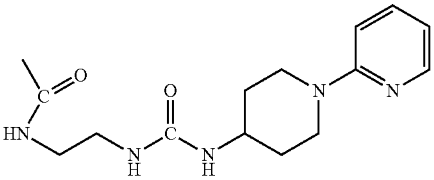 | 762.6 |
| 43 | 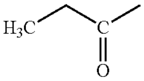 | 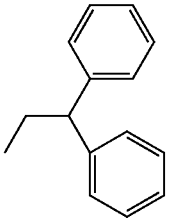 | 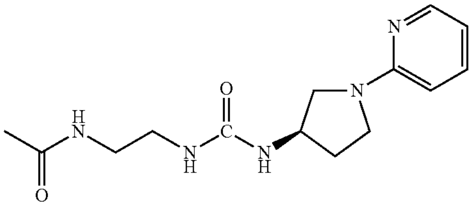 | 762.5 |

TABLE 2-continued
| Ex. | $R^1$ | $R^2$ | $R^3$ | MH+ or MH+/2 |
|---|---|---|---|---|
| 44 | 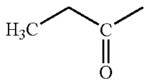 | 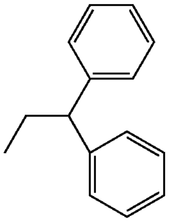 | 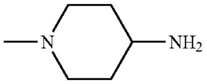 | 585.5 |
| 45 | 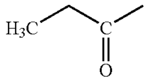 | 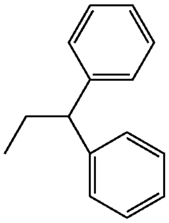 | 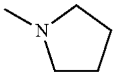 | 556.5 |
| 46 | 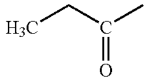 | 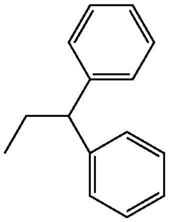 | 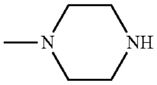 | 571.5 |
| 47 | 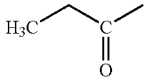 | 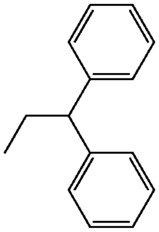 | 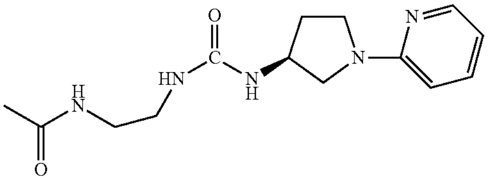 | 382.9 |
| | | | 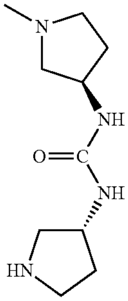 | |
| 48 | 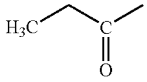 | 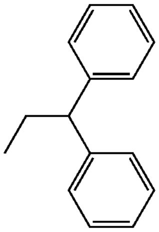 | 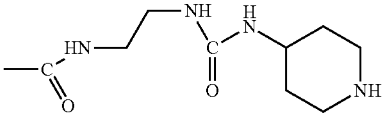 | 699.6 |

TABLE 2-continued
| Ex. | $R^1$ | $R^2$ | $R^3$ | MH+ or MH+/2 |
|---|---|---|---|---|
| 49 | 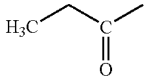 | 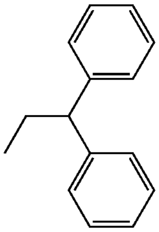 | 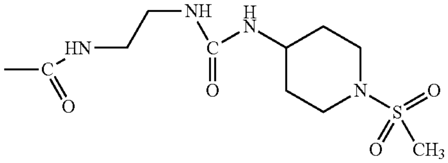 | 777.6 |
| 50 | 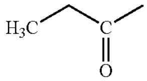 | 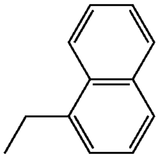 | —Cl | 481.3 |
| 51 | 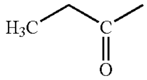 | 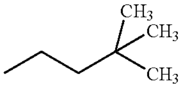 | —Cl | 425.2 |
| 52 | 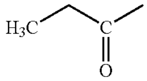 | 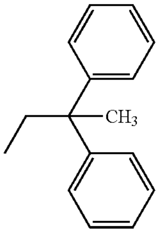 | —Cl | 535.3 |
| 53 | 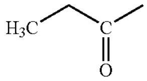 | 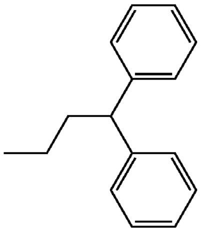 | —Cl | 535.5 |
| 54 | 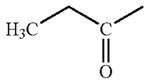 | 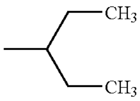 | 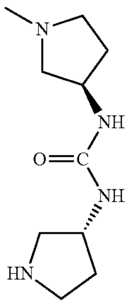 | 573.4 |

TABLE 2-continued
| Ex. | $R^1$ | $R^2$ | $R^3$ | MH+ or MH+/2 |
|---|---|---|---|---|
| 55 | 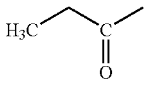 | 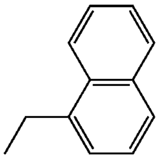 | 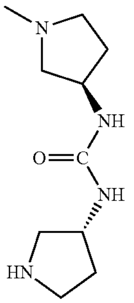 | 643.4 |
| 56 | 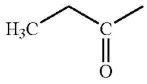 | 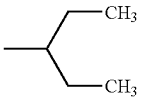 | 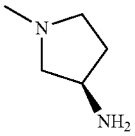 | 461.3 |
| 57 | 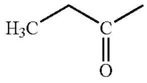 | 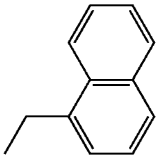 | 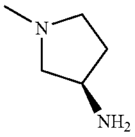 | 531.3 |
| 58 | 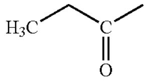 | 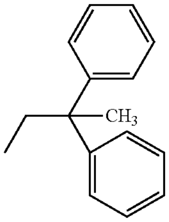 | 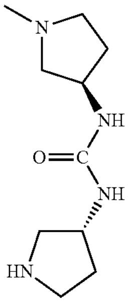 | 697.5 |
| 59 | 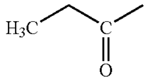 | 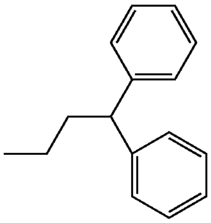 | 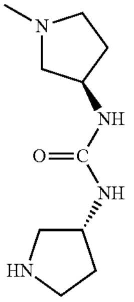 | 697.5 |
| 60 | 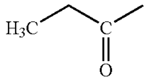 | 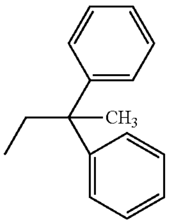 | 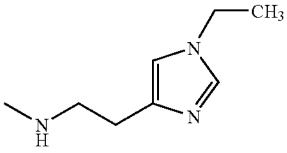 | 638.4 |

TABLE 2-continued

| Ex. | $R^1$ | $R^2$ | $R^3$ | MH+ or MH+/2 |
|---|---|---|---|---|
| 61 | 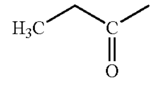 | 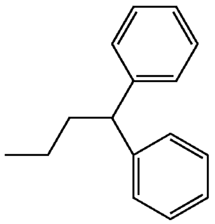 | 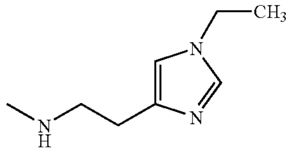 | 638.4 |
| 62 | 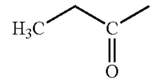 | 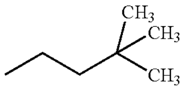 | 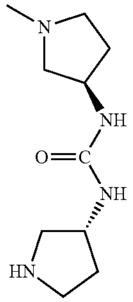 | 587.3 |

Further preferred examples of compounds of formula I are shown in Table 3 below. Methods for preparing such compounds are described hereinafter. The table also shows mass spectrometry, MH+ {ESMS}, data. The compounds of the examples are trifluoroacetate salts, except for the compound of Example 76 which is in free form and the compound of Example 79 which is a hydrochloride salt.

TABLE 3

| Ex. | $R^1$ | $R^2$ | $R^3$ | MH+ or MH+/2 |
|---|---|---|---|---|
| 63 | 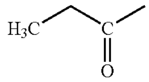 | 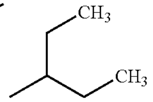 | 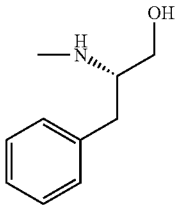 | 526.5 |
| 64 | 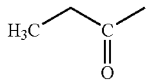 | 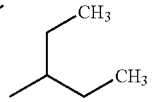 | 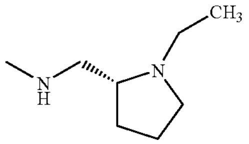 | 503.5 |
| 65 | 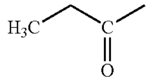 | —H | 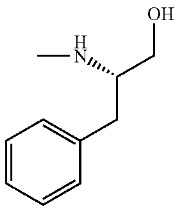 | 456.4 |

TABLE 3-continued
| Ex. | $R^1$ | $R^2$ | $R^3$ | MH+ or MH+/2 |
|---|---|---|---|---|
| 66 | 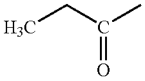 | 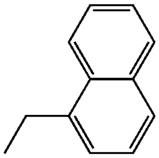 | 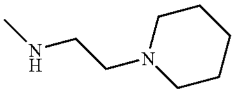 | 573.5 |
| 67 | 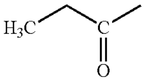 | 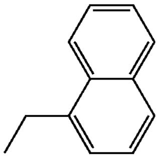 | 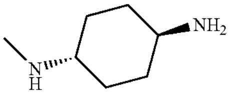 | 559.5 |
| 68 | 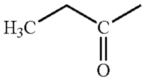 | 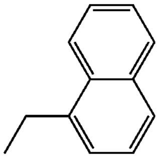 | 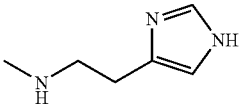 | 556.5 |
| 69 | 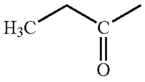 | 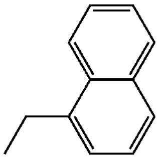 | 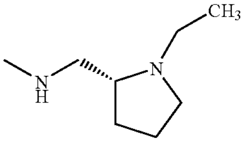 | 573.5 |
| 70 | 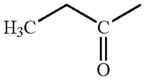 | 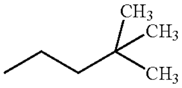 | 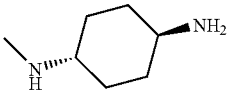 | 503.5 |
| 71 | 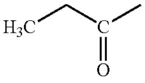 | 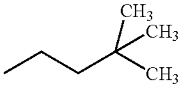 | 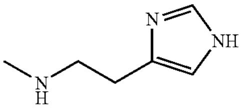 | 500.5 |
| 72 | 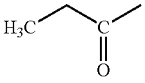 | 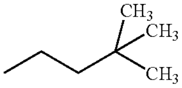 | 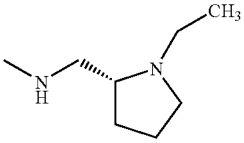 | 517.6 |
| 73 | 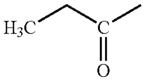 | 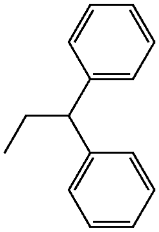 | 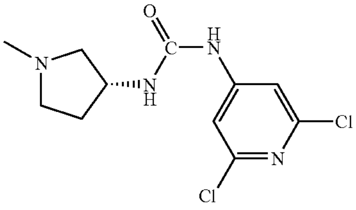 | 759.4 |
| 74 | 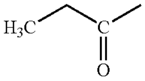 | 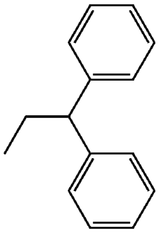 | 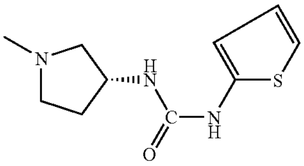 | 696.4 |

TABLE 3-continued

| Ex. | $R^1$ | $R^2$ | $R^3$ | MH+ or MH+/2 |
|---|---|---|---|---|
| 75 | 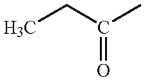 | 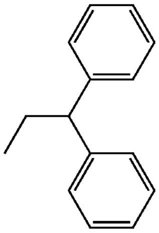 | 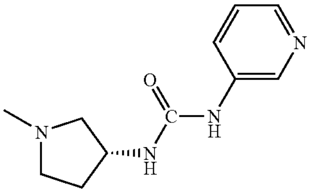 | 691.5 |
| 76 | 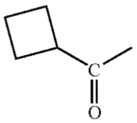 | 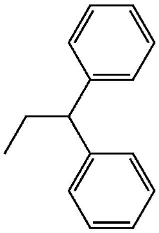 | 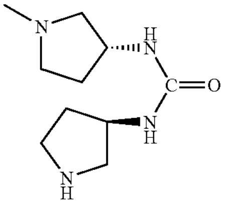 | 709.2 |
| 77 | 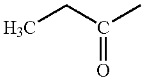 | 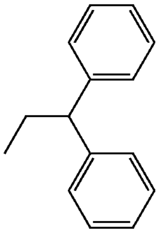 | 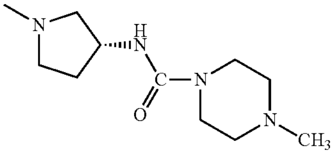 | 697.4 |
| 78 | 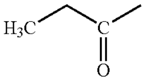 | 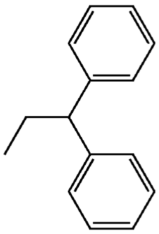 | 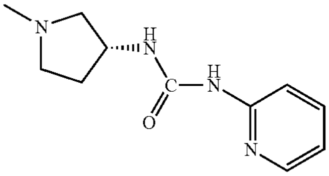 | 691.4 |
| 79 | 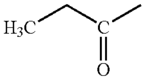 | 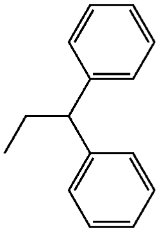 | 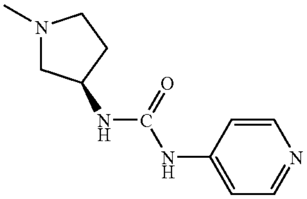 | 705.3 |
| 80 | 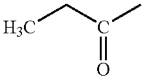 | —H | 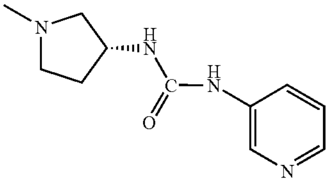 | — |

Preparation of Intermediate Compounds

Abbreviations used are as follows: CDI is 1,1'-carbonyldiimidazole, DCM is dichloromethane, DIPEA is diisopropylethylamine, DMAP is 4-dimethylaminopyridine, DMF is dimethyl-formamide, DMSO is dimethylsulfoxide, LCMS is liquid chromatographic mass spectroscopy, TEA is triethylamine, TFA is trifluoroacetic acid, THF is tetrahydrofuran, and TLC is thin-layer chromatography.

3-Oxy-benzotriazole-1-carboxylic acid ethyl ester

This compound is prepared from 1-hydroxybenzotriazole by the procedure of Wuts, Peter G. M. et al *Organic Letters*

(2003), 5(9), 1483-1485. $^1$H nmr ($CDCl_3$, 400 MHz); 8.20 (d, 1H), 8.00(d, 1H), 7.75(t, 1H), 7.55(t, 1H), 4.60(q, 2H), 1.55(t, 3H).

2-(1-Isopropyl-1H-imidazol-4-yl)-ethylamine

This compound is prepared from 2-isopropyl-5-oxo-5,6,7,8-tetrahydro-imidazo[1,5-c]pyrimidin-2-ium iodide by the procedure of Rahul Jain and Louis A. Cohen *Tetrahedron* 1996, 52, 5363. $^1$H nmr (MeOD, 400 MHz); 7.60(s, 1H), 6.95(s, 1H), 4.40(m, 1H), 2.90(t, 2H), 2.70(t, 2H), 1.45(d, 6H).

Propionyl-Carbamic Acid Tert-Butyl Ester

The title compound is prepared from propyl-carbamic acid tert-butyl ester using the procedure described by Ken-ichi Takana et al in *Chem. Pharm. Bull.* 1988, 36, 3125. $^1$H nmr ($CDCl_3$, 400 MHz); 7.25(br s, 1H), 2.75(q, 2H), 1.50(s, 9H), 1.15(t, 3H).

Bis-(4-methoxy-phenyl)-methanone oxime 4,4'-Dimethoxybenzophenone (25 g, 103 mmol) is suspended in ethanol (150 ml) and pyridine (30 ml). Hydroxylamine hydrochloride (21.50 g, 310 mmol) is added and the reaction mixture is refluxed. The reaction is shown to be complete by TLC after 3 hours. The reaction mixture is allowed to cool and the solvent is removed in vacuo. The residue is partitioned between ethyl acetate (500 ml) and water (500 ml). The organic layer dried is over $MgSO_4$, filtered and the solvent removed in vacuo. The title compound is obtained following crystallisation from ethylacetate/cyclohexane. $^1$H nmr ($CDCl_3$, 400 MHz); 7.70(s, 1H), 7.40(d of d, 4H), 6.95(d, 2H), 6.85(d, 2H), 3.85(s, 3H), 3.80(s, 3H).

C,C-Bis-(4-methoxy-phenyl)-methylamine

Bis-(4-methoxy-phenyl)-methanone oxime (20 g, 77.82 mmol) is suspended in ammonia 0.880(450 ml) and ethanol (90 ml). Ammonium acetate (3.00 g, 38.91 mmol) is added followed by the portionwise addition of zinc dust (25.29 g, 389.10 mmol). Once the addition is complete the reaction mixture is slowly heated to 50° C. When the effervescence has ceased the reaction mixture is refluxed. The reaction is shown to be complete by TLC after 4 hours. The reaction mixture is allowed to cool and ethyl acetate is added (250 ml). The reaction mixture is filtered through Celite™ and the phases are separated. The organic layer dried is over $MgSO_4$, filtered and the solvent removed in vacuo to give the title compound. $^1$H nmr ($CDCl_3$, 400 MHz); 7.25 (d, 4H), 6.80(d, 4H), 5.10(s, 1H), 3.75(s, 6H).

1,3-Di(R)-pyrrolidin-3-yl-urea (a) 1,3-Bis-((R)-1-benzyl-pyrrolidin-3-yl)-urea

A solution comprising (R)-1-benzyl-pyrrolidin-3-ylamine (5.0 g, 28.4 mmol) in DCM (10 ml) is treated with CDT (2.3 g, 14.2 mmol) and the reaction mixture is stirred at room temperature for 48 hours. The solvent is removed in vacuo and the resulting residue is dissolved in ethyl acetate. This portion is washed with water followed by brine, dried ($MgSO_4$) and concentrated in vacuo to yield the titled compound as pale orange solid.

(b) 1,3-Di(R)-pyrrolidin-3-yl-urea

To a solution of 1,3-bis-((R)-1-benzyl-pyrrolidin-3-yl)-urea (5.34 g, 14.1 mmol) in ethanol (80 ml) under an inert atmosphere of Argon is added palladium hydroxide on carbon (1.07 g). The reaction mixture is purged with Argon and placed under an atmosphere of hydrogen for two days after which time, the mixture is filtered and the catalyst washed with ethanol. The organic portions are combined and concentrated in vacuo to yield the titled compound as a white solid.

Imidazole-1 carboxylic acid (3,4,5,6-tetrahydro-2H-[1,2']bipyridinyl-4-yl)-amide A stirred solution of CDI (1.1 g, 6.77 mmol) in DCM (100 ml) is treated with 3,4,5,6-tetrahydro-2H-[1,2']bipyridinyl-4-ylamine (WO 99/65895, EP 21973) (1 g, 5.64 mmol in 50 ml of DCM) added dropwise over 30 minutes. The reaction mixture is stirred at room temperature for 15 minutes to yield the titled compound as a 10 mg/ml solution in DCM.

The compound is used in solution in subsequent reactions. This solution consists of the imidazole-urea intermediate (C) together with variable amounts of the corresponding isocyanate and imidazole which result from reversible thermal elimination of imidazole under the reaction conditions. This solution is used in the subsequent steps since the imidazole-urea intermediate and isocyanate intermediate are equally suitable as precursors to ureas.

1-(2-Amino-ethyl)-3-((S)-1-pyridin-2-yl-pyrrolidin-3-yl)-urea (a) ((S)-1-Pyridin-2-yl-pyrrolidin-3-yl)-carbamic acid tert-butyl ester A stirred solution comprising (S)-pyrrolidin-3-yl-carbamic acid tert-butyl ester (2.0 g, 10.7 mmol), 2-bromopyridine (1.7 g, 10.7 mmol) and TEA (1.1 g, 10.7 mmol) in DMF (40 ml) is heated to 80° C. for 50 hours. The solvent is removed in vacuo the purification of the crude residue by chromatography on silica eluting with ethyl acetate:hexane (1:9 increasing to 1:4) yields the titled compound as a white solid.

(b) (S)-1-Pyridin-2-yl-pyrrolidin-3-ylamine dihydrochloride

To a solution of ((S)-1-pyridin-2-yl-pyrrolidin-3-yl)-carbamic acid tert-butyl ester (0.221 g, 0.84 mmol) in dioxane (4 ml) and methanol (1 ml) is added 4M HCl (in dioxane) (0.525 ml, 2.1 mmol) and the reaction mixture is stirred at room temperature overnight. The resulting suspension is filtered and washed with dioxane (3×1 ml) to yield the titled compound.

(c) Imidazole-1-carboxylic acid ((S)-1-pyridin-2-yl-pyrrolidin-3-yl)-amide

A mixture comprising ((S)-1-Pyridin-2-yl-pyrrolidin-3-ylamine dihydrochloride (0.242 g, 1.02 mmol), TEA (0.2 ml) in DCM (10.2 ml) is treated with CDI (0.364 g, 2.26 mmol). The reaction mixture is stirred at room temperature for 2 hours to yield the titled compound as 0.1 M solution in DCM. This solution consists of the imidazole-urea intermediate together with variable amounts of the corresponding isocyanate and imidazole. This solution is used in the subsequent steps since the imidazole-urea intermediate and isocyanate intermediate are equally suitable as precursors to ureas.

(d) 1-(2-Amino-ethyl)-3-((S)-1-pyridin-2-yl-pyrrolidin-3-yl)-urea

To a solution of imidazole-1-carboxylic acid ((S)-1-pyridin-2-yl-pyrrolidin-3-yl)-amide (9.9 ml of a 0.1 M solution in DCM, 0.99 mmol) in iso-propanol (1 ml) is added ethyl-1,2-diamine (2 ml, 37 mmol). The reaction mixture is stirred at room temperature for 4 hours and then extracted with DCM using a continuous liquid-liquid extraction system to yield the titled compound as 1:4 mole ratio mixture with imidazole.

1-(2-Amino-ethyl)-3-((R)-1-pyridin-2-yl-pyrrolidin-3-yl)-urea

The titled compound is prepared analogously to Intermediate D by replacing (S)-pyrrolidin-3-yl-carbamic acid tert-butyl ester with (R)-pyrrolidin-3-yl-carbamic acid tert-butyl ester and replacing 2-bromopyridine with 2-chloropyridine.

[(1S,2R,3S,4R)-4-(2,6-Dichloro-purin-9-yl)-2,3-dihydroxy-cyclopentyl]-propionyl-carbamic acid tert-butyl ester The titled compound is prepared analogously to 9-[(1R,2S,3R,4S)-4-(tert-butoxycarbonyl-propionyl-amino)-2,3-dihydroxy-cyclopentyl]-6-(2,2-diphenyl-ethylamino)-9H-purine-2-carboxylic acid methyl ester (Example 38) by replacing 9-[(1R,4S)-4-(tert-butoxycarbonyl-propionyl-amino)-cyclopent-2-enyl]-6-(2,2-diphenyl-ethylamino)-9H-purine-2-carboxylic acid methyl ester with [(1S,4R)-4-(2,6-dichloro-p urin-9-yl)-cyclopent-2-enyl]-propionyl-carbamic acid tert-butyl ester.

N-{(3aR,4S,6R,6aS)-6-[2-((R)-3-Amino-pyrrolidin-1-yl)-6-(2,2-diphenyl-ethylamino)-purin-9-yl]-2,2-dimethyl-tetrahydro-cyclopenta[1,3]dioxol-4-yl}-propionamide a) {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid benzyl ester A solution of (R)-pyrrolidin-3-yl-carbamic acid benzyl ester hydrochloride (0.88 g, 3.45 mmol) in DCM is free-based using sodium hydrogen carbonate solution to yield (R)-pyrrolidin-3-yl-carbamic acid benzyl ester (0.487 g, 2.22 mmol). This amine is added to N-{(1S,2R,3S,4R)-4-[2-chloro-6-(2,2-diphenyl-ethylamino)-purin-9-yl]-2,3-dihydroxy-cyclopentyl}-propionamide (Example 4) (0.5 g, 0.96 mmol) and TEA (0.224 g, 2.22 mmol) and then dissolved in NMP (7 ml). The reaction mixture is heated using microwave radiation in a Personal Chemistry Emrys™ Optimizer microwave reactor at 190° C. for 1 hour. The resulting mixture is purified by chromatography on silica eluting with 5% MeOH in DCM to yield the titled compound.

b) {(R)-1-[9-((3aS,4R,6S,6aR)-2,2-Dimethyl-6-propionylamino-tetrahydro-cyclopenta[1,3]dioxol-4-yl)-6-(2,2-diphenyl-ethylamino)-9H-purin-2-yl]-pyrrolidin-3-yl}-carbamic acid benzyl ester A solution of {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-carbamic acid benzyl ester (0.63 g, 0.89 mmol) in acetone (10 ml) and 2,2-dimethyloxypropane (5 ml) is treated with toluenesulfonic acid (ca.60 mg) and then stirred at room temperature overnight. The mixture is basified using ammonium hydroxide and the solvent is removed in vacuo. The crude product is partitioned between DCM and water and the organic portion is washed with brine, dried over $MgSO_4$, filtered and the solvent is removed in vacuo to give the titled compound. [MH+ 745].

c) N-{(3aR,4S,6R,6aS)-6-[2-((R)-3-Amino-pyrrolidin-1-yl)-6-(2,2-diphenyl-ethylamino)-purin-9-yl]-2,2-dimethyl-tetrahydro-cyclopenta[1,3]dioxol-4-yl}-propionamide To a solution of {(R)-1-[9-((3aS,4R,6S,6aR)-2,2-dimethyl-6-propionylamino-tetrahydro-cyclopenta[1,3]dioxol-4-yl)-6-(2,2-diphenyl- ethylamino)-9H-purin-2-yl]-pyrrolidin-3-yl}-carbamic acid benzyl ester (0.598 g, 0.79 mmol) in ethanol (7.5 ml) under an inert atmosphere of Argon is added palladium hydroxide on carbon (10 mg). The reaction mixture is purged with Argon and placed under an atmosphere of hydrogen overnight. The mixture is filtered and purified by chromatography on silica eluting with 5% MeOH in DCM to yield the title d compound. [MH+ 611].

Preparation of Specific Examples

Example 1

N-[(1S,2R,3S,4R)-4-(6-Amino-2-chloro-purin-9-yl)-2,3-dihydroxy-cyclopentyl]-methanesulfonamide trifluoroacetate Bis-(4-methoxy-phenyl)-methyl]-(2-chloro-9H-purin-6-yl)-amine 2,6-Dichloropurine (9.50 g, 50.29 mmol) is dissolved in THF (200 ml) under an atmosphere of argon. Diisopropylamine (7.14 g, 55.32 mmol) is added followed by C,C-bis-(4-methoxy-phenyl)-methylamine (see preparation of intermediates) (12.22 g, 50.29 mmol) and the reaction mixture is stirred at 50° C. The reaction is shown to be complete by LCMS after 5 days. The solvent is removed in vacuo and replaced with MeOH (250 mL). The resulting precipitate is filtered off and dried to give the title compound. $^1H$ nmr ($d_6$-DMSO, 400 MHz); 8.20(br s, 1H), 7.25(d, 4H), 6.90(d, 4H), 3.75(s, 6H), 3.15(m, 1H), MS (ES+) m/e 396 ($MH^+$).

(1S,4R)-4-(6-{[Bis-(4-methoxy-phenyl)-methyl]-amino}-2-chloro-purin-9-yl)-cyclopent-2-eno]

Bis-(4-methoxy-phenyl)-methyl]-(2-chloro-9H-purin-6-yl)-amine (13 g, 32.87 mmol) is placed in an oven-dried flask under an atmosphere of argon. Dry deoxygenated THF (100 ml) and dry DMSO (2 ml) are added and the suspension is cooled on an ice-bath. Sodium hydride 95% (0.79 g, 32.87 mmol) is then slowly added and the solution is stirred at room temperature for 30 minutes. (1S,4R)-cis 4-Acetoxy-2-cyclopenten-1-ol (4.9 g. 34.5 mmol) and triphenylphosphine (1.36 g, 5.17 mmol) are placed in an oven-dried flask under an atmosphere of argon. Dry deoxygenated THF (50 ml) is added. This solution is added to the anion solution via syringe. Tetrakis(triphenylphosphine)palladium(0) (2 g, 1.73 mmol) is then added and the mixture is stirred at 50° C. The reaction is shown to be complete by LCMS after 2 hours. The reaction mixture is allowed tco cool and the solvent is removed in vacuo. The residue is taken up in methanol (50 ml) and the resulting precipitate is filtered off and dried to give the title compound. $^1H$ nmr ($CDCl_3$, 400 MHz); 9.10(m, 1H), 8.10(m, 1H), 7.30(d, 4H), 6.90(d, 4H), 6.55(d, 1H), 6.20(m, 1H), 5.95(m, 1H), 5.40(m, 1H), 5.30(d, 1H), 4.70(m, 1H), 3.70(s, 6H), 2.90(m, 1H), 1.70(m, 1H), MS ($ES^+$) m/e 478 ($MH^+$).

Carbonic acid (1S,4R)-4-(6-{[bis- (4-methoxy-phenyl)-methyl]-amino}-2-chloro-purin-9-yl)-cyclopent-2-enyl ester ethyl ester (1S,4R)-4-(6-{[Bis-(4-methoxy-phenyl)-methyl]-amino}-2-chloro-purin-9-yl)-cyclopent-2-enol (8.00 g, 16.75 mmol) is placed in an oven-dried flask under an atmosphere of argon. Dry pyridine (80 ml) is added followed by diisopropylamine (16 ml). A catalytic amount of DMAP is added followed by 3-oxy-benzotriazole-1-carboxylic acid ethyl ester (6.94 g, 33.50 mmol, see preparation of intermediates). The reaction mixture is stirred at room temperature. The reaction is shown to be complete by TLC after 18 hours. The solvent is removed in vacuo and the residue is partitioned between ethyl acetate (500 ml) and 2M HCl (200 ml). The organic layer is washed with water (150 ml) and brine (150 ml), dried over $MgSO_4$, filtered and the solvent is removed in vacuo. The title compound is obtained after purification by flash column chromatography (silica, dichloromethane/methanol 50:1). $^1$H nmr ($CDCl_3$, 400 MHz); 7.80(s, 1H), 7.25(d of d, 4H), 6.85(d of d, 4H), 6.65(m, 1H), 6.50(m, 1H), 6.35(m, 1H), 6.15(m, 1H), 5.65(m, 2H), 4.25(q, 2H), 3.80(s, 6H), 3.10(m, 1H), 1.95(m, 1H), 1.35(t, 3H).

[Bis-(4-methoxy-phenyl)-methyl]-{2-chloro-9-[(1R, 4S)-4-(di-Boc-amino)-cyclopent-2-enyl]-9H-purin-6-yl}-amine Carbonic acid (1S,4R)-4-(6-{[bis-(4-methoxy-phenyl)-methyl]-amino}-2-chloro-purin-9-yl)-cyclopent-2-enyl ester ethyl ester (2.00 g, 3.64 mmol), di-t-butyl iminodicarboxylate (0.87 g, 4.00 mmol) and triphenylphosphine (0.14 g, 0.55 mmol) are placed in an oven-dried flask under an atmosphere of argon. Dry deoxygenated THF (20 ml) is added followed by tetrakis(triphenylphosphine)palladium(0) (0.21 g, 0.18 mmol) and the mixture is stirred at room temperature. The reaction is shown to be complete by LCMS after 3 hours. The solvent is removed in vacuo and the title compound is obtained after purification by flash column chromatography (silica, iso-hexane/ethyl acetate 4:1). $^1$H nmr ($CDCl_3$, 400 MHz); 8.20(s, 1H), 7.25(d, 4H), 6.85(d, 4H), 6.60(m, 1H), 6.35(m, 1H), 6.10(m, 1H), 5.80(m, 1H), 5.65(m, 1H), 5.35(m, 1H), 3.80(s, 6H), 3.15(m, 1H), 2.10(m, 1H), 1.55(s, 18H).

(1R,2S,3R,5S)-3-(6-{[Bis-(4-methoxy-phenyl)-methyl]-amino}-2-chloro-purin-9-yl)-5-(di-Boc-amino)-cyclopentane-1,2-diol

[Bis-(4-methoxy-phenyl)-methyl]-{2-chloro-9-[(1R,4S)-4-(di-Boc-amino)-cyclopent-2-enyl]-9H-purin-6-yl}-amine (0.75 g, 1.11 mmol) is dissolved in THF (15 ml). N-Methylmorpholine N-oxide (0.26 g, 2.22 mmol) is added followed by osmium tetroxide (1.5 ml, 4% in water). The reaction mixture is stirred at room temperature. The reaction is shown to be complete by LCMS after 18 hours. The solvent is removed in vacuo and the title compound is obtained after purification by flash column chromatography (silica, dichloromethane/methanol 50:1). $^1$H nmr ($CDCl_3$, 400 MHz); 7.75 (s, 1H), 7.25(m, 4H), 6.85(m, 4H), 6.60(m, 2H), 5.70(m, 1H), 4.70(m, 2H), 4.60(m, 1H), 4.45(m, 1H), 3.80(s, 6H), 3.70(m, 1H), 3.40(m, 1H), 3.25(m, 1H), 2.65(m, 1H), 2.50(m, 1H), 1.55(s, 18H).

(1S,2R,3S,5R)-3-Amino-5-(6-amino-2-chloro-purin-9-yl)-cyclopentane-1,2-diol trifluoroacetate (1R,2S,3R,5S)-3-(6-{[Bis-(4-methoxy-phenyl)-methyl]-amino}-2-chloro-purin-9-yl)-5-(di-Boc-amino)-cyclopentane-1,2-diol (600 mg, 0.84 mmol) is dissolved in dichloromethane (4 ml). TFA (2 ml) is added and the reaction mixture is stirred at room temperature. The reaction is shown to be complete by LCMS after 18 hours. The solvent is removed in vacuo and the title compound is obtained after purification by reverse phase column chromatography (Isolute™ C18, 0-100% acetonitrile in water—0.1% TFA). $^1$H nmr (MeOD, 400 MHz); 8.10(s, 1H), 4.80(m, 1H), 4.60(m, 1H), 4.30(m, 1H), 3.60(m, 1H), 2.85(m, 1H), 2.30(m, 1H). MS (ES+) m/e 285 ($MH^+$).

N-[(1S,2R,3S,4R)-4-(6-Amino-2-chloro-purin-9-yl)-2,3-dihydroxy-cyclopentyl]-methanesulfonamide trifluoroacetate (1S,2R,3S,5R)-3-Amino-5-(6-amino-2-chloro-purin-9-yl)-cyclopentane-1,2-diol trifluoroacetate (20 mg, 39 μmol) and diisopropylethylamine (25 mg, 190 μmol) are placed in a flask with dry THF (1 ml). Mesyl chloride (4.5 mg, 39 μmol) is added and the reaction mixture is stirred at room temperature. The reaction is shown to be complete by LCMS after 3 hours. The solvent is removed in vacuo and the title compound is obtained after purification by reverse phase column chromatography (Isolute™ C18, 0-100% acetonitrile in water—0.1% TFA). MS (ES+) m/e 363 ($MH^+$).

Example 2

N-[(1S,2R,3S,4R)-4-(6-Amino-2-phenethylamino-purin-9-yl)-2,3-dihydroxy-cvclcpentyl]-propionamide trifluoroacetate N-[(1S2R,3S,4R)-4-(6-Amino-2-chloro-purin-9-yl)-2,3-dihydroxy-cyclopentyl]-propionamide trifluoroacetate (1S,2R,3S,5R)-3-Amino-5-(6-amino-2-chloro-purin-9-yl)-cyclopentane-1,2-diol trifluoroacetate (intermediate for preparing Example 1) (20 mg, 39 μmol) and diisopropylethylamine (25 mg, 190 μmol) are placed in a flask with dry THF (1 ml). Propionyl chloride (3.6 mg, 39 μmol) is added and the reaction mixture is stirred at room temperature. The reaction is shown to be complete by LCMS after 3 hours. The solvent is removed in vacuo and the title compound is obtained, which can be purified by reverse phase column chromatography (Isolute™ C18, 0-100% acetonitrile in water—0.1% TFA). $^1$H nmr (MeOD, 400 MHz); 8.10(s, 1H), 4.75(m, 1H), 4.60(m, 1H), 4.20(m, 1H), 4.00(m, 1H), 3.75(m, 1H), 3.25(m, 1H), 2.85(m, 1H), 2.40(q, 2H), 2.10(m, 1H), 1.20(t, 3H), MS (ES+) m/e 341 ($MH^+$).

N-[(1S2R,3S,4R)-4-(6-Amino-2-phenethylamino-purin-9-yl)-2,3-dihydroxy-cyclopentyl]-propionamide trifluoroacetate N-[(1S,2R,3S,4R)-4-(6-Amino-2-chloro-purin-9-yl)-2,3-dihydroxy-cyclopentyl]-propionamide obtained directly in the previous step without purification (10.6 mg, 31 μmol) and phenethylamine (19 mg, 150 μmol) are placed in a 0.5-2.5 ml microwave vial. Dichlorobenzene (0.5 ml) is added and the reaction mixture is microwaved in a Personal Chemistry Emrys™ Optimizer microwave reactor at 240° C. The reaction is shown to be complete by Liquid Chromatography-Mass Spectrometry (LCMS) after 1 hour. The solvent is removed in vacuo (and the title compound is obtained after purification by reverse phase column chromatography (Isolute™ C18, 0-100% acetonitrile in water—0.1% TFA). $^1$H nmr (MeOD, 400 MHz); 8.05 (s, 1H), 7.40-715(m, 5H), 4.70(m, 1H), 4.55(m, 1H), 4.10(m, 2H), 3.70(m, 4H), 3.15(m, 1H), 2.95(m, 4H), 2.70(m, 1H), 2.20(m, 2H), 2.00(m, 1H), 1.20(t, 3H), MS (ES+) m/e 426 ($MH^+$).

Example 3

N-[(1S2R,3S,4R)-4-(6-Amino-2-hex-1-ynyl-purin-9-yl)-2,3-dihydroxy-cyclopentyl]-propionamide trifluoroacetate N-[(1S,2R,3S,4R)-4-(6-Amino-2-chloro-purin-9-yl)-2,3-dihydroxy-cyclopentyl]-propionamide (10.6 mg, 31 μmol), 1-hexyne (25.4 mg, 310 μmol), copper (I) iodide (1.5 mg, 7.75 μmol), dichlorobis(triphenylphosphine)palladium(II) (5.5 mg, 7.7 μmol), triphenylphosphine (4.0 mg, 15.5 μmol), diethylamine (0.4 mL) and DMF (0.2 mL) are placed in a 0.5-2.5 mL microwave vial. The reaction mixture is microwaved in a Personal Chemistry Emrys™ Optimizer microwave reactor at 120° C. The reaction is shown to be complete by LCMS after 1 hour. The solvent is removed in vacuo and the title compound is obtained after purification by reverse phase column chromatography (Isolute™ C18, 0-100% acetonitrile in water—0.1% TFA.). MS (ES+) m/e 387 ($MH^+$).

Example 4

N-{(1S,2R,3S,4R)-4-[2-Chloro-6-(2,2-diphenyl-ethylamino)-purin-9-yl]-2,3-dihydroxy-cyclopentyl}-propionamide (1S,4R)-4-(2,6-Dichloro-purin-9-yl)-cyclopent-2-enol 2,6-Dichloropurine (10 g, 52.90 mmol), (1S,4R)-cis 4-acetoxy-2-cyclopenten-1-ol (10 g. 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 ml) is added and the reaction mixture is stirred gently for 5 minutes. Triethylamine (20 ml) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, dichloromethane/methanol 25:1). $^1$H nmr ($CDCl_3$, 400 MHz); 8.30(s, 1H), 6.40(m, 1H), 5.90(m, 1H), 5.50(m, 1H), 4.95(m, 1H), 3.05(m, 1H), 2.10(m, 1H), MS (ES+) m/e 271 ($MH^+$).

Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol (9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40-C and the reaction mixture is stirred at room temperature. The reaction is shown to be complete by LCMS after 1 hour. The solvent is removed in vacuo and the residue is partitioned between dichloromethane (200 mL) and water (200 mL). The organic layer is washed with water (150 ml) and brine (150 ml), dried over $MgSO_4$, filtered and the solvent is removed in vacuo. The title compound is obtained after crystallisation from methanol. $^1$H nmr ($CDCl_3$, 400 MHz); 8.20(s, 1H), 6.45(m, 1H), 6.25(m, 1H), 5.75(m, 1H), 5.70(m, 1H), 4.25(q, 2H), 3.20(m, 1H), 2.05(m, 1H), 1.35(t, 3H), MS (E+) m/e 343 ($MH^+$).

Di-Boc-[(1S,4R)-4-(2,6-dichloro-purin-9-yl)-cyclopent-2-enyl]-amine

Carbonic acid (1S,4R)-4-(2,6-dichloro-purin-9-yl)-cyclopent-2-enyl ester ethyl ester (2.5 g, 7.29 mmol), di-t-butyl iminodicarboxylate (1.74 g, 8.02 mmol), tris(dibenzylideneacetone)-dipalladium(0) (0.33 g, 0.36 mmol) and triphenylphosphine (0.29 g, 1.09 mmol) are placed ira an oven-dried flask under an atmosphere of argon. Dry deoxygenated THF (30 ml) is added and the reaction mixture is stirred at room temperature. The reaction is shown to be complete by LCMS after 3 hours. The solvent is removed in vacuo and the title compound is obtained after purification by flash column chromatography (silica, ethyl acetate/isohexane 4:1) $^1$H nmr ($CDCl_3$, 400 MHz); 8.70(s, 1H), 6.20(m, 1H), 5.85(m, 1H), 5.80(m, 1H), 5.40(m, 1H), 3.20(m, 1H), 2.15(m, 1H), 1.55(s, 18H), MS ($ES^+$) m/e 470 ($MH^+$).

(1S,2R,3S,5R)-3-(Di-Boc-amino)-5-(2,6-dichloro-purin-9-yl)-cyclopentane-1,2-diol The title compound is prepared from di-Boc-[(1S,4R)-4-(2,6-dichloro-purin-9-yl)-cyclopent-2-enyl]-amine using a procedure analogous to that use to prepare (1R,2S,3R,5S)-3-(6-{[bis-(4-methoxy-phenyl)-methyl]-amino}-2-chloro-purin-9-yl)-5-(di-Boc-amino)-cyclopentane-1,2-diol. $^1$H nmr ($CDCl_3$, 400 MHz); 8.35(s, 1H), 4.80(m, 1H), 4.70(m, 1H), 4.50(m, 1H), 3.85(m, 1H), 3.75(m, 1H), 3.10(m, 1H), 2.75(m, 1H), 2.55(m, 1H), 1.55(s, 18H), MS (ES+) m/e 504 ($MH^+$).

(1S,2R,3S,5R)-3-Amino-5-(2,6-dichloro-purin-9-yl)-cyclopentane-1,2-diol trifluoroacetate The title compound is prepared from (1S,2R,3S,5R)-3-(di-Boc-amino)-5-(2,6-dichloro-purin-9-yl)-cyclopentane-1,2-diol using a procedure analogous to that used to prepare (1S,2R,3S,5R)-3-amino-5-(6-amino-2-chloro-purin-9-yl)-cyclopentane-1,2-diol trifluoroacetate in Example 1. MS (ES+) m/e 304 ($MH^+$).

N-[(1S,2R,3S,4R)-4-(2,6-Dichloro-purin-9-yl)-2,3-dihydroxy-cyclopentyl]-propionamide The title compound is prepared from (1S,2R,3S,5R)-3-amino-5-(2,6-dichloro-purin-9-yl)-cyclopentane-1,2-diol trifluoroacetate and propionyl chloride using a procedure analogous to that used to prepare N-[(1S,2R,3S,4R)-4-(6-amino-2-chloro-purin-9-yl)-2,3-dihydroxy-cyclopentyl]-propionamide trifluoroacetate in Example 2. MS (ES+) m/e 360 ($MH^+$).

N-[(1S,2R,3S,4R)-4-[2-Chloro-6-(2,2-diphenyl-ethylamino)-purin-9-yl]-2,3-dihydroxy-cyclopentyl]-propionamide N-[(1S,2R,3S,4R)-4-(2,6-Dichloro-purin-9-yl)-2,3-dihydroxy-cyclopentyl]-propionamide (160) mg, 0.44 mmol) is dissolved in THF (5 ml) under an atmosphere of argon. Diisopropylamine (69 mg, 0.53 mmol) is added followed by 2,2-diphenylethylamine (96 mg, 0.49 mmol) and the reaction mixture is stirred at 50° C. The reaction is shown to be complete by LCMS after 2 hours. The solvent is removed in vacuo and the title compound is obtained after purification by reverse phase column chromatography (Isolute™ C18, 0-100% acetonitrile in water—0.1% TFA).). $^1$H nmr (MeOD, 400 MHz); 8.00(s, 1H), 7.40-7.15(m, 10H), 4.75(m, 1H), 4.60(m, 1H), 4.50(m, 1H), 4.20(m, 3H), 3.95(m, 1H), 2.85(m, 1H), 2.40(q, 2H), 2.10(m, 1H), 1.20(t, 3H), MS (ES+) m/e 521 ($MH^+$).

The final compound of Example 4 may also be prepared using the following process:

{2-Chloro-9-[(1R,4S)-4-(di-Boc-amino)-cyclopent-2-enyl]-9H-purin-6-yl}-(2,2-diphenyl-ethyl)amine (1S,2R,3S,5R)-3-(Di-Boc-amino)-5-(2,6-dichloro-purin-9-yl)-cyclopentane-1,2-diol (13.0 g, 27.66 mmol) is dissolved in THF (250 mil) under an atmosphere of argon. Diisopropylamine (4.28 g, 33.19 mmol) is added followed by 2,2-diphenylethylamine (6.0 g, 30.43 mmol) and the reaction mixture is stirred at 50° C. The reaction is shown to be complete by LCMS after 18 hours. The solvent is removed in vacuo and the reaction mixture is partitioned between dichloromethane (250 ml) and 0.1M HCl (250 ml). The organic layer is washed with water (200 ml) and brine (200 ml), dried over $MgSO_4$, filtered and the solvent is removed in vacuo to give the title compound. $^1$H nmr ($CDCl_3$, 400 MHz); 8.05(s, 1H), 7.30-7.10(m, 10H), 6.00(m, 1H), 5.70(m, 2H), 5.60(m, 1H), 5.20(m, 1H), 4.30(m, 1H), 4.20(m, 1H), 3.65(m, 1H), 3.05(m, 1H), 2.00(m, 1H), 1.70(m, 1H), 1.40(s, 18H), MS (ES+) m/e 631 ($MH^+$).

(1R,2S,3R,5S)-3-[2-Chloro-6-(2,2-diphenyl-ethylamino)-purin-9-yl]-5-(di-Boc-amino)-cyclopentane-1,2-diol The title compound is prepared from {2-chloro-9-[(1R,4S)-4-(di-Boc-amino)-cyclopent-2-enyl]-9H-purin-6-yl}-(2,2-diphenyl-ethyl)-amine using a procedure analogous to that of Prep. 11. $^1$H nmr (MeOD, 400 MHz); 8.05(s, 1H), 7.35-7.15(m, 10H), 4.70-4.55(m, 4H), 4.50(m, 1H), 4.35(m, 1H), 4.20(m, 2H), 2.55(m, 1H), 2.45(m, 1H), 1.60(s, 18H).

(1S,2R,3S,5R)-3-Amino-5-[2-chloro-6-(2,2-diphenyl-ethylamino)-purin-9-yl]-cyclopentane-1,2-diol trifluoroacetate (1R,2S,3R,5S)-3-[2-Chloro-6-(2,2-diphenyl-ethylamino)-purin-9-yl]-5-(di-Boc-amino)-cyclopentane-1,2-diol (10.3 g, 15.50 mmol) is dissolved in dichloromethane (50 ml). TFA (25 ml) is added and the reaction mixture is stirred at room temperature. The reaction is shown to be complete by LCMS after 2 hours. The solvent is removed in vacuo to give the title compound. $^1$H nmr (MeOD, 400 MHz); 7.90(s, 1H), 7.30-7.10(m, 10H), 4.65(m, 1H), 4.50 (m, 1H), 4.40(m, 1H), 4.20(m, 1H), 4.10(m, 2H), 3.50(m, 1H), 2.75(m, 1H), 2.15(m, 1H), MS (ES+) m/e 465 ($MH^+$).

N-{(1S,2R,3S,4R)-4-[2-Chloro-6-(2,2-diphenyl-ethylamino)-purin-9-yl]-2,3-dihydroxy-cyclopentyl}-propionamide (1S,2R,3S,5R)-3-Amino-5-[2-chloro-6-(2,2-diphenyl-ethylamino)-purin-9-yl]-cyclopentane-1,2-diol trifluoroacetate (9.50 g, 16.42 mmol) and diisopropylethylamine (6.36 g, 49.27 mmol) are placed in a flask with dry THF (150 ml). Propionyl chloride (1.52 g, 16.42 mmol) is added dropwise and the reaction mixture is stirred at room temperature. The reaction is shown to be complete by LCMS after 1 hour. The solvent is removed in vacuo and the residue is partitioned between dichloromethane (250 ml) and water (250 ml). The organic layer is washed with water (200 ml) and brine (200 ml), dried over $MgSO_4$, filtered and the solvent is removed in vacuo. The solid is recrystallised from 1,2-dichloroethane to give the title compound. $^1$H nmr (MeOD, 400 MHz); 8.00(s, 1H), 7.40-7.15(m, 10H), 4.75(m, 1H), 4.60(m, 1H), 4.50(m, 1H), 4.20(m, 3H), 3.95(m, 1H), 2.85(m, 1H), 2.40(q, 2H), 2.10(m, 1H), 1.20(t, 3H), MS (ES+) m/e 521 ($MH^+$).

Example 5

N-{(1S,2R,3S,4R-4-[2-(4-Amino-cyclohexylamino)-6-(2,2-diphenyl-ethylamino)-purin-9-yl]-2,3-dihydroxy-cyclopentyl}-propionamide trifluoroacetate N-{(1S,2R,3S,4R)-4-[2-Chloro-6-(2,2-diphenyl-ethylamino)-purin-9-yl]-2,3-dihydroxy-cyclopentyl}-propionamide (final compound of Example 4) is reacted with cyclohexane-1,4-diamine using a procedure analogous to that used to prepare the compound of Example 2. MS (ES+) m/e 599 ($MH^+$).

The free-base is formed as follows: N-{(1S,2R,3S,4R)-4-[2-(4-Amino-cyclohexylamino)-6-(2,2-diphenyl-ethylamino)-purin-9-yl]-2,3-dihydroxy-cyclopentyl}-propionamide trifluoroacetate (300 mg, 0.50 mmol) is loaded onto DODWEX® 50WX2-200 ion exchange resin (pre-washed with water). The resin is eluted with water until neutral pH and then with methanol: ammonia 0.880 (1:1) to elute the free base.). $^1$H nmr (MeOD, 400 MHz); 7.65(s, 1H), 7.40-7.20(m, 10H), 4.60(m, 1H), 4.50(m, 2H), 4.20(m, 3H), 4.05(m, 1H), 3.70(m, 1H), 2.70(m, 2H), 2.30(q, 2H), 2.20(m, 2H), 2.00(m, 1H), 1.95(m, 2H), 1.30(m, 4H), 1.20(t, 3H), MS (ES+) m/e 599 ($MH^+$).

Example 6

N-{(1S,2R,3S,4R)-4-[6-(2,2-Diphenyl-ethylamino)-2-hex-1-ynyl-purin-9-yl]-2,3-dihydroxy-cyclopentyl}-propionamide The title compound is prepared from N-[(1S,2R,3S,4R)-4-(2,6-Dichloro-purin-9-yl)-2,3-dihydroxy-cyclopentyl]-propionamide using a procedure analogous to that used to prepare the compound of Example 3.

Example 7

N-{(1S,2R,3 S,4R)-4-{6-(2,2-Diphenyl-ethylamino)-2-[2-(1H-imidazol-4-yl)-ethylamino]-purin-9-yl}-2,3-dihydroxy-cyclopentyl}-propionamide This compound is prepared from N-[(1S,2R,3S,4R)-4-(2,6-Dichloro-purin-9-yl)-2,3-dihydroxy-cyclopentyl]-propionamide using histamine in a procedure analogous to that used to prepare the compound of Example 5.

Example 8

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-propionamide The title compound is prepared using N-(aminoethyl)piperidine in a procedure analogous to that used to prepare the compound of Example 5.

Example 9

N-((1S,2R,3S,4R)-4-{6-(2,2-Diphenyl-ethylamino)-2-[2-(1-methyl-1H-imidazol-4-yl)-ethylamino]-purin-9-yl}-2,3-dihydroxy-cyclopentyl)-propionamide trifluoroacetate N-{(1S,2R,3S,4R)-4-[2-Chloro-6-(2,2-diphenyl-ethylamino)-purin-9-yl]-2,3-dihydroxy-cyclopentyl}-propionamide (compound of Example 4) (20 mg, 38 μmol) and 2-(1-methyl-1H-imidazol-4-yl)-ethylamine (24 mg, 190 μmol) are placed in a 0.5-2.5 ml microwave vial. Dichlorobenzene (0.5 ml) is added and the reaction mixture is heated using microwave radiation in a Personal Chemistry Emrys™ Optimizer microwave reactor at 200° C. The reaction is shown to be complete by LCMS after 2 hours. The solvent is removed in vacuo and the title compound is obtained after purification by reverse phase column chromatography (Isolute™ C18, 0-100% acetonitrile in water—0.1% TFA). $^1$H nmr (MeOD, 400 MHz); *0.80(s, 1H), 8.15(s, 1H), 7.40-7.20(m, 1H), 4.75 (m, 2H), 4.50(m, 2H), 4.30(m, 1H), 4.10(m, 2H), 3.85(s, 3H), 3.75(m, 21H), 3.10(m, 3H), 2.70(m, 1H), 2.25(q, 2H), 1.95 (m, 1H), 1.30(m, 4H), 1.15(t, 3H), MS (ES+) m/e 610 (MH$^+$).

Example 10

N-((1S,2R,3S,4R)-4-{6-(2,2-Diphenyl-ethylamino)-2-[2-(1-ethyl-1H-imidazol-4-yl)-ethylamino]-purin-9-yl}-2-dihydroxy-cyclopentyl)-propionamide This compound is prepared from N-{(1S,2R,3S,4R)-4-[2-chloro-6-(2,2-diphenyl-ethylamino)-purin-9-yl]-2,3-dihydroxy-cyclopentyl}-propionamide (compound of Example 4) and 2-(1-ethyl-1H-imidazol-4-yl)-ethylamine using a procedure analogous to that of Example 21. MS (ES+) m/e 624 (MH$^+$).

Example 11

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-propionamide This compound is prepared from N-{(1S,2R,3S,4R)-4-[2-chloro-6-(2,2-diphenyl-ethylamino)-purin-9-yl]-2,3-dihydroxy-cyclopentyl}-propionamide (compound of Example 4) and 2-(1-isopropyl-1H-imidazol-4-yl)-ethylamine using a procedure analogous to that of Example 9 for the desired salt. MS (ES+) m/e 638 (MH$^+$).

Examples 12 and 13

Cyclopropanecarboxylic acid {(1S,2R,3S,4R)-4-[2-chloro-6-(2,2-diphenyl-ethylamino)-purin-9-yl]-2,3-dihydroxy-cyclopentyl}-amide and N-{(1S,2R,3S,4R)-4-[2-Chloro-6-(2,2-diphenyl-ethylamino)-purin-9-yl]-2,3-dihydroxy-cyclopentyl}-butyramide are prepared using a procedure analogous to that of Example 4 in which propionyl chloride is replaces with the appropriate acylating agent.

Example 14

N-{(1S,2R,3S,4R)-4-[2-Chloro-6-(1-ethyl-propylamino)-purin-9-yl]-2,3-dihydroxy-cyclopentyl}-propionamide

[(1S,4R)-4-(2,6-Dichloro-purin-9-yl)-cyclopent-2-enyl]-propionyl-carbamic acid tert-butyl ester The title compound is prepared from carbonic acid (1S,4R)-4-(2,6-dichloro-purin-9-yl)-cyclopent-2-enyl ester ethyl ester (an intermediate for preparing the compound of Example 4) and propionyl-carbamic acid tert-butyl ester (see preparation of intermediates) using a procedure analogous to that of di-Boc-[(1S,4R)-4-(2,6-dichloro-purin-9-yl)-cyclopent-2-enyl]-amine (another intermediate for preparing the compound of Example 4). $^1$H nmr ($CDCl_3$, 400 MHz); 8.70(s, 1H), 6.15(m, 1H), 5.85(m, 1H), 5.80(m, 1H), 5.60(m, 1H), 3.15(m, 1H), 2.75(q, 2H), 2.10(m, 1H), 1.55(s, 9H), 1.15(t, 3H), MS (ES+) m/e 426 (MH$^+$).

{(1S,4R)-4-[2-Chloro-6-(1-ethyl-propylamino)-purin-9-yl]-cyclopent-2-enyl}-propionyl-carbamic acid tert-butyl ester

[(1S,4R)-4-(2,6-Dichloro-purin-9-yl)-cyclopent-2-enyl]-propionyl-carbamic acid tert-butyl ester (700 mg, 1.64 mmol) is dissolved in THF (15 ml) under an atmosphere of argon. 3-Pentyl-amine (315 mg, 3.61 mmol) is added and the reaction mixture is stirred at 50° C. The reaction is shown to be complete by LCMS after 18 hours. The reaction mixture is partitioned between dichloromethane (50 ml) and 0.1M HCl (50 ml). The organic layer is washed with water (20 ml) and brine (20 ml), dried over $MgSO_4$, filtered and the solvent is removed in vacuo to give the title compound. $^1$H nmr ($CDCl_3$, 400 MHz); 8.10(s, 1H), 6.00(m, 1H), 5.70(m, 1H), 5.60(m, 2H), 5.45(m, 1H), 4.20(m, 1H), 3.65(m, 1H), 3.00(m, 1H), 2.65(m, 3H), 1.95(m, 1H), 1.60(m, 3H), 1.45(s, 9H), 1.10(m, 4H), 0.85(t, 6H), MS (ES+) m/e 477 (MH$^+$).

{(1S,2R,3S,4R)-4-[2-Chloro-6-(1-ethyl-propylamino)-purin-9-yl]-2,3-dihydroxy-cyclopentyl}-propionyl-carbamic acid tert-butyl ester The title compound is prepared from {(1S,4R)-4-[2-chloro-6-(1-ethyl-propylamino)-purin-9-yl]-cyclopent-2-enyl}-propionyl-carbamic acid tert-butyl ester using a procedure analogous to that of (1R,2S,3R,5S)-3-(6-{[bis-(4-methoxy-phenyl)-methyl]-amino}-2-chloro-purin-9-yl)-5-(di-Boc-amino)-cyclopentane-1,2-diol (see Example 1). Purification by reverse phase column chromatography (Isolute™ C18, 0-100% acetonitrile in water—0.1% TFA). $^1$H nmr (MeOD, 400 MHz); 8.10(s, 1H), 4.80(m, 1H), 4.65(m, 1H), 4.35(m, 1H), 4.20(m, 1H), 2.85(m, 2H), 2.60(m, 1H), 2.35(m, 1H), 1.70(m, 2H), 1.65(s, 9H), 1.60(m, 2H), 1.15(t, 3H), 0.95(t, 6H).

N-{(1S,2R,3S,4R)-4-[2-Chloro-6-(1-ethyl-propylamino)-purin-9-yl]-2,3-dihydroxy-cyclopentyl}-propionamide {(1S,2R,3S,4R)-4-[2-Chloro-6-(1-ethyl-propylamino)-purin-9-yl]-2,3-dihydroxy-cyclopentyl}-propionyl-carbamic acid tert-butyl ester (300 mg, 0.59 mmol) is dissolved in dichloromethane (5 ml). TFA (2 ml) is added and the reaction mixture is stirred at room temperature. The reaction is shown to be complete by LCMS after 1 hour. The solvent is removed in vacuo and the residue is partitioned between dichloromethane (50 ml) and saturated $NaHCO_3$ (50 ml). The organic layer is washed with water (20 ml) and brine (20 ml), dried over $MgSO_4$, filtered and the solvent is removed in vacuo to give the title compound. $^1$H nmr (MeOD, 400 MHz); 8.05(s, 1H), 4.75(m, 1H), 4.60(m, 1H), 4.20(m, 2H), 4.00(m, 1H), 2.90(m, 1H), 2.40(q, 2H), 2.10(m, 1H), 1.70(m, 2H), 1.60(m, 2H), 1.20(t, 3H), 0.95(t, 6H), MS (ES+) mine 411 (MH$^+$).

Example 15

N-{(1S,2R,3S,4R)-4-[6-(1-ethyl-propylamino)-2-hex-1-ynyl-purin-9-yl]-2,3-dihydroxy-cyclopentyl}-propionamide This compound is prepared from {(1S,2R,3S,4R)-4-[2-chloro-6-(1-ethyl-propylamino)-purin-9-yl]-2,3-dihydroxycyclopentyl}-propionyl-carbamic acid tert-butyl ester using a procedure analogous to that of Example 3.

Example 16

N-{(1S,2R,3S,4R)-4-[6-(2,2-Diphenyl-ethylamino)-2-((S)-1-hydroxymethyl-2-phenyl-ethylamino)-purin-9-yl]-2,3-dihydroxy-cyclopentyl}-propionamide N-{(1S,2R,3S,4R)-4-[2-Chloro-6-(2,2-diphenyl-ethylamino)-purin-9-yl]-2,3-dihydroxy-cyclopentyl}-propionamide (46.8 mg, 90 μmol) of Example 4, L-phenylalaninol (271 mg, 1.80 mmol) and sodium iodide (6.75 mg, 45 μmol) are placed in a 0.5-2.5 ml microwave vial. Acetonitrile (0.25 ml) and NMP (0.25 ml) are added and the reaction mixture is heated using microwave radiation in a Personal Chemistry Emrys™ Optimizer microwave reactor at 200° C. The reaction is shown to be complete by LCMS after 1 hour. The title compound is obtained after purification by reverse phase column chromatography (Isolute™ C18, 0-100% acetonitrile in water—0.1% TFA). MS (ES+) m/e 636 ($MH^+$).

Example 17

N-{(1S,2R,3S,4R)-4-[6-(1-Ethyl-propylamino)-2-(2-piperidin-1-yl-ethylamino)-purin-9-yl]-2,3-dihydroxy-cyclopentyl}-propionamide N-{(1S,2R,3S,4R)-4-[2-Chloro-6-(1-ethyl-propylamino)-purin-9-yl]-2,3-dihydroxy-cyclopentyl}-propionamide (the compound of Example 14) is reacted with 1-(2-aminoethyl)-piperidine to give the title compound using a procedure analogous to that of Example 9. MS (ES+) m/e 503 ($MH^+$).

Example 18

N-{(1S,2R,3S,4R)-4-[2-[2-(1-Ethyl-1H-imidazol-4-yl)-ethylamino]-6-(1-eihydroxy-cyclopentyl}-propionamide N-{(1S,2R,3S,4R)-4-[2-Chloro-6-(1-ethyl-propylamino)-purin-9-yl]-2,3-dihydroxy-cyclopentyl}-propionamide (the compound of Example 14) is reacted with 2-(1-ethyl-1H-imidazol-4-yl)-ethylamine to give the title compound using a procedure analogous to that of Example 9. MS (ES+) m/e 514 ($MH^+$).

Example 19

N-{(1S,2R,3S,4R)-4-[2-[2-(1-Isopropylthyl-1H-imidazol-4-yl)-ethylamino]-6-(1-eihydroxy-cyclopentyl}-propionamide N-{(1S,2R,3S,4R)-4-[2-Chloro-6-(1-ethyl-propylamino)-purin-9-yl]-2,3-dihydroxy-cyclopentyl}-propionamide (the compound of Example 14) is reacted with 2-(1-isopropyl-ethyl-1H-imidazol-4-yl)-ethylamine to give the title compound using a procedure analogous to that of Example 9. MS (ES+) m/e 528 ($MH^+$).

Example 20

N-{(1S,2R,3S,4R)-4-[2-(4-Amino-cyclohexylamino)-6-(1-ethyl-propylamino)-purin-9-yl]-2,3-dihydroxy-cyclopentyl}-propionamide N-{(1S,2R,3S,4R)-4-[2-Chloro-6-(1-ethyl-propylamino)-purin-9-yl]-2,3-dihydroxy-cyclopentyl}-propionamide (the compound of Example 14) is reacted with trans-1,4-diaminocyclohexane to give the title compound using a procedure analogous to that of Example 9. MS (ES+) m/e 489 ($MH^+$).

Example 21

N-((1S,2R,3S,4R)-4-{6-Amino-2-[2-(1-ethyl-1H-imidazol-4-yl)-ethylamino]-purin-9-yl}-2,3-dihydroxy-cyclopentyl)-isobutyramide N-[(1S,2R,3S,4R)-4-(6-Amino-2-chloro-purin-9-yl)-2,3-dihydroxy-cyclopentyl]-isobutyramide (1S,2R,3S,5R)-3-Amino-5-(6-amino-2-chloro-purin-9-yl)-cyclopentane-1,2-diol trifluoroacetate (an intermediate for preparing the compound of Example 1) is reacted with isopropionyl chloride to give the title compound using a procedure analogous to that of Example 1. MS (ES+) m/e 355 ($MH^+$).

N-((1S,2R,3S,4R)-4-{6-Amino-2-[2-(1-ethyl-1H-imidazol-4-yl)-ethylamino]-purin-9-yl}-2,3-dihydroxy-cyclopentyl)-isobutyramide N-[(1S,2R,3S,4R)-4-(6-Amino-2-chloro-purin-9-yl)-2,3-dihydroxy-cyclopentyl]-isobutyramide is reacted with and 2-(1-ethyl-1H-imidazol-4-yl)-ethylamine to give the title compound Lasing a procedure analogous to that of Example 9. MS (ES+) m/e 458 ($MH^+$).

Example 22

Cyclopropanecarboxylic acid ((1S,2R,3S,4R)-4-{6-(2,2-diphenyl-ethylamino)-2-[2-(1-isopropyl-1H-imidazol-4-yl)-ethylamino]-purin-9-yl}-2,3-dihydroxy-cyclopentyl)-amide trifluoroacetate (2-Chloro-9H-purin-6-yl)-(2,2-diphenyl-ethyl)-amine 2,6-Dichloropurine (20.00 g, 106 mmol) is dissolved in THF (250 ml) under an atmosphere of argon. Diisopropylamine (16.38 g, 127 mmol) is added followed by 2,2-diphenylethylamine (25.00 g, 127 mmol) and the reaction mixture is stirred at 50° C. The reaction is shown to be complete by LCMS after 6 hours. 50% of the solvent is removed in vacuo and replaced with MeOH. The resulting precipitate is filtered off and dried to give the title compound. $^1$H nmr ($d_6$-DMSO, 400 MHz); 8.05(br s, 1H), 7.35-7.10(m, 10H), 4.55(m, 1H), 4.10(rri, 2H), MS (ES+) m/e 350 ($MH^+$).

(1S,4R)-4-[2-Chloro-6-(2,2-diphenyl-ethylamino)-purin-9-yl]-cyclopent-2-enol (2-Chloro-9H-purin-6-yl)-(2,2-diphenyl-ethyl)-amine (12.92 g, 36.97 mmol) is placed in an oven-dried flask under an atmosphere of argon. Dry deoxygenated THF (100 ml) and dry DMSO (2 ml) are added and the suspension is cooled on an ice-bath. Sodium hydride 95% (0.89 g, 36.97 mmol) is then slowly added and the solution is stirred at room temperature for 30 minutes. (1S,4R)-cis 4-Acetoxy-2-cyclopenten-1-ol (5.00 g. 35.20 mmol) and triphenylphosphine (1.38 g, 5.28 mmol) are placed in an oven-dried flask under an atmosphere of argon. Dry deoxygenated THF (50 ml) is added. This solution is added to the anion solution. Tetrakis(triphenylphosphine)palladium(0) (2.03 g, 1.76 mmol) is added and the reaction mixture is stirred at 50° C. The reaction is shown to be complete by LCMS after 3 hours. The reaction mixture is allowed to cool and the solvent is removed in vacuo. The residue is taken up in dichloromethane (50 ml) and poured into vigorously stirring diethyl ether (300 ml). The precipitate is filtered off, the filtrate is taken and the solvent is removed in vacuo to give the title compound. $^1$H nmr ($CDCl_3$, 400 MHz); 7.65(m, 1H), 7.35-7.15(m, 10H), 6.35(m, 1H), 5.90(m, 1H), 5.80(m, 1H), 5.50(m, 1H), 5.25(d, 1H), 4.85(t, 1H), 4.35(t, 1H), 4.25(m, 2H), 2.95(m, 1H), 2.15(d, 1H), MS (ES+) m/e 432 ($MH^+$).

Carbonic acid (1S,4R)-4-[2-chloro-6-(2,2-diphenyl-ethylamino)-purin-9-yl]-cyclopent-2-enyl ester ethyl ester (1S,4R)-4-[2-Chloro-6-(2,2-diphenyl-ethylamino)-purin-9-yl]-cyclopent-2-enol (3.00 g, 6.95 mmol) is placed in an oven-dried flask under an atmosphere of argon. Dry THF (100 ml) is added followed by dry pyridine (1.10 g, 13.90 mmol). Ethyl chloroformate (3.02 g, 27.80 mmol) is added slowly and the reaction mixture is stirred at room temperature. The reaction is shown to be complete by TLC after 4 hours. The solvent is removed in vacuo and the residue is partitioned between dichloromethane (200 ml) and 10% citric acid (200 ml). The organic layer is washed with water (150 ml) and brine (150 ml), dried over $MgSO_4$, filtered and the solvent is removed in vacuo. The title compound is obtained after purification by flash column chromatography (silica, iso-hexane/ethyl acetate 2:1). $^1$H nmr ($CDCl_3$, 400 MHz); 7.70(br s, 1H), 7.35-7.15(m, 10H), 6.35(m, 1H), 6.15(m, 1H), 5.80(m, 1H), 5.65(m, 2H), 4.35(t, 1H), 4.25(m, 2H), 4.20(q, 2H), 3.10(m, 1H), 1.95(d, 1H), 1.30(t, 3H), MS (ES+) m/e 504 ($MH^+$).

9-((1R,4S)-4-(Bis-(tert-butyloxycarbonyl))-amino-cyclopent-2-enyl)-2-chloro-9H-purin-6-yl]-(2,2-diphenyl-ethyl)-amine Carbonic acid (1S,4R)-4-[2-chloro-6-(2,2-diphenyl-ethylamino)-purin-9-yl]-cyclopent-2-enyl ester ethyl ester (3.2 g, 6.3 mmol), di-t-butylimino-dicarboxylate (1.5 g, 7.0 mmol) and triphenyl phosphine (250 mg, 0.95 mmol) are dissolved in degassed THF (30 ml) under an argon atmosphere. Tris(dibenzylideneacetone)dipalladium (0) (291 mg, 0.32 mmol) is added and the mixture is heated at 40° C. for 1.5 hours. The reaction mixture is cooled to room temperature and the solvent is removed under reduced pressure. The residue is purified by column chromatography on silica gel eluting with a gradient system of ethyl acetate:iso-hexane (0:100 by volume) gradually changing to ethyl acetate:iso-hexane (20:80 by volume) to afford the title compound. LCMS (electrospray): m/z [$MH^+$] 631.32

(1S,2R,3S,5R)-3-(Bis-(tert-butyloxycarbonyl))-amino-5-[2-chloro-6-(2,2-diphenyl-ethylamino)-purin-9-yl]-cyclopentane-1,2-diol A solution of 9-((1R,4S)-4-(Bis-(tert-butyloxycarbonyl))-amino-cyclopent-2-enyl)-2-chloro-9H-purin-6-yl]-(2,2-diphenyl-ethyl)-amine (2.9 g, 4.6 mmol) in THF (60 ml) is treated with 4-methyl morpholine N-oxide (1.1 g, 9.3 mmol) and osmium tetroxide (4% solution in water) (6 ml) and the mixture is stirred at room temperature for 48 hours. The solvent is removed under reduced pressure and the residue is purified by column chromatography on silica gel eluting with a gradient system of methanol:dichloromethane (0:100 by volume) gradually changing to methanol:dichloromethane (4:96 by volume) to afford the title compound. LCMS (electrospray): m/z [$MH^+$] 665.34

(1S,2R,3S,5R-3-Amino-5-[2-chloro-6-(2,2-diphenyl-ethylamino)-purin-9-yl]-cyclopentane-1,2-diol hydrochloride (1S,2R,3S,5R)-3-(Bis-(tert-butyloxycarbonyl))-amino-5-[2-chloro-6-(2,2-diphenyl-ethylamino)-purin-9-yl]-cyclopentane-1,2-diol (1.9 g, 2.9 mmol) is dissolved in hydrogen chloride solution (4 M in 1,4-dioxane) (13 ml, 51.2 mmol) and the mixture is stirred at room temperature for 1 hour. The solvent is removed under reduced pressure and the residue is purified by reverse-phase chromatography eluting with a gradient system of acetonitrile (0.1% HCl):water (0.1% HCl) (0:100 by volume) gradually changing to acetonitrile (0.1% HCl):water (0.1% HCl) (100:0 by volume) to afford the title compound. LCMS (electrospray): m/z [$MH^+$] 465.20

Cyclopropanecarboxylic acid {(1S,2R,3S,4R)-4-[2-chloro-6-(2,2-diphenyl-ethylamino)-purin-9-yl]-2,3-dihydroxy-cyclopentyl}-amide A solution of (1S,2R,3S,5R)-3-Amino-5-[2-chloro-6-(2,2-diphenyl-ethylamino)-purin-9-yl]-cyclopentane-1,2-diol hydrochloride (200 mg, 0.4 mmol) in dry THF (2.5 ml) is treated with diisopropylethylamine (0.35 ml, 2 mmol) and cyclopropanecarboxylic acid chloride (0.036 ml, 0.4 mmol) and the mixture is stirred at room temperature for 48 hours. The solvent is removed under reduced pressure and the residue is purified by reverse-phase chromatography eluting with a gradient system of acetonitrile (0.1% TFA):water (0.1% TFA) (0:100 by volume) gradually changing to acetonitrile (0.1% TFA):water (0.1% TFA) (100:0 by volume) to afford the title compound. LCMS (electrospray): m/z [$MH^+$] 533.25 $^1$H nmr (MeOD, 400 MHz); 8.00(s, 1H), 7.40-7.25(m, 8H), 7.25-7.20(m, 2H), 4.75(m, 1H), 4.60(m, 1H), 4.50(m, 1H), 4.20(m, 2H), 4.00(m, 1H), 2.85(m, 1H), 2.10(m, 1H), 1.85(m, 1H), 0.95-0.80(m, 4H)

Cyclopropanecarboxylic acid ((1S,2R,3S,4R)-4-{6-(2,2-diphenyl-ethylamino)-2-[2-(1-isopropyl-1H-imidazol-4-yl)-ethylamino]-purin-9-yl}-2,3-dihydroxy-cyclopentyl)-amide trifluoroacetate A solution of cyclopropanecarboxylic acid {(1S,2R,3S,4R)-4-[2-chloro-6-(2,2-diphenyl-ethylamino]-purin-9-yl}-2,3-dihydroxy-cyclopentyl)-amide (20 mg, 0.04 mmol) in NMP:acetonitrile (1:1) (0.5 ml) is treated with 2-(1-isopropyl-1H-imidazol-4-yl)-ethylamine (30 mg, 0.2 mmol) and sodium iodide (6 mg, 0.04 mmol) and the mixture is heated at 200° C. for 30 minutes in a Personal Chemistry Emrys™ Optimizer microwave reactor. The reaction mixture is purified by reverse-phase chromatography eluting with a gradient system of acetonitrile (0.1% TFA):water (0.1% TFA) (0:100 by volume) gradually changing to acetonitrile (0.1% TFA):water (0.1% TFA) (100:0 by volume) to afford the title compound. LCMS (electrospray): m/z [$MH^+$] 650.22

Example 23

Cyclobutanecarboxylic acid ((1S,2R,3S,4R)-4-{6-(2,2-diphenyl-ethylamino)-Z-[2-(1-isopropyl-1H-imidazol-4-yl)-ethylamino]-purin-9-yl}-2,3-dihydroxy-cyclopentyl)-amide trifluoroacetate Cyclobutanecarboxylic acid {(1S,2R,3S,4R)-4-[2-chloro-6-(2,2-diphenyl-ethylamino)-purin-9-yl]-2,3-dihydroxy-cyclopentyl}-amide A solution of (1S,2R,3S,5R)-3-amino-5-[2-chloro-6-(2,2-diphenyl-ethylamino)-purin-9-yl]-cyclopentane-1,2-diol hydrochloride (an intermediate for preparing Example 22) (100 mg, 0.2 mmol) in dry THF (1 ml) is treated with diisopropylethylamine (0.17 ml, mmol) and cyclobutanecarboxylic acid chloride (0.023 ml, 0.2 mmol) and the mixture is stirred at room temperature for 48 hours. The solvent is removed under reduced pressure. The residue is purified by reverse-phase chromatography eluting with a gradient system of acetonitrile (0.1% TFA): water (0.1% TFA) (0:100 by volume) gradually changing to acetonitrile (0.1% TFA) water (0.1% TFA) (100:0 by volume) to afford the title compound (Slmg). LCMS (electrospray): m/z [$MH^+$] 547.26. $^1H$ nmr (MeOD, 400 MHz); 8.00(s, 1H), 7.40-7.25(m, 8H), 7.20-7.15 (m, 2H), 4.70(m, 1H), 4.50(m, 2H), 4.20(m, 2H), 3.95(m, 1H), 2.85(m, 1H), 2.30(m, 2H), 2.20(m, 2H), 2.05(m, 2H), 1.90(m, 1H)

Cyclobutanecarboxylic acid ((1S,2R,3S,4R)-4-{6-(2,2-diphenyl-ethylamino)-2-[2-(1-isopropyl-1H-imidazol-4-yl)-ethylamino]-purin-9-yl}-2,3-dihydroxy-cyclopentyl)-amide trifluoroacetate The title compound is prepared using a method that is analogous to that used to prepare the compound of Example 22 using cyclobutanecarboxylic acid {(1S,2R,3S,4R)-4-[2-chloro-6-(2,2-diphenyl-ethylamino)-purin-9-yl]-2,3-dihydroxycyclopentyl}-amide, 2-(1-isopropyl-1H-imidazol-4-yl)-ethylamine (see preparation of intermediates) (30 mg, 0.2 mmol) and sodium iodide (6 mg, 0.04 mmol). LCMS (electrospray): m/z [$MH^+$] 664.44

Example 24

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-butyramide trifluoroacetate N-{(1S,2R,3S,4R)-4-[2-Chloro-6-(2,2-diphenyl-ethylamino)-purin-9-yl]-2,3-dihydroxy-cyclopentyl}-butyramide The title compound is prepared by the same method as cyclobutanecarboxylic acid {(1S,2R,3S,4R)-4-[2-chloro-6-(2,2-diphenyl-ethylamino)-purin-9-yl]-2,3-dihydroxy-cyclopentyl}-amide from (1S,2R,3S,5R)-3-amino-5-[2-chloro-6-(2,2-diphenyl-ethylamino)-purin-9-yl]-cyclopentane-1,2-diol hydrochloride (an intermediate for preparing the compound of Example 22) and butyryl chloride to afford the title compound (48 mg). LCMS (electrospray): m/z [$MH^+$] 535.26. $^1H$ nmr (MeOD, 400 MHz); 8.00(s, 1H), 7.40-7.30 (m, 8H), 7.25-7.15(m, 2H), 4.75(m, 1H), 4.60(m, 1H), 4.50 (m, 1H), 4.20(m, 2H), 3.95(m, 1H), 2.85(m, 1H), 2.35(m, 2H), 2.05(m, 1H), 1.70(m, 2H), 1.00(m, 3H)

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-butyramide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-butyramide, 2-(1-isopropyl-1H-imidazol-4-yl)-ethylamine (see preparation of intermediates) (30 mg, 0.2 mmol) and sodium iodide (6 mg, 0.04 mmol). LCMS (electrospray): m/z [$MH^+$] 652.44

Example 25

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-isobutyramide trifluoroacetate N-{(1S,2R,3S,4R)-4-[2-Chloro-6-(2,2-diphenyl-ethylamino)-purin-9-yl]-2,3-dihydroxy-cyclopentyl}-isobutyramide The title compound is prepared by the same method as cyclobutanecarboxylic acid {(1S,2R,3S,4R)-4-[2-chloro-6-(2,2-diphenyl-ethylamino)-purin-9-yl]-2,3-dihydroxy-cyclopentyl}-amide from (1S,2R,3S,5R)-3-amino-5-[2-chloro-6-(2,2-diphenyl-ethylamino)-purin-9-yl]-cyclopentane-1,2-diol hydrochloride (an intermediate for preparing the compound of Example 22) and isobutyryl chloride to afford the title compound. LCMS (electrospray): m/z [$MH^+$] 535.26. $^1H$ nmr (MeOD, 400 MHz); 8.00(s, 1H), 7.40-7.30 (m, 8H), 7.25-7.15(m, 2H), 4.75(m, 1H), 4.60(m, 1H), 4.50 (m, 1H), 4.20(m, 2H), 3.95(m, 1H), 2.85(m, 1H), 2.70(m, 1H), 9.10(m, 1H), 1.20(m, 6H)

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-isobutyramide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-isobutyramide, 2-(1-isopropyl-1H-imidazol-4-yl)-ethylamine (see preparation of intermediates) (30 mg, 0.2 mmol) and sodium iodide (6 mg, 0.04 mmol). LCMS (electrospray): m/z [$MH^+$] 652.44

Example 26

N-((1S,2R,3S,4R)-4-{6-(2,2-Diphenyl-ethylamino)-2-[2-(1-isopropyl-1H-imidazol-4-yl)-ethylamino]-purin-9-yl}-2,3-dihydroxy-cyclopentyl)-2-phenyl-acetamide trifluoro acetate N-{(1S,2R,3S,4R)-4-[2-Chloro-6-(2,2-diphenyl-ethylamino)-purin-9-yl]-2,3-dihydroxy-cyclopentyl}-2-phenyl-acetamide A solution of (1S,2R,3S,5R)-3-amino-5-[2-chloro-6-(2,2-diphenyl-ethylamino)-purin-9-yl]-cyclopentane-1,2-diol hydrochloride (an intermediate for preparing the compound of Example 22) (100 mg, 0-2 mmol) in dry THF (1 ml) is treated with diisopropylethylamine (0.17 ml, 1 mmol) and phenylacetyl chloride (0.026 ml, 0.2 mmol) and the mixture is stirred at room temperature for 18 hours. The solvent is removed under reduced pressure and the residue is dissolved in dichloromethane (2 ml) and washed with dilute hydrochloric acid (2 ml). The organic layer is separated and evaporated under reduced pressure to afford the title compound (114 mg). LCMS (electrospray): m/z [$MH^+$] 583.27

N-((1S,2R,3S,4R)-4-{6-(2,2-Diphenyl-ethylamino)-2-[2-(1-isopropyl-1H-imidazol-4-yl-4-ethylamino]-purin-9-yl}-2,3-dihydroxy-cyclopentyl)-2-phenyl-acetamide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-2-phenyl-acetamide, 2-(1-isopropyl-1H-imidazol-4-yl)-ethylamine (see preparation of intermediates) (30 mg, 0.2 mmol) and sodium iodide (6 mg, 0.04 mmol). LCMS (electrospray): m/z [$MH^+$] 700.45

Example 27

Cyclobutanecarboxylic acid {(1S,2R,3S,4R)-4-[6-(2,2-diphenyl-ethylamino)-2-(Z-piperidin-1-yl-ethylamino)-purin-9-yl]-2,3-dihydroxy-cyclopentyl}-amide trifluoro acetate The title compound is prepared using a method that is analogous to that used to, prepare the compound of Example 22 using cyclobutanecarboxylic acid {(1S,2R,3S,4R)-4-[2-chloro-6-(2,2-diphenyl-ethylamino)-purin-9-yl]-2,3-dihydroxycyclopentyl}-amide (an intermediate for preparing Example 23), 1-(2-aminoethyl)piperidine (0.057 ml, 0.4 mmol) and sodium iodide (6 mg, 0.04 mmol). LCMS (electrospray): m/z [$MH^+$] 639.45

Example 28

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-butyramide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-butyramide (an intermediate for preparing Example 24), 1-(2-aminoethyl)-piperidine (0.057 ml, 0.4 mmol) and sodium iodide (6 mg, 0.04 mmol). LCMS (electrospray): m/z [$MH^+$] 627.44

Example 29

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-isobutyramide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-isobutyramide (an intermediate for preparing Example 25), 1-(2-aminoethyl)-piperidine (0.057 ml, 0.4 mmol) and sodium iodide (6 mg, 0.04 mmol). LCMS (electrospray): m/z [$MH^+$] 627.44

Example 30

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-2-phenyl-acetamide trifluoroacetate The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-2-phenyl-acetamide (an intermediate of Example 26), 1-(2-aminoethyl)-piperidine (0.057 ml, 0.4 mmol) and sodium iodide (6 mg, 0.04 mmol). LCMS (electrospray): m/z [$MH^+$] 675.47

Example 31

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-N'-(2-piperidin-1-yl-ethyl)-oxalamide Isoxazole-5-carboxylic acid {(1S,2R,3S,4R)-4-[2-chloro-6-(2,2-diphenyl-ethylamino)-purin-9-yl]-2,3-dihydroxy-cyclopentyl}-amide The title compound is prepared by the same method as cyclobutanecarboxylic acid {(1S,2R,3S,4R)-4-[2-chloro-6-(2,2-diphenyl-ethylamino)-purin-9-yl]-2,3-dihydroxy-cyclopentyl}-amide from (1S,2R,3S,5R)-3-amino-5-[2-chloro-6-(2,2-diphenyl-ethylamino)-purin-9-yl]-cyclopentane-1,2-diol hydrochloride (an intermediate for preparing the compound of Example 22) and isoxazole-5-carbonyl chloride to afford the title compound. LCMS (electrospray): m/z [$MH^+$] 560.28.

N-{(1S,2R,3S,4R)-4-[6-(2,2-Diphenyl-ethylamino)-2-(2-piperidin-1-yl-ethylamino)-purin-9-yl]-2,3-dihydroxy-cyclopentyl}-N'-(2-piperidin-1-yl-ethyl)-oxalamide The title compound is prepared using a method that is analogous to that used to prepare the compound of Example 22 using isoxazole-5-carboxylic acid {(1S,2R,3S,4R)-4-[2-chloro-6-(2,2-diphenyl-ethylamino)-purin-9-yl]-2,3-dihydroxy-cyclopentyl}-amide, 1-(2-aminoethyl)-piperidine (51 mg, 0.4 mmol) and sodium iodide (6 mg, 0.04 mmol). LCMS (electrospray): m/z [$MH^+$] 739.55

Example 32

Cyclopropanecarboxylic acid {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-amide The title compound is prepared using a method that is analogous to that used to prepare the compound of Example 22 using cyclopropanecarboxylic acid {(1S,2R,3S,4R)-4-[2-chloro-6-(2,2-diphenyl-ethylamino)-purin-9-yl]-2,3-dihydroxy-cyclopentyl}-amide (an intermediate for preparing Example 22), (R)-pyrrolidin-3-ylamine (34 mg, 0.4 mmol) and sodium iodide (6 mg, 0.04 mmol) to give a mixture of two regioisomers which are purified by reverse phase column chromatography (Isolute™ C18, 0-100% acetonitrile in water-0.1% TFA) to give a product which is predominantly cyclopropanecarboxylic acid {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-amide. LCMS (electrospray): m/z [$MH^+$] 583.42

Example 33

Cyclobutanecarboxylic acid {(1S,2R,3S,4R)-4-[2-((R)-3-amino-pyrrolidin-1-yl)-6-(2,2-diphenyl-ethylamino-3)-purin-9-yl]-2,3-dihydroxy-cyclopentyl}-amide The title compound is prepared using a method that is analogous to that used to prepare the compound of Example 22 using cyclobutanecarboxylic acid {(1S,2R,3S,4R)-4-[2-chloro-6-(2,2-diphenyl-ethylamino)-purin-9-yl]-2,3-dihydroxy-cyclopentyl}-amide (an intermediate for preparing Example 23), (R)-pyrrolidin-3-ylamine (34 mg, 0.4 mmol) and sodium iodide (6 mg, 0.04 mmol) to give a mixture of two regioisomers which are purified by reverse phase column chromatography (Isolute™ C18, 0-100% acetonitrile in water-0.1% TFA) to give a product which is predominantly cyclobutanecarboxylic acid {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-amide. LCMS (electrospray): m/z [MH+] 597.45

Example 34

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-phenyl-acetamide The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-2-phenyl-acetamide (an intermediate for preparing Example 26), (R)-pyrrolidin-3-ylamine (34 mg, 0.4 mmol) and sodium iodide (6 mg, 0.04 mmol) to give a mixture of two regioisomers which are purified by reverse phase column chromatography (Isolute™ C18, 0-100% acetonitrile in water—0.1% TFA) to give a product which is predominantly N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-phenyl-acetamide. LCMS (electrospray): m/z [MH+] 633.46

Example 35

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-3-phenyl-propionamide N-{(1S,2R,3S,4R)-4-[2-Chloro-6-(2,2-diphenyl-ethylamino)-purin-9-yl]-2,3-dihydroxy-cyclopentyl}-3-phenyl-propionamide A solution of (1S,2R,3S,5R)-3-amino-5-[2-chloro-6-(2,2-diphenyl-ethylamino)-purin-9-yl]-cyclopentane-1,2-diol hydrochloride (an intermediate for preparing the compound of Example 22) (100 mg, 0.2 mmol) in dry THF (1 ml) is treated with diisopropylethylamine (0.17 ml, 1 mmol) and 3-phenyl-propionyl chloride (0.03 ml, 0.2 mmol) and the mixture is stirred at room temperature for 18 hours. The solvent is removed under reduced pressure and the residue is dissolved in dichloromethane (2 ml) and washed with dilute hydrochloric acid (2 ml). The organic layer is separated and evaporated under reduced pressure to afford the title compound. LCMS (electrospray): m/z [MH+] 597.32

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-3-phenyl-propionamide The title compound is prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-3-phenyl-propionamide, (R)-pyrrolidin-3-ylamine (34 mg, 0.4 mmol) and sodium iodide (6 mg, 0.04 mmol) to give a mixture of two regioisomers which are purified by reverse phase column chromatography (Isolute™ C18, 0-100% acetonitrile in water—0.1% TFA) to give a product which is predominantly N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-phenyl-acetamide. LCMS (electrospray): m/z [MH+] 647.47

Examples 36a and 36b

N-{(1S,2R,3S,4R)-4-[2-((1S,3R)-3-Amino-pyrrolidin-1-yl)-6-(2,2-diphenyl-ethylamino)-purin-9-yl]-2,3-dihydroxy-cyclopentyl}-propionamide and N-{(1S,2R,3S,4R)-4-[6-(2,2-diphenyl-ethylamino)-2-((R)-pyrrolidin-3-yl-amino)-purin-9-yl]-2,3-dihydroxy-cyclopentyl}-propionamide Example 36a

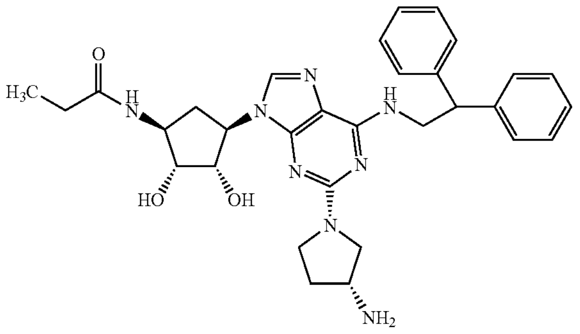

Example 36b

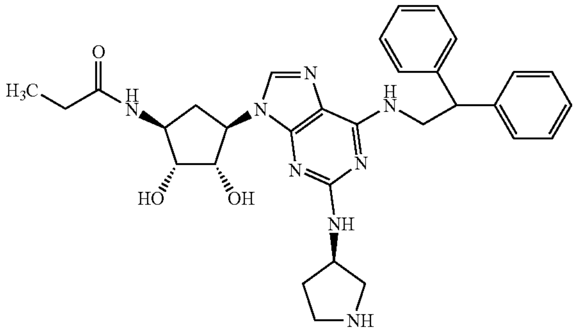

These compounds are prepared using a method that is analogous to that used to prepare the compound of Example 22 using N-{(1S,2R,3S,4R)-4-[2-chloro-6-(2,2-diphenyl-ethylamino)-purin-9-yl]-2,3-dihydroxy-cyclopentyl}-propionamide (an intermediate for preparing Example 16), (R)-pyrrolidin-3-ylamine (34 mg, 0.4 mmol) and sodium iodide (6 mg, 0.04 mmol) to give a mixture of two regioisomers, namely N-{(1S,2R,3S,4R)-4-[2-((1S,3R)-3-Amino-pyrrolidin-1-yl)-6-(2,2-diphenyl-ethylamino)-purin-9-yl]-2,3-dihydroxy-cyclopentyl}-propionamide (Example 36a) and N-{(1S,2R,3S,4R)-4-[6-(2,2-diphenyl-ethylamino)-2-((R)-pyrrolidin-3-yl-amino)-purin-9-yl]-2,3-dihydroxy-cyclopentyl}-propionamide (Example 36b), which are purified by reverse phase column chromatography (Isolute™ C18, 0-100% acetonitrile in water—0.1% TFA) to give a product which is predominantly N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide. LCMS (electrospray): m/z [MH+] 571.41

Example 37a and 37b

N-[(1S,2R,3S,4R)-4-(6-(2,2-Diphenyl-ethylamino)-2-{(1S,3R)-3-[3-(3,4,5,6-tetrahydro-2H-[1,2']bipyridinyl-4-yl)-ureido]-pyrrolidin-1-yl}-purin-9-yl)-2,3-dihydroxy-cyclopentyl]-propionamide and (R)-3-[9-((1R,2S,3R,4S)-2,3-Dihydroxy-4-propionylamino-cyclopentyl)-6-(2,2-diphenyl-ethylamino)-9H-purin-2-ylamino]-pyrrolidine-1-carboxylic acid (3,4,56-tetrahydro-2H-[1,2']bipyridinyl-4-yl)-amide Example 37a

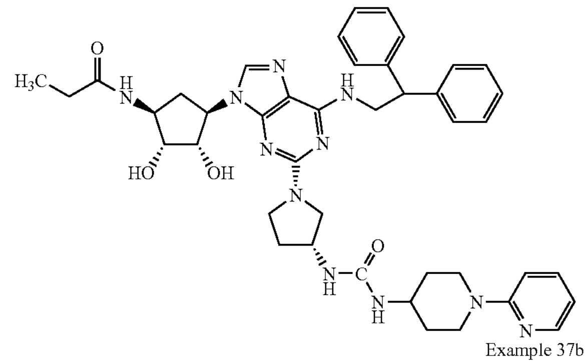

Example 37b

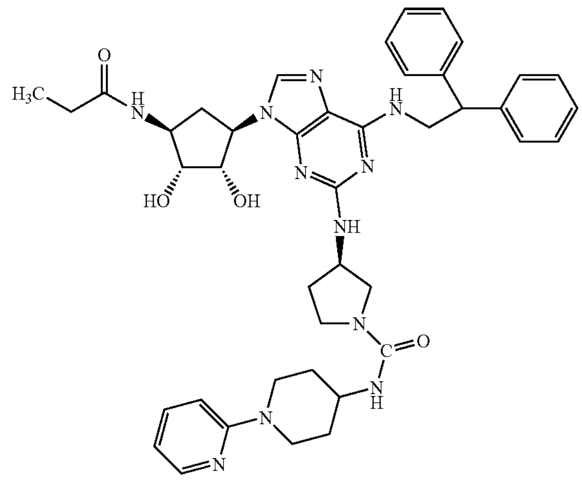

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide (30 mg, 0.04 mmol) is dissolved in toluene (2 ml) and iPrOH (1 ml). N-[1-(2-Pyridinyl)-4-piperidinyl]-1H-imidazole-1-carboxamide (prepared using the procedure described in international patent application WO 01/94368) (12 mg, 0.044 mmol) is added as a solution in dichloromethane. The reaction mixture is stirred at room temperature. The reaction is shown to be complete by LCMS after 24 hours. The solvent is removed in vacuo. The title compounds exist as a mixture of two regioisomers, namely N-[(1S,2R,3S,4R)-4-(6-(2,2-Diphenyl-ethylamino)-2-{(1S,3R)-3-[3-(3,4,5,6-tetrahydro-2H-[1,2']bipyridinyl-4-yl)-ureido]-pyrrolidin-1-yl}-purin-9-yl)-2,3-dihydroxy-cyclopentyl]-propionamide (Example 37a) and (R)-3-[9-((1R,2S,3R,4S)-2,3-Dihydroxy-4-propionylamino-cyclopentyl)-6-(2,2-diphenyl-ethylamino)-9H-purin-2-ylamino]-pyrrolidine-1-carboxylic acid (3,4,5,6-tetrahydro-2H-[1,2']bipyridinyl-4-yl)-amide (Example 37b), and are separated by flash column chromatography (Isolute™ C18, 0-100% acetonitrile in water). LCMS (electrospray): m/z [MH+] 596.42

The structures of the compounds of Example 37a and 37b are assigned using secondary isotope effects in NMR Spectroscopy. Isotope effects are well established in NMR spectroscopy (B. A. Bernheim and H. Batiz-Hernandez, *Prog. Nucl Magn. Reson. Spectrosc.* 3, 63-85 [1967]). Primary isotope effects have been widely studied (L. J. Altman et al. *J. Am. Chem. Soc.* 100, 8264-8266 [1978]), but it is the secondary isotope shift that has provided important structural information. These secondary isotope effects are observed in the $^{1}H$ or X-nucleus (usually $^{13}C$) NMR spectra of partially deuterated compounds, a technique known as SIMPLE (Secondary Isotope Multiplets of Partially Labelled Entities). Partial deuteration of exchangeable protons in molecules permits direct observation of the different isotopomers measured under conditions of slow exchange, and the resonance lines separations can be analyzed in terms of two-bond and three-bond isotope effects that contribute to the deuterium-induced secondary isotope shift. For example, signals from single carbon atoms are observed as a series of multiplets with intensity ratios that vary quantitatively with $^{1}H$:$^{2}H$ ratios. The magnitude of the two- and three-bond effects vary with the configuration of the carbons, and also the substitution and hydrogen bonding of these exchangeable groups. It is these signal multiplet formations and magnitude of isotope effects are used to unambiguously assign and confirm the structures of Example 37a and Example 37b.

The proton and carbon spectra of the two molecules are assigned by means of standard 1- and 2-D techniques, based on the proposed structures. The two urea carbonyls have a shift of 157.38 ppm in Example 37a and 156.34 ppm in Example 37b respectively. Both carbonyl moieties are bonded to two nitrogen atoms, however the key difference is that Example 37a is bonded to two NH groups, while the equivalent carbonyl in Example 37b is bonded to one NH group and to the fully substituted nitrogen of the proline ring.

Careful titration of deuterium oxide into the two samples results in an approximate 50:50 ratio of protonated and deuterated exchangeable moieties. The titration is monitored by means of $^{1}H$ NMR, measuring the integrals of the exchangeable protons on addition of 1 µl aliquots of $D_2O$. High-resolution $^{13}C$ spectra are then run on both samples. The linkage carbonyl of Example 37a shows a triplet structure, which can only arise from the existence of two partially deuterated groups within two bonds (the triplet consists of NHCONH, [NDCONH/NDCONH] and NDCOND carbon resonances). However, the equivalent carbon in Example 37b consists of a doublet structure, confirming that this linkage carbonyl is bonded to only one NH grouping thus confirming its structure.

Example 38

9-((1R,2S,3R,4S)-2,3-Dihydroxy-4-propionylamino-cyclopentyl)-6-(2,2-diphenyl-ethylamino)-9H-purine-2-carboxylic acid {2-[3-(3,4,5,6-tetrahydro-2H-[1,2]bipyridinyl-4-yl)ureido]-ethyl}-amide 6-(2,2-Diphenyl-ethylamino)-9H-purine-2-carboxylic acid methyl ester 6-(2,2-Diphenyl-ethylamino)-9H-purine-2-carboxylic acid methyl ester hydrochloride (prepared using the procedure described in international patent application WO 2001/94368) (35 g, 85.3 mmol) is placed in a flask under an atmosphere of argon. Dry $CHCl_3$(300 ml) and N,O-bis(trimethylsilyl)acetamide (61 ml) are added and the reaction mixture is refluxed for 1 hour. The reaction mixture is allowed to cool and any volatiles removed in vacuo. To the resulting oil is added MeOH (300 ml). The resulting white solid is filtered and washed with MeOH (2×200 ml) and then dried in a vacuum oven to give the title compound. $^1$H NMR (DMSO, 400 MHz).

6-(2,2-Diphenyl-ethylamino)-9-((1R,4S)-4-hydroxy-cyclopent-2-enyl)-9H-purine-2-carboxylic acid methyl ester To 6-(2,2-diphenyl-ethylamino)-9H-purine-2-carboxylic acid methyl ester (5 g 13.4 mmol) under an atmosphere of argon is added dry deoxygenated tetrahydrofuran (100 ml) and dry dimethyl sulfoxide (2 ml). Sodium hydride 95% (0.32 g, 13.4 mmol) is then added and the solution is stirred at 40° C. Separately to (1S,4R)-cis 4-acetoxy-2-cyclopenten-1-ol (1.89 g. 13.4 mmol) and triphenylphosphine (0.53 g, 2.0 mmol) in dry deoxygenated tetrahydrofuran (20 ml) is added tris(dibenzylideneacetone)dipalladium(0) (0.69 g, 0.67 mmol) and the mixture stirred at room temperature for 10 minutes. This solution is added to the anion solution via syringe and the resulting mixture is then stirred at 80° C. The reaction is shown to be complete by LCMS after 2 hours. The reaction mixture is allowed to cool, methanol is added and a solid is filtered. The filtrate is concentrated in vacuo and the title compound is obtained by precipitation from dichloromethane/hexane. $^1$H NMR (MeOD, 400 MHz); 8.15(s, 1H), 7.40-7.15(m, 10H), 6.20(m, 1H), 5.95(m, 1H), 5.50(m, 2H), 4.75(m, 2H), 4.55(m, 1H), 4.10(m 2H), 3.90(s, 2H), 3.80(s, 1H), 2.9(m, 1H), 1.75(m, 1H).

6-(2,2-Diphenyl-ethylamino)-9-((1R,4S)-4-ethoxy-carbonyloxy-cyclopent-2-enyl)-9H-purine-2-carboxylic acid methyl ester 6-(2,2-Diphenyl-ethylamino)-9-((1R,4S)-4-hydroxy-cyclopent-2-enyl)-9H-purine-2-carboxylic acid methyl ester (2.80 g, 6.14 mmol) is placed in an oven-dried flask under an atmosphere of argon. Dry tetrahydrofuran (30 ml) is added followed by dry pyridine (0.97 g, 12.3 mmol). Ethyl chloroformate (2.66 g, 24.6 mmol) is added slowly and the reaction mixture is stirred at room temperature. The reaction is shown to be complete by LCMS after 3 hours. The solvent is removed in vacuo and the residue is partitioned between dichloromethane (200 ml) and 1M HCl (2×200 ml). The organic layer is washed with saturated sodium bicarbonate solution (2×200 ml), water (2×100 ml), brine (2×100 ml), dried over $MgSO_4$, filtered and the solvent is removed in vacuo. The title compound is obtained after purification by flash column chromatography (silica, 4% MeOH in dichloromethane). MS (ES+) m/e 528.3 ($MH^+$).

9-((1R,4S-4-Di-tert-butoxycarbonylamino-cyclopent-2-enyl)-6-(2,2-diphenyl-ethylamino)-9H-purine-2-carboxylic acid methyl ester 6-(2,2-Diphenyl-ethylamino)-9-((1R,4S)-4-ethoxycarbonyloxy-cyclopent-2-enyl)-9H-purine-2-carboxylic acid methyl ester (2.2 g, 4.2 mmol) is dissolved in deoxygenated tetrahydrofuran. The resultant solution is stirred under an atmosphere of argon at room temperature. Di-t-butyl iminodicarboxylate (0.9 g, 4.2 mmol), triphenylphosphine (0.16 g, 0.63 mmol) and triethylamine (0.42 g, 4.2 mmol) are added followed by tris(dibenzylideneacetone)-dipalladium(0) (0.22 g, 0.21 mmol). The reaction mixture is then stirred at 45° C. for 4 hours, allowed to cool to room temperature, methanol is added and the reaction mixture filtered. The filtrate is concentrated in vacuo. The resultant oil is purified by column chromatography (silica, 80% ether in hexane) to yield the title compound, MS (ES+) m/e 536.4($MH^+$).

9-((1R,2S,3R,4S)-4-Di-tert-butoxycarbonylamino-2,3-dihydroxy-cyclopentyl)-6-(2,2-diphenylethylamino)-9H-purine-2-carboxylic acid methyl ester The title compound is prepared from 9-((1R,4S)-4-di-tert-butoxycarborlylamino-cyclopent-2-enyl)-6-(2,2-diphenyl-ethylamino)-9H-purine-2-carboxylic acid methyl ester using a procedure analogous to that of (1R,2S,3R,1S)-3-[2-chloro-6-(2,2-diphenyl-ethylamino)-purin-9-yl]-5-(di-Boc-amino)-cyclopentane-1,2-diol. MS (ES+) m/e 689.4 ($MH^+$).

9-((1R,2S,3R,4S)-4-Amino-2,3-dihydroxy-cyclopentyl)-6-(2,2-diphenyl-ethylamino)-9H-purine-2-carboxylic acid methyl ester 9-((1R,2S,3R,4S)-4-Di-tert-butoxycarbonylamino-2,3-dihydroxy-cyclopentyl)-6-(2,2-diphenyl-ethylamino)-9H-purine-2-carboxylic acid methyl ester (0.5 g, 0.73 mmol) is dissolved in dioxane and stirred under an atmosphere of argon. 4M HCl in dioxane (3.68 ml, 14.5 mmol) is added and the resultant solution is stirred for 20 hours then concentrated in vacuo. The title compound is obtained by flash column chromatography (Isolute™ C18, 0-100% acetonitrile in water). MS (ES+) m/e 489.3 ($MH^+$).

9-((1R,2S,3R,4S)-2,3-Dihydroxy-4-propionylamino-cyclopentyl)-6-(2,2-diphenyl-ethylamino)-9H-purine-2-carboxylic acid methyl ester 9-((1R,2S,3R,4S)-1,4-Amino-2,3-dihydroxy-cyclopentyl)-6-(2,2-diphenyl-ethylamino)-9H-purine-2-carboxylic acid methyl ester hydrochloride (200 mg, 0.36 mmol) is dissolved in tetrahydrofuran (5 ml). Diisopropylethylamine (0.16 ml, 0.9 mmol) is added and the solution is stirred for 10 minutes. Propionyl chloride (33 mg, 0.36 mmol) is added and the reaction mixture is stirred at room temperature for 1 hour. The reaction is quenched with methanol and the title compound is obtained by flash column chromatography (Isolute™ C18, 0-100% acetonitrile in water). MS (ES+) m/e 545.3 ($MH^+$).

9-((1R,2S,3R,4S)-2,3-Dihydroxy-4-propionylamino-cyclopentyl)-6-(2,2-diphenyl-ethylamino)-9H-purine-2-carboxylic acid (2-amino-ethyl)-amide 9-((1R,2S,3R,4S)-2,3-Dihydroxy-4-propionylamino-cyclopentyl)-6-(2,2-diphenyl-ethylamino)-9H-purine-2-carboxylic acid methyl ester (62 mg, 1.0 mmol) is dissolved in ethylene diamine (3.4 ml, 51 mmol) and the solution is stirred at 105° C. The reaction is shown to be complete by LCMS after 45 minutes. The reaction mixture is concentrated in vacuo and the title compound is obtained after purification by reverse phase column chromatography (Isolute™ C18, 0-100% acetonitrile in water). MS (ES+) m/e 573.4 ($MH^+$).

9-((1R,2S,3R,4S)-2,3-dihydroxy-4-propionylamino-cyclopentyl)-6-(2,2-diphenyl-ethylamino)-9H-purine-2-carboxylic acid {2-[3-(3,4,5,6-tetrahydro-2H-[1,2]bipyridinyl-4-yl)ureido]-ethyl}-amide 9-((1R,2S,3R,4S)-2,3-Dihydroxy-4-propionylamino-cyclopentyl)-6-(2,2-diphenyl-ethylamino)-9H-purine-2-carboxylic acid (2-amino-ethyl)-amide (25 mg, 0.044 mmol) is dissolved in toluene (2 ml) and $^{i}$PrOH (1 ml). N-[1-(2-Pyridinyl)-4-piperidinyl]-1H-imidazole-1-carboxamide (prepared using the procedure described in international patent application WO 01/94368) (12 mg, 0.044 mmol) is added as a solution in dichloromethane. The reaction mixture is stirred at room temperature. The reaction is shown to be complete by LCMS after 24 hours. The solvent is removed in vacuo. The title compound is obtained by flash column chromatography (Isolute™ C18, 0-100% acetonitrile in water). MS (ES+) m/e 388.7($MH^+$).

An alternative method for preparing the compound of Example 38 is described below:

9-[(1R,4S)-4-(tert-Butoxycarbonyl-propionyl-amino)-cyclopent-2-enyl]-6-(2,2-diphenyl-ethylamino)-9H-purine-2-carboxylic acid methyl ester This compound, which is the trifluoroacetate salt of the final compound of Example 37, is prepared using a method that is analogous to that used to prepare 9-((1R,4S)-4-Di-tert-butoxycarbonylamino-cyclopent-2-enyl)-6-(2,2-diphenyl-ethylamino)-9H-purine-2-carboxylic acid methyl ester by replacing di-t-butyl iminodicarboxylate with propionyl-carbamic acid tert-butyl ester.

9-[(1R,2S,3R,4S)-4-(tert-Butoxycarbonyl-propionyl-amino)-2.3 dihydroxy-cyclopentyl]-6-(2,2-diphenyl-ethylamino)-9H-purine-2-carboxylic acid methyl ester To a stirred suspension comprising 9-[(1R,4S)-4-(tert-butoxycarbonyl-propionyl-amino)-cyclopent-2-enyl]-6-(2,2-diphenyl-ethylamino)-9H-purine-2-carboxylic acid methyl ester (6.6 g, 10.82 mmol), methane sulphonamide (1.03 g, 10.82 mmol) and AD-mix-α (16.23 g) in t-butanol (40 ml) and water (40 ml) is added osmium tetroxide (3 ml of a 4% solution in water). The reaction mixture is stirred vigorously for 36 hours. The reaction mixture is partitioned between ethyl acetate and water and the organic portion is dried ($MgSO_4$) and concentrated in vacuo. The titled product is precipitated from methanol. Further product is derived from the mother liquor by chromatography on silica eluting with DCM:methanol (25:1).

{(1S,2R,3S,4R)-4-[2-(2-Amino-ethylcarbamoyl)-6-(2,2-diphenyl-ethylamino)-purin-9-yl]-2,3-dihydroxy-cyclopentyl}-carbamic acid tert-butyl ester This compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide by replacing 9-((1R,2S,3R,4S)-2,3-dihydroxy-4-propionylamino-cyclopentyl)-6-(2,2-diphenyl-ethylamino)-9H-purine-2-carboxylic acid methyl ester with 9-[(1R,2S,3R,4S)-4-(tert-butoxy-carbonyl-propionyl-amino)-2,3-dihydroxy-cyclopentyl]-6-(2,2-diphenyl-ethylamino)-9H-purine-2-carboxylic acid methyl ester.

(1S,2R,3S,4R)-4-(6-(2,2-Diphenyl-ethylamino)-[2-{2-[3-(3,4,5,6-tetrahydro-2H-[1-2']bipyridinyl-4-yl)-ureido]-ethylcarbamoyl}-purin-9-yl)-2,3-dihydroxy-cyclopentyl]-carbamic acid tert-butyl ester This compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid {2-[3-(3,4,5,6-tetra-hydro-2H-[1,2]bipyridinyl-4-yl)ureido]-ethyl}-amide by replacing 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide with {(1S,2R,3S,4R)-4-[2-(2-Amino-ethylcarbamoyl)-6-(2,2-diphenyl-ethylamino)-purin-9-yl]-2,3-dihydroxy-cyclopentyl}-carbamic acid tert-butyl ester.

9-((1R,2S,3R,4S)-4-Amino-2,3-dihydroxy-cyclopentyl)-6-(2,2-diphenyl-ethylamino)-9H-purine-2-carboxylic acid {2-[3-(3,4,5,6-tetrahydro-2H-[1,2'] bipyridinyl-4-yl)-ureido]-ethyl}-amide dihydrochloride This compound is prepared analogously to 9-((1R,2S,3R,4S)-4-Amino-2,3-dihydroxy-cyclopentyl)-6-(2,2-diphenyl-ethylamino)-9H-purine-2-carboxylic acid methyl ester by replacing 9-((1R,2S,3R,4S)-4-Di-tert-butoxycarbonylamino-2,3-dihydroxy-cyclopentyl)-6-(2,2-diphenyl-ethylamino)-9H-purine-2-carboxylic acid methyl ester with (1S,2R,3S,4R)-4-(6-(2,2-Diphenyl-ethylamino)-2-{2-[3-(3,4,5,6-tetrahydro-2H-[1,2']bipyridinyl-4-yl)-ureido]-ethylcarbamoyl}-purin-9-yl)-2,3-dihydroxy-cyclopentyl]-carbamic acid tert-butyl ester.

9-((1R,2S,3R,4S)-2,3-Dihydroxy-4-propionylamino-cyclopentyl)-6-(2,2-diphenyl-ethylamino)-9H-purine-2-carboxylic acid {2-[3-(3,4,5,6-tetrahydro-2H-[1,2]bipyridinyl-4-yl)ureido]-ethyl}-amide trifluoroacetate This compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid methyl ester by replacing 9-((1R,2S,3R,4S)-,4-amino-2,3-dihydroxy-cyclopentyl)-6-(2,2-diphenyl-ethylamino)-9H-purine-2-carboxylic acid methyl ester hydrochloride with 9-((1R,2S,3R,4S)-4-Amino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide dihydrochloride.

Example 39

N-((1S,2R,3S,4R)-4-{6-(2,2-Diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate This compound is prepared analogously to Example 22 by replacing cyclopropane carboxylic acid {(1S,2R,3S,4R)-4-[2-chloro-6-(2,2-diphenyl-ethylamino)-purin-9-yl]-2,3-dihydroxy-cyclopentyl}-amide with N-{(1S,2R,3S,4R)-4-[2-chloro-6-(2,2-diphenyl-ethylamino)-purin-9-yl]-2,3- dihydroxy-cyclopentyl}-propionamide and by replacing 2-(1-isopropyl-1H-imidazol-4-yl)-ethyl amine with 1,3-di(R)-pyrrolidin-3-yl-urea.

Example 40

Cyclobutanecarboxylic acid [(1S,2R,3S,4R)-4-(6-(2,2-diphenyl-ethylamino)-2-{(R)-3-[3-(3,4,5,6-tetrahydro-2H-[1,2']bipyridinyl-4-yl)-ureido]-pyrrolidin-1-yl}-purin-9-yl)-2,3-dihydroxy-cyclopentyl]-amide trifluoroacetate A mixture comprising cyclobutanecarboxylic acid {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-amide dihydrochloride (0.02 g, 0.03 mmol), TEA (0.09 ml, 0.06 mmol) in iso-propanol (0.5 ml) is treated with imidazole-1-carboxylic acid (3,4,5,6-tetrahydro-2H-[1,2']bipyridinyl-4-yl)-amide (0.04 ml of a 10 mg/ml solution in DCM, 0.03 mmol). After the reaction mixture has stirred at room temperature overnight, the solvent is removed in vacuo and purification of the crude by reverse phase column chromatography (Isolute™ C18, 0-1000% acetonitrile in water—0.1% TFA) yields the titled product.

Example 41

9-[(1R,2S,3R,4S)-4-(Cyclobutanecarbonyl-amino)-2,3-dihydroxy-cyclopentyl]-6-(2,2-diphexyl-ethylamino)-9H-purine-2-carboxylic acid {2-[3-(3,4,5,6-tetrahydro-2H-[1,2']bipyridinyl-4-yl)-ureido]-ethyl}-amide This compound is prepared analogously to 9-((1R,2S,3R,4S)-2,3-Dihydroxy-4-propionylamino-cyclopentyl)-6-(2,2-diphenyl-ethylamino)-9H-purine-2-carboxylic acid {2-[3-(3,4,5,6-tetrahydro-2H-[1,2]bipyridinyl-4-yl)ureido]-ethyl}-amide by replacing (1S,2R,3S,5R)-3-amino-5-[2-chloro-6-(2,2-diphenyl-ethylamino)-purin-9-yl]-cyclopentane-1,2-diol hydrochloride with 9-((1R,2S,3R,4S)-4-amino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide dihydrochloride.

Example 42

9-((1R,2S,3R,4S)-4-Acetylamino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide trifluoroacetate A mixture comprising 9-((1R,2S,3R,4S)-4-amino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide dihydrochloride (0.02 g, 25 μmol), TEA (0.013 g, 125 μmol) in THF (2 ml) is treated with acetyl chloride (0.003 g, 40 μmol). After the reaction mixture has stirred at room temperature overnight, the solvent is removed in vacuo and purification of the crude by reverse phase column chromatography (Isolute™ C18, 0-100% acetonitrile in water—0.11% TFA) yields the titled product.

Example 43

9-((1R,2S,3R,4S)-2,3-Dihydroxy-4-propionylamino-cyclopentyl)-6-(2,2-diphenyl-ethylamino)-9H-purine-2-carboxylic acid {2-[3-((R)-1-pyridin-2-yl-pyrrolidin-3-yl)-ureido]-ethyl}-amide trifluoroacetate A solution comprising 9-((1R,2S,3R,4S)-2,3-dihydroxy-4-propionylamino-cyclopentyl)-6-(2,2-diphenyl-ethylamino)-9H-purine-2-carboxylic acid methyl ester (0.01 g, 0.018 mmol) and 1-(2-amino-ethyl)-3-((R)-1-pyridin-2-yl-pyrrolidin-3-yl)-urea (0.022 g of a 1:5 mole ratio mixture with imidazole, 0.04 mmol) in 1,2-dichloroethane:iso-propanol (0.2 ml of a 1:1 mixture) is heated at reflux for 70 hours. The solvent is removed in vacuo and purification of the crude by reverse phase column chromatography (Isolute™ C18, 0-65% acetonitrile in water—0.1% TFA) yields the titled product.

Example 44

N-{(1S,2R,3S,4R)-4-[2-(4-Amino-piperidin-1-yl)-6-(2,2-diphenyl-ethylamino)-purin-9-yl]-2,3-dihydroxy-cyclopentyl}-propionamide dihydrochloride {1-[9-((1R,2S,3R,4S)-2,3-Dihydroxy-4-propionylamino-cyclopentyl)-6-(2,2-diphenyl-ethylamino)-9H-purin-2-yl]-piperidin-4-yl}-carbamic acid tert-butyl ester trifluoroacetate This compound is prepared analogously to cyclopropanecarboxylic acid ((1S,2R,3S,4R)-4-{6-(2,2-diphenyl-ethylamino)-2-[2-(1-isopropyl-1H-imidazol-4-yl)-ethylamino]-purin-9-yl}-2,3-dihydroxy-cyclopentyl)-amide trifluoroacetate by replacing cyclopropanes-carboxylic acid {(1S,2R,3S,4R)-4-[2-chloro-6-(2,2-diphenyl-ethylamino)-purin-9-yl]-2,3-dihydroxy-cyclopentyl}-amide with N-{(1S,2R,3S,4R)-4-[2-chloro-6-(2,2-diphenyl-ethylamino)-purin-9-yl]-2,3-dihydroxy-cyclopentyl}-propionamide and by replacing 2-(1-isopropyl-1H-imidazol-4-yl)-ethylamine with piperidin-4-yl-carbamic acid tert-butyl ester.

N-{(1S,2R,3S,4R)-4-[2-(4-Amino-piperidin-1-yl)-6-(2,2-diphenyl-ethylamino)-purin-9-yl]-2,3-dihydroxy-cyclopentyl}-propionamide dihydrochloride {1-[9-((1R,2S,3R,4S)-2,3-Dihydroxy-4-propionylamino-cyclopentyl)-6-(2,2-diphenyl-ethyl-amino)-9H-purin-2-yl]-piperidin-4-yl}-carbamic acid tert-butyl ester trifluoroacetate (0.02 g, 0.03 mmol) is dissolved in HCl (1 ml of a 1.25 M solution in methanol) and allowed to stand at room temperature overnight. The solvent is removed in vacuo to yield the titled compound.

Examples 45 and 46

These compounds, namely N-{(1S,2R,3S,4R)-4-[6-(2,2-diphenyl-ethylamino)-2-pyrrolidin-1-yl-purin-9-yl]-2,3-dihydroxy-cyclopentyl}-propionamide trifluoroacetate and N-{(1S,2R,3S,4R)-4-[6-(2,2-diphenyl-ethylamino)-2-piperazin-1-yl-purin-9-yl]-2,3-dihydroxy-cyclopentyl}-propionamide trifluoroacetate, are prepared analogously to cyclopropanecarboxylic acid ((1S,2R,3S,4R)-4-{6-(2,2-diphenylethylamino)-2-[2-(1-isopropyl-1H-imidazol-4-yl)-ethylamino]-purin-9-yl}-2,3-dihydroxy-cyclopentyl)-amide trifluoroacetate by replacing cyclopropanecarboxylic acid {(1S,2R,3S,4R)-4-[2-chloro-6-(2,2-diphenyl-ethylamino)-purin-9-yl]-2,3-dihydroxy-cyclopentyl}-amide with N-{(1S,2R,3S,4R)-4-[2-chloro-6-(2,2-diphenyl-ethylamino)-purin-9-yl]-2,3-dihydroxy-cyclopentyl}-propionamide and by replacing 2-(1-isopropyl-1H-imidazol-4-yl)-ethylamine with the appropriate amine.

Example 47

9-((1R,2S,3R,4S)-2,3-Dihydroxy-4-propionylamino-cyclopentyl)-6-(2,2-diphenyl-ethylamino)-9H-purine-2-carboxylic acid {2-[3-((S)-1-pyridin-2-yl-pyrrolidin-3-yl)-ureido]-ethyl}-amide trifluoroacetate This compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid {2-[3-((R)-1-pyridin-2-yl-pyrrolidin-3-yl)-ureido]-ethyl}-amide trifluoroacetate by replacing 1-(2-amino-ethyl)-3-((R)-1-pyridin-2-yl-pyrrolidin-3-yl)-urea with 1-(2-amino-ethyl)-3-((S)-1-pyridin-2-yl-pyrrolidin-3-yl)-urea.

Example 48

9-((1R,2S,3R,4S)-2,3-Dihydroxy-4-propionylamino-cyclopentyl)-6-(2,2-diphenyl-ethylamino)-9H-purine-2-carboxylic acid [2-(3-piperidin-4-yl-ureido)-ethyl]-amide 4-[3-(2-{[9-((1R,2S,3R,4S)-2,3-Dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester To a solution of 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide (0.1 g, 174 mmol) in chloroform (5 ml) is added 4-isocyanato-Z-piperidine (0.045 g, 0.174 mmol) in chloroform (5 ml). The reaction mixture is allowed to stir at room temperature overnight and then methanol is added to quench any residual isocyanate. The solvent is removed in vacuo to yield the titled compound which is used without further purification in the next step.

9-((1R,4S)-2,3-Dihydroxy-4-propionylamino-cyclopentyl)-6-(2,2-diphenyl-ethylamino)-9H-purine-2-carboxylic acid [2-(3-piperidin-4-yl-ureido)-ethyl]-amide A solution of 4-[3-(2-{[9-((1R,2S,3R,4S)-2,3-dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester (0.145 g, 0.174 mmol) in methanol (1 ml) under an atmosphere of Argon is treated with palladium hydroxide on carbon (0.054 g, 20% w/w carbon). The reaction mixture is placed under an atmosphere of hydrogen and stirred at room temperature for 72 hours and then filtered. The filtrate is concentrated in vacuo to yield the titled compound as a green oil.

Example 49

9-((1R,2S,3R,4S)-2,3-Dihydroxy-4-propionylamino-cyclopentyl)-6-(2,2-diphenyl-ethylamino)-9H-purine-2-carboxylic acid {2-[3-(1-methanesulfonyl-piperidin-4-yl)-ureido]-ethyl}-amide trifluoroacetate To a solution of 9-((1R,2S,3R,4S)-2,3-dihydroxy-4-propionylamino-cyclopentyl)-6-(2,2-diphenyl-ethylamino)-9H-purine-2-carboxylic acid [2-(3-piperidin-4-yl-ureido)-ethyl]-amide (0.01 g, 0.0143 mmol) in DMF (1 ml) under an inert atmosphere of argon is added triethylamine (TEA) (0.003 g, 0.0286 mmol) followed by mesyl chloride (0.0016 g, 0.0143 mmol). After standing at room temperature overnight, the solvent is removed in vacuo and purification of the crude by reverse phase column chromatography (Isolute™ C18, 0-100% acetonitrile in water—0.1% TFA) yields the titled product.

Example 50

N-((1S,2R,3S,4R)-4-{2-Chloro-6-[(naphthalen-1-ylmethyl)-amino]-purin-9-yl}-2,3-dihydroxy-cyclopentyl)-propionamide trifluoroacetate A solution comprising [(1S,2R,3S,4R)-4-(2,6-dichloro-purin-9-yl)-2,3-dihydroxy-cyclopentyl]-propionyl-carbamic acid tert-butyl ester (0.5 g, 1.1 mmol), DIPEA (0.227 ml, 1.3 mmol), 1-napthalenemethylamine (0.175 ml, 1.2 mmol) in 1,2-dichloro-ethane (3 ml) is heated at 50° C. overnight. Hydrochloric acid (10 ml of a 0.1 M solution) is added to the reaction mixture and following agitation, the organic portion is separated and treated with TFA (1 ml). After standing at room temperature for 2 hours, the solvent is removed in vacuo to yield the titled compound.

Example 51-53

These compounds namely,

N-{(1S,2R,3S,4R)-4-[2-chloro-6-(3,3-dimethyl-butylamino)-purin-9-yl]-2,3-dihydroxy-cyclopentyl}-propionamide trifluoroacetate (Example 51), N-{(1S,2R,3S,4R)-4-[2-chloro-6-(2,2-diphenyl-propylamino)-purin-9-yl]-2,3-dihydroxy-cyclopentyl}-propionamide (Example 52), N-{(1S,2R,3S,4R)-4-[2-chloro-6-(3,3-diphenyl-propylamino)-purin-9-yl]-2,3-dihydroxy-cyclopentyl}-propionamide (Example 53), are prepared analogously to N-((1S,2R,3S,4R)-4-{2-chloro-6-[(naphthalen-1-ylmethyl)-amino]-purin-9-yl}-2,3-dihydroxy-cyclopentyl)-propionamide trifluoroacetate by replacing 1-napthalenemethylamine with the appropriate amine. Examples 53 and 54 are also treated with potassium carbonate/methanol to afford the product in free form.

Example 54

N-((1S,2R,3S,4R)-4-{6-(1-Ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate A solution comprising N-{(1S,2R,3S,4R)-4-[2-chloro-6-(1-ethyl-propylamino)-purin-9-yl]-2,3-dihydroxy-cyclopentyl}-propionamide (0.02 g, 0.03 mmol) and 1,3-di(R)-pyrrolidin-3-yl-urea (0.03 g, 0.15 mmol) in DMSO (0.2 ml) is heated to 100° C. for 24 hours. Purification is carried out using mass directed preparative LC-MS eluting with acetonitrile:water:trifluoroacetic acid to afford the titled compound.

Example 55

N-((1S,2R,3S,4R)-2,3-Dihydroxy-4-{6-[(naphthalen-1-ylmethyl)-amino]-2-[(R)-3-((R)-3-pyrrolidin-3-ylureido)-pyrrolidin-1-yl]-purin-9-yl}-cyclopentyl)-propionamide trifluoroacetate This compound is prepared analogously to N-((1S,2R,3S,4R)-4-{6-(1-Ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate by replacing N-{(1S,2R,3S,4R)-4-[2-chloro-6-(1-ethyl-propylamino)-purin-9-yl]-2,3-dihydroxy-cyclopentyl}-propionamide with N-((1S,2R,3S,4R)-4-{2-chloro-6-[(naphthalen-1-ylmethyl)-amino]-purin-9-yl}-2,3-dihydroxy-cyclopentyl)-propionamide trifluoroacetate.

Example 56

N-{(1S,2R,3S,4R)-4-[2-((R)-3-Amino-pyrrolidin-1-yl)-6-(1-ethyl-propylamino)-purin-9-yl]-2,3-dihydroxy-cyclopentyl}-propionamide trifluoroacetate N-{(1S,2R,3S,4R)-4-[2-chloro-6-(1-ethyl-propylamino)-purin-9-yl]-2,3-dihydroxy-cyclopentyl}-propionamide (0.02 g, 0.03 mmol), (3R)-3-(BOC-amino)pyrrolidine (0.028 g, 0.15 mmol) and sodium iodide (0.004 g, 0.03 mmol) are placed in a 0.5-2.5 ml microwave vial. Acetonitrile (0.25 ml) and NMP (0.25 ml) are added and the reaction mixture is heated using microwave radiation in a Personal Chemistry Emrys™ Optimizer microwave reactor at 160° C. for 30 minutes. DCM (3 ml) and water (3 ml) are added to the reaction mixture and following agitation, the organic portion is separated and treated with TFA (0.5 ml). After standing at room temperature overnight purification is carried out using mass directed preparative LC-MS eluting with acetonitrile: water: trifluoroacetic acid to afford the titled compound.

Example 57

N-((1S,2R,3S,4R)-4-{2-((R)-3-Amino-pyrrolidin-1-yl)-6-[(naphthalen-1-ylmethyl)-amino]-purin-9-yl}-2,3-dihydroxy-cyclopentyl)-propionamide trifluoroacetate This compound is prepared analogously to N-{(1S,2R,3S,4R)-4-[2-((R)-3-Amino-pyrrolidin-1-yl)-6-(1-ethyl-propylamino)-purin-9-yl]-2,3-dihydroxy-cyclopentyl}-propionamide trifluoroacetate by replacing N-{(1S,2R,3S,4R)-4-[2-chloro-6-(1-ethyl-propylamino)-purin-9-yl]-2,3-dihydroxy-cyclopentyl}-propionamide with N-((1S,2R,3S,4R)-4-{2-chloro-6-[(naphthalen-1-ylmethyl)-amino]-purin-9-yl}-2,3-dihydroxy-cyclopentyl)-propionamide trifluoroacetate.

Examples 58 and 59

These compounds, namely N-((1S,2R,3S,4R)-4-{6-(2,2-diphenyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 58) and N-((1S,2R,3S,4R)-4-{6-(3,3-diphenyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 59), are prepared analogously to N-((1S,2R,3S,4R)-4-{6-(1-ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate by replacing N-{(1S,2R,3S,4R)-4-[2-chloro-6-(1-ethyl-propylamino)-purin-9-yl]-2,3-dihydroxy-cyclopentyl}-propionamide with the appropriate starting materials, the preparations of which are described herein.

Examples 60 and 61

These compounds, namely N-((1S,2R,3S,4R)-4-{6-(2,2-diphenyl-propylamino)-2-[2-(1-ethyl-1H-imidazol-4-yl)-ethylamino]-purin-9-yl}-2,3-dihydroxy-cyclopentyl)-propionamide trifluoroacetate (Example 60) and N-((1S,2R,3S,4R)-4-{6-(3,3-diphenyl-propyl-amino)-2-[2-(1-ethyl-1H-imidazol-4-yl)-ethylamino]-purin-9-yl-2,3-dihydroxy-cyclopentyl}-propionamide trifluoroacetate (Example 61), are prepared analogously to N-{(1S,2R,3S,4R)-4-[2-((R)-3-amino-pyrrolidin-1-yl)-6-(1-ethyl-propylamino)-purin-9-yl]-2,3-dihydroxy-cyclopentyl}-propionamide trifluoroacetate by replacing (3R)-3-(BOC-amino)pyrrolidine with 2-(1-ethyl-1H-imidazol-4-yl)-ethylamine and by replacing N-{(1S,2R,3S,4R)-4-[2-chloro-6-(1-ethyl-propylamino)-purin-9-yl]-2,3-dihydroxy-cyclopentyl}-propionamide with the appropriate starting materials, the preparations of which are described herein.

Example 62

N-((1S,2R,3S,4R)-4-{6-(3,3-Dimethyl-butylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate This compound is prepared analogously to N-((1S,2R,3S,4R)-4-{6-(1-ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate by replacing N-{(1S,2R,3S,4R)-4-[2-chloro-6-(1-ethyl-propylamino)-purin-9-yl]-2,3-dihydroxy-cyclopentyl}-propionamide with N-{(1S,2R,3S,4R)-4-[2-chloro-6-(3,3-dimethyl-butylamino)-purin-9-yl]-2,3-dihydroxy-cyclopentyl}-propionamide trifluoroacetate.

Example 63

N-{(1S,2R,3S,4R)-4-[6-(1-Ethyl-propylamino)-2-((S)-1-hydroxymethyl-2-phenyl-ethylamino)-purin-9-yl]-2,3-dihydroxy-cyclopentyl}-propionamide trifluoroacetate This compound is prepared analogously to N-{((1S,2R,3S,4R)-4-[6-(2,2-diphenyl-ethylamino)-2-((S)-1-hydroxymethyl-2-phenyl-ethylamino)-purin-9-yl]-2,3-dihydroxy-cyclopentyl}-propionamide (Example 16) by replacing N-{(1S,2R,3S,4R)-4-[2-chloro-6-(2,2-diphenyl-ethylamino)-purin-9-yl]-2,3-dihydroxy-cyclopentyl}-propionamide (Example 4) with N-{(1S,2R,3S,4R)-4-[2-chloro-6-(1-ethyl-propylamino)-purin-9-yl]-2,3-dihydroxy-cyclopentyl}-propionamide (Example 14).

Example 64

N-((1S,2R,3S,4R)-4-{6-(1-Ethyl-propylamino)-2-[((R)-1-ethyl-pyrrolidin-2-ylmethyl)-amino]-purin-9-yl}-2,3-dihydroxy-cyclopentyl)-propionamide trifluoroacetate This compound is prepared analogously to N-{(1S,2R,3S,4R)-4-[6-(2,2-diphenyl-ethylamino)-2-((S)-1-hydroxymethyl-2-phenyl-ethylamino)-purin-9-yl]-2,3-dihydroxy-cyclopentyl}-propionamide (Example 16) by replacing N-{(1S,2R,3S,4R)-4-[2-chloro-6-(2,2-diphenyl-ethylamino)-purin-9-yl]-2,3-dihydroxy-cyclopentyl}-propionamide (Example 4) with N-{(1S,2R,3S,4R)-4-[2-chloro-6-(1-ethyl-propylamino)-purin-9-yl]-2,3-dihydroxy-cyclopentyl}-propionamide (Example 14) and by replacing (S)-2-amino-3-phenyl-propan-1-ol with C-((R)-1-ethyl-pyrrolidin-2-yl)-methylamine.

Example 65

N-{(1S,2R,3S,4R)-4-[6-Amino-2-((S)-1-hydroxymethyl-2-phenyl-ethylamino)-purin-9-yl]-2,3-dihydroxy-cyclopentyl}-propionamide trifluoroacetate

N-((1S,2R,3S,4R)-4-{2-Chloro-6-[(9H-fluoren-9-ylmethyl)-amino]-purin-9-yl}-2,3-dihydroxy-cyclopentyl)-propionamide This compound is prepared analogously to N-((4S,2R,3S,4R)-4-{2-chloro-6-[(naphthalen-1-ylmethyl)-amino]-purin-9-yl}-2,3-dihydroxy-cyclopentyl)-propionamide trifluoroacetate (Example 50) by replacing 1-napthalenemethylamine with C-(9H-fluoren-9-yl)-methylamine.

N-{(1S,2R,3S,4R)-4-[6-Amino-2-((S)-1-hydroxymethyl-2-phenyl-ethylamino)-purin-9-yl]-2,3-dihydroxy-cyclopentyl}-propionamide trifluoroacetate This compound is prepared analogously to N-{(1S,2R,3S,4R)-4-[6-(2,2-diphenyl-ethylamino)-2-((S)-1-hydroxymethyl-2-phenyl-ethylamino)-purin-9-yl]-2,3-dihydroxy-cyclopentyl}-propionamide (Example 16) by replacing N-{(1S,2R,3S,4R)-4-[2-chloro-6-(2,2-diphenyl-ethylamino)-purin-9-yl]-2,3-dihydroxy-cyclopentyl}-propionamide (Example 4) with N-((1S,2R,3S,4R)-4-{2-chloro-6-[(9H-fluoren-9-ylmethyl)-amino]5-purin-9-yl}-1,3-dihydroxy-cyclopentyl)-propionamide.

Example 66

N-{(1S,2R,3S,4R)-2,3-Dihydroxy-4-[6-[(naphthalen-1-ylmethyl)-amino]-2-(2-piperidin-1-yl-ethylamino)-purin-9-yl]-cyclopentyl}-propionamide trifluoroacetate This compound is prepared analogously to N-{(1S,2R,3S,4R)-4-[6-(2,2-diphenyl-ethylamino)-2-((S)-1-hydroxymethyl-2-phenyl-ethylamino)-purin-9-yl]-2,3-dihydroxy-cyclopentyl}-propionamide (Example 16) by replacing N-{(1S,2R,3S,4R)-4-[2-chloro-6-(2,2-diphenyl-ethylamino)-purin-9-yl]-2,3-dihydroxy-cyclopentyl}-propionamide (Example 4) with N-((1S,2R,3S,4R)-4-{2-chloro-6-[(naphthalen-1-ylmethyl)-amino]-purin-9-yl}-2,3-dihydroxy-cyclopentyl)-propionamide trifluoroacetate (Example 50) and by replacing (S)-2-amino-3-phenyl-propan-1-ol with 2-piperidin-1-yl-ethylamine.

Example 67-69

These compounds namely, N-((1S,2R,3S,4R)-4-{2-(4-amino-cyclohexylamino)-6-[(naphthalen-1-ylmethyl)-amino]-purin-9-yl}-2,3-dihydroxy-cyclopentyl)-propionamide trifluoroacetate (Example 67), N-((1S,2R,3S,4R)-2,3-dihydroxy-4-{2-[2-(1H-imidazol-4-yl)-ethylamino]-6-[(naphthalen-1-ylmethyl)-amino]-purin-9-yl}-cyclo pentyl)-propionamide trifluoroacetate (Example 68) and N-((1S,2R,3S,4R)-4-{2-[((R)-1-Ethyl-pyrrolidin-2-ylmethyl)-amino]-6-[(naphthalen-1-ylmethyl)-amino]-purin-9-yl}-2,3-dihydroxy-cyclopentyl)-propionamide trifluoroacetate (Example 69) are prepared analogously to N-{(1S,2R,3S,4R)-2,3-dihydroxy-4-[6-[(naphthalen-1-ylmethyl)-amino]-2-(2-piperidin-1-yl-ethylamino)-purin-9-yl]-cyclopentyl}-propionamide trifluoroacetate (Example 66) by replacing 2-piperidin-1-yl-ethylamine with the appropriate amine.

Example 70

These compounds namely, N-{(1S,2R,3S,4R)-4-[2-(4-amino-cyclohexylamino)-6-(3,3-dimethyl-butylamino)-purin-9-yl]-2,3-dihydroxy-cyclopentyl}-propionamide trifluoroacetate (Example 70), N-((1S,2R,3S,4R)-4-{6-(3,3-dimethyl-butylamino)-2-[2-(1H-imidazol-4-yl)-ethylamino]-purin-9-yl}-2,3-dihydroxy-cyclopentyl)-propionamide trifluoroacetate (Example 71) and N-((1S,2R,3S,4R)-4-{6-(3,3-Dimethyl-butylamino)-2-[((R)-1-ethyl-pyrrolidin-2-ylmethyl)-amino]-purin-9-yl}-2,3-dihydroxy-cyclopentyl)-propionamide trifluoroacetate (Example 72) are prepared analogously to N-{(1S,2R,3S,4R)-4-[6-(2,2-diphenyl-ethylamino)-2-((S)-1-hydroxy-methyl-2-phenyl-ethylamino)-purin-9-yl]-2,3-dihydroxy-cyclopentyl}-propionamide (Example 16) by replacing N-{(1S,2R,3S,4R)-4-[2-chloro-6-(2,2-diphenyl-ethylamino)-purin-9-yl]-2,3-dihydroxy-cyclopentyl}-propionamide (Example 4) with N-{(1S,2R,3S,4R)-4-[2-chloro-6-(3,3-dimethyl-butylamino)-purin-9-yl]-2,3-dihydroxy-cyclopentyl}-propionamide trifluoroacetate (Example 51) and by replacing L-phenylalaminol with the appropriate amine.

Example 73

N-{(1S,2R,3S,4R)-4-[2-{(R)-3-[3-(2,6-Dichloro-pyridin-4-yl)-ureido]-pyrrolidin-1-yl}-6-(2,2-diphenyl-ethylamino)-purin-9-yl]-2,3-dihydroxy-cyclopentyl}-propionamide trifluoroacetate A solution of N-{(1S,2R,3S,4R)-4-[2-((R)-3-amino-pyrrolidin-1-yl)-6-(2,2-diphenyl-ethyl-amino)-purin-9-yl]-2,3-dihydroxy-cyclopentyl}-propionamide (Example 36) (23 mg, 40 μmol) in THF (1 ml) is treated with TEA (7.3 mg, 72 μmol) and then added to 2,6-dichloro-4-isocyanato-pyridine (6.8 mg 36 μmol). The reaction mixture is shaken at room temperature and then allowed to stand overnight. The solvent is removed in vacuo and purification by mass directed preparative LC-MS eluting with acetonitrile:water:trifluoroacetic acid affords the titled compound.

Example 74

N-((1S,2R,3S,4R)-4-{6-(2,2-Diphenyl-ethylamino)-2-[(R)-3-(3-thiophen-2-yl-ureido)-pyrrolidin-1-yl]-purin-9-yl}-2,3-dihydroxy-cyclopentyl)-propionamide trifluoroacetate This compound is prepared analogously to N-{(1S,2R,3S,4R)-4-[2-{(R)-3-[3-(2,6-dichloro-pyridin-4-yl)-ureido]-pyrrolidin-1-yl}-6-(2,2-diphenyl-ethylamino)-purin-9-yl]-2,3-dihydroxy-cyclopentyl}-propionamide trifluoroacetate (Example 73) by replacing 2,6-dichloro-4-isocyanato-pyridine with 2-thienyl isocyanate.

Example 75

N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-propionamide trifluoroacetate This compound is prepared analogously to 9-((1R,2S,3R,4S)-4-acetylamino-2,3-dihydroxy-cyclopentyl)-6-(2,2-diphenyl-ethylamino)-9H-purine-2-carboxylic acid {2-[3-(3,4,5,6-tetra-hydro-2H-[1,2']bipyridinyl-4-yl)-ureido]-ethyl}-amide trifluoroacetate (Ex. 42) by replacing 9-((1R,2S,3R,4S)-4-amino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide dihydrochloride (an intermediate for preparing Example 38) with N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 36) and by replacing acetyl chloride with 3-isocyanato-pyridine.

Example 76

Cyclobutanecarboxylic acid ((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-amide This compound is prepared analogously to N-((1S,2R,3S,4R)-4-{6-(1-ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 54) by replacing N-{(1S,2R,3S,4R)-4-[2-chloro-6-(1-ethyl-propylamino)-purin-9-yl]-2,3-dihydroxy-cyclopentyl}-propionamide (Example 14) with cyclobutanecarboxylic acid {(1S,2R,3S,4R)-4-[2-chloro-6-(2,2-diphenyl-ethylamino)-purin-9-yl]-2,3-dihydroxy-cyclopentyl}-amide (an intermediate used to prepare Example 23).

Example 77

4-Methyl-piperazine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate Imidazole-1-carboxylic acid {(R)-1-[9-((3aS,4R,6S,6aR)-2,2-dimethyl-6-propionylamino-tetrahydro-cyclopenta[1,3]dioxol-4-yl)-6-(2,2-diphenyl-ethylamino)-9H-purin-2-yl]-pyrrolidin-3-yl}-amide A mixture comprising N-{(3aR,4S,6R,6aS)-6-[2-((R)-3-amino-pyrrolidin-1-yl)-6-(2,2-diphenyl-ethylamino)-purin-9-yl]-2,2-dimethyl-tetrahydro-cyclopenta[1,3]dioxol-4-yl}-propionamide (see preparation of intermediates) (0.24 g, 0.39 mmol) and CDI (0.275 g, 1.7 mmol) in DCM is stirred at room temperature for 3 hours. Purification of the resulting mixture by chromatography on silica eluting with 0-5% MeOH in DCM yields the titled compound as a yellow oil. The compound exists as a mixture of the imidazole-urea intermediate together with variable amounts of the corresponding isocyanate and imidazole which are equally suitable as precursors to ureas.

4-Methyl-piperazine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-1-yl}-amide trifluoroacetate A solution of imidazole-1-carboxylic acid {(R)-1-[9-((3aS,4R,6S,6aR)-2,2-dimethyl-6-propionylamino-tetrahydro-cyclopenta[1,3]dioxol-4-yl)-6-(2,2-diphenyl-ethylamino)-9H-purin-2-yl]-pyrrolidin-3-yl}-amide (25 mg, 40 μmol) in DCM (1 ml) is added to 1-methyl piperazine (4 mg, 40 μmol) and the reaction mixture is stirred at room temperature overnight. The solvent is removed in vacuo and the crude product is treated with 1:1 TFA/water (1 ml) and stirred at room temperature for 3 hours. The resulting mixture is concentrated in vacuo and purified by mass directed preparative LC-MS eluting with acetonitrile:water:trifluoroacetic acid to afford the titled compound.

Example 78

N-((1S,2R,3S,4R)-4-{6-(2,2-Diphenyl-ethylamino)-2-[(R)-3-(3-pyridin-2-yl-ureido)-pyrrolidin-1-yl]-purin-9-yl}-2,3-dihydroxy-cyclopentyl)-propionamide trifluoroacetate This compound is prepared analogously to 4-methyl-piperazine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoro acetate (Example 77) by replacing 1-methyl piperazine with 2-amino pyridine.

Example 79

N-((1S,2R,3S,4R)-4-{6-(2,2-Diphenyl-ethylamino)-2-[(R)-3-(3-pyridin-4-yl-ureido)-pyrrolidin-1-yl]-purin-9-yl}-2,3-dihydroxy-cyclopentyl)-propionamide hydrochloride A mixture comprising N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 36) (16.6 mg, 29 μmol) and pyridin-4-yl-carbamic acid phenyl ester [prepared according to the reported procedure in the Journal of Medicinal Chemistry (2005), 48(6), 1857-1872] (6.9 mg, 32 μmol) in NMP (0.5 ml) is heated at 100° C. for 1 hour and then left to stir at room temperature overnight. Purification of the product by reverse phase column chromatography (Isolute™ C18, 0-100% acetonitrile in water—0.1% HCl) affords the titled compound. [MH+ 691].

Example 80

N-((1S,2R,3S,4R)-4-{6-amino-2-[(R)-3-(3-pyridin-3-yl-ureido)-pyrrolidin-1-yl]-purin-9-yl}-2,3-dihydroxy-cyclopentyl)-propionamide The following compound is prepared analogously to N-((1S,2R,3S,4R)-4-{6-(1-ethyl-propylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 54)

The invention claimed is:
1. A compound of formula I
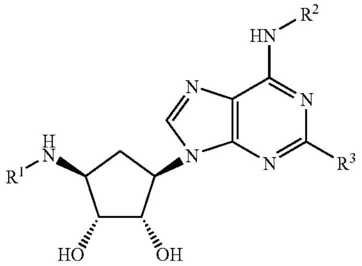
I
or a pharmaceutically acceptable salt thereof,
wherein $R^1$, $R^2$ and $R^3$ are as shown in the following table
-continued
| $R^1$ | $R^2$ |
|---|---|
| 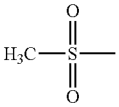 | —H |
| 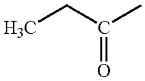 | —H |
| 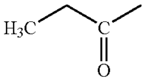 | —H |
| 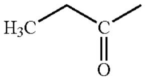 | 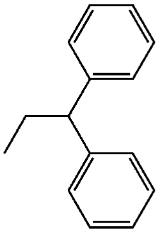 |
| 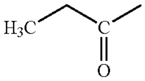 | 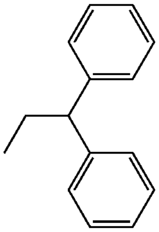 |
| 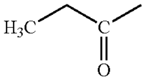 | 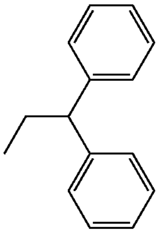 |
| 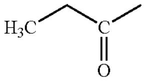 | 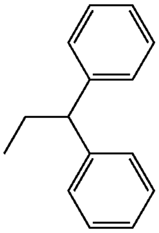 |
| 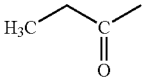 | 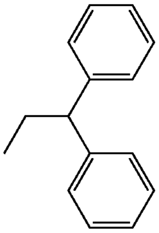 |
| 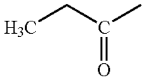 | 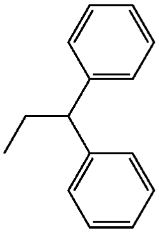 |
| 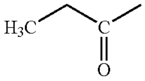 | 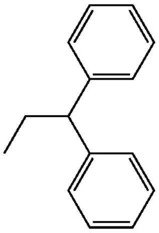 |
| 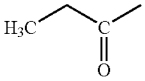 | 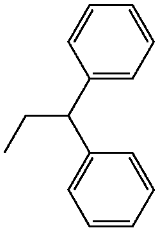 |
| 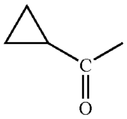 | 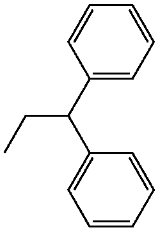 |

-continued
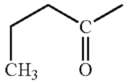 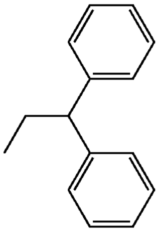
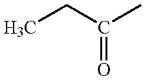 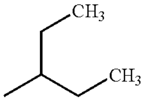
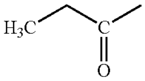 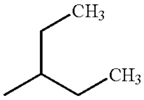
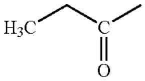 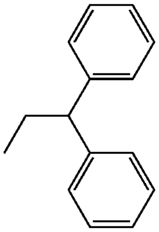
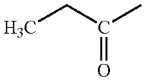 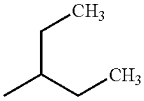
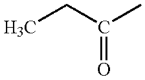 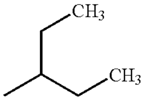
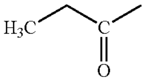 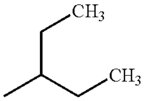
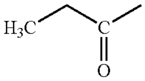 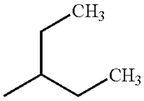
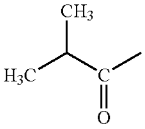 —H
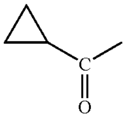 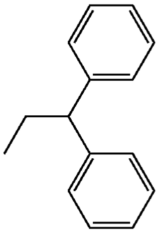
-continued
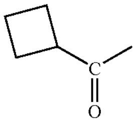 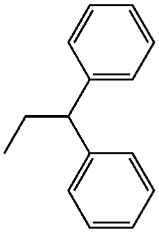
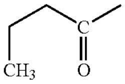 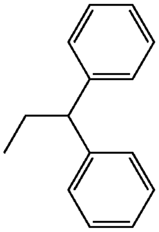
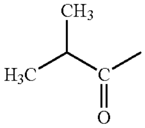 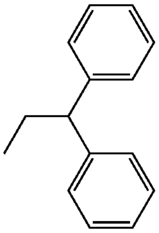
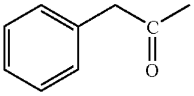 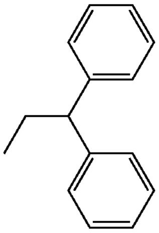
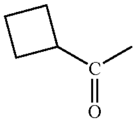 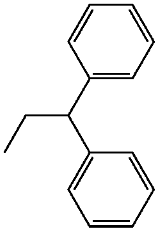
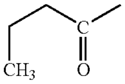 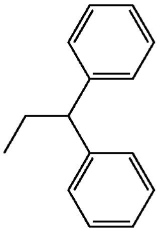

-continued
| | |
|---|---|
| 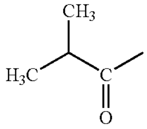 | 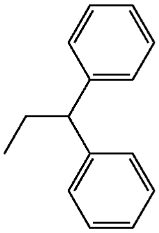 |
| 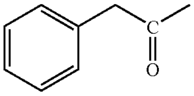 | 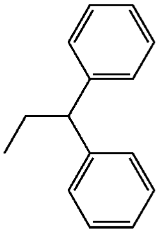 |
| 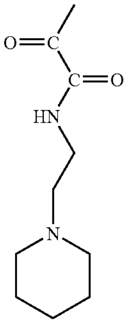 | 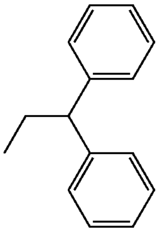 |
| 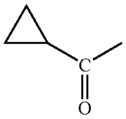 | 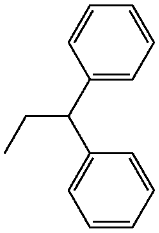 |
| 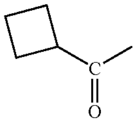 | 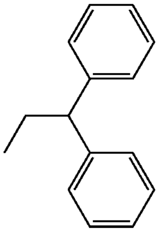 |
| 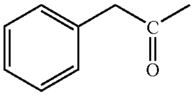 | 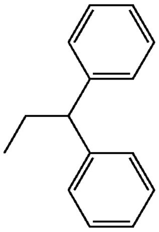 |
-continued
| | |
|---|---|
| 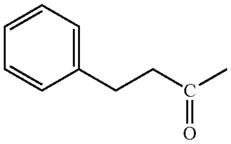 | 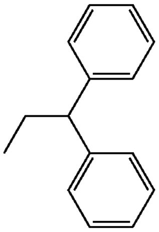 |
| 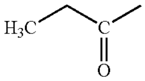 | 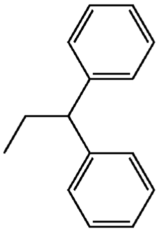 |
| 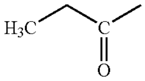 | 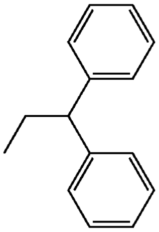 |
| 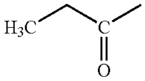 | 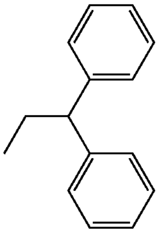 |
| 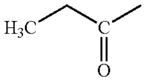 | 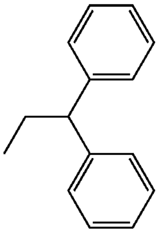 |
| 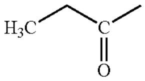 | 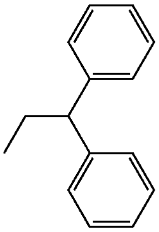 |

-continued
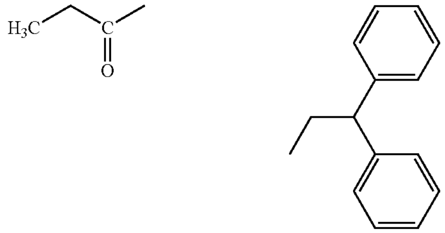
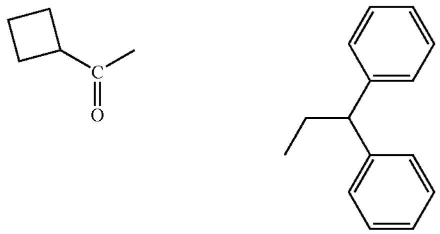
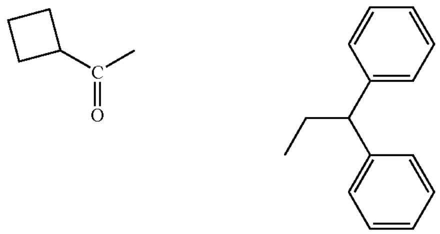
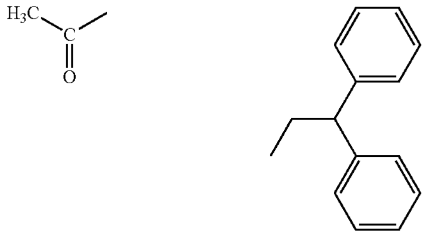
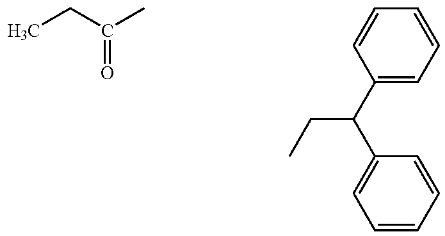
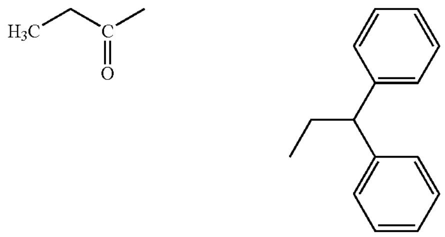
-continued
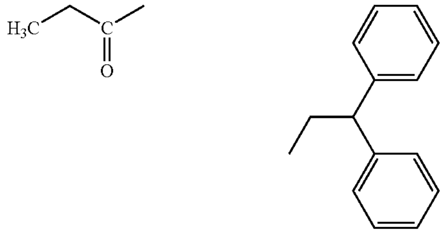
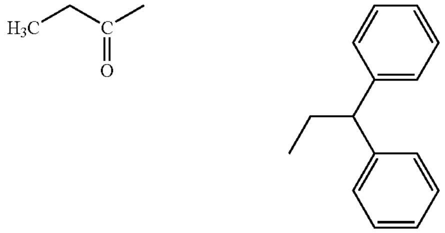
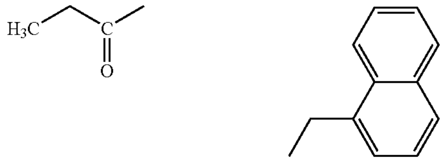
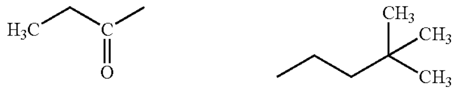
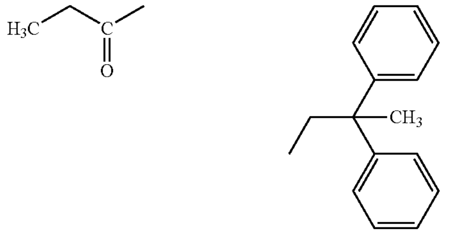
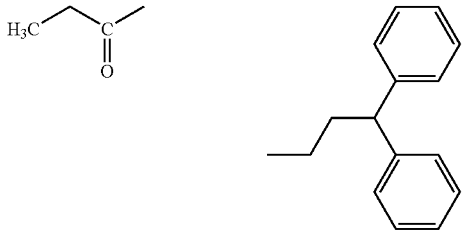
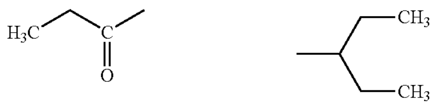
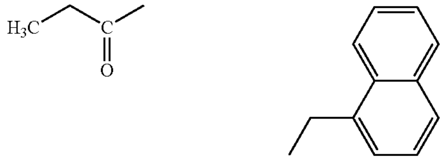
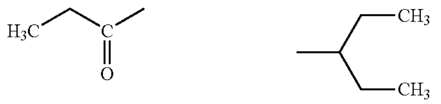

-continued
| | |
|---|---|
| 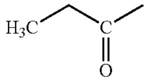 | 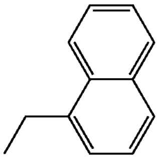 |
| 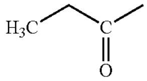 | 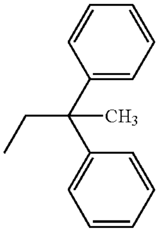 |
| 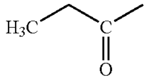 | 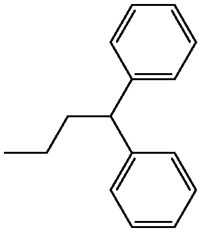 |
| 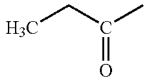 | 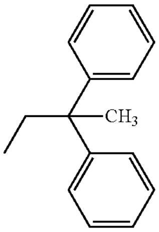 |
| 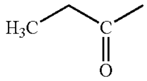 | 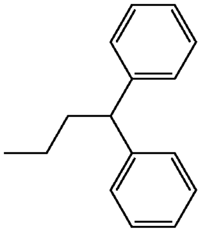 |
| 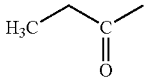 | 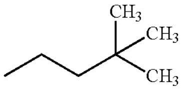 |
| 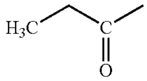 | 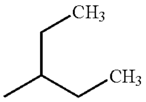 |
| 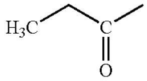 | 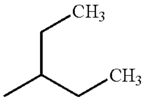 |
| 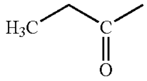 | —H |
-continued
| | |
|---|---|
| 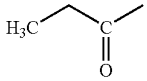 | 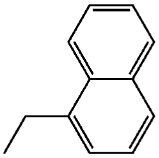 |
| 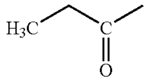 | 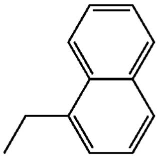 |
| 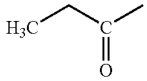 | 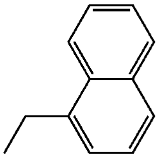 |
| 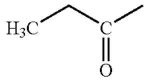 | 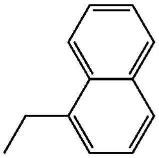 |
| 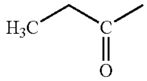 | 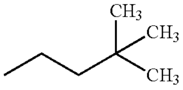 |
| 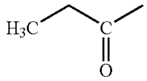 | 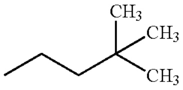 |
| 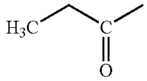 | 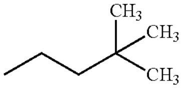 |
| 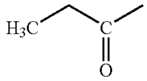 | 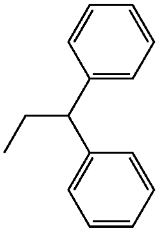 |
| 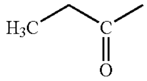 | 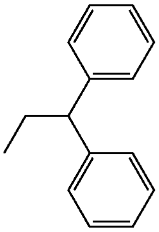 |

-continued
| | |
|---|---|
| 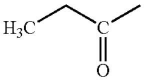 | 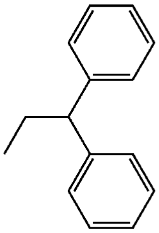 |
| 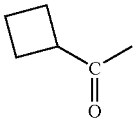 | 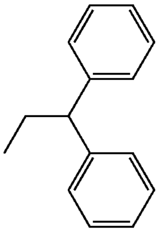 |
| 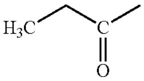 | 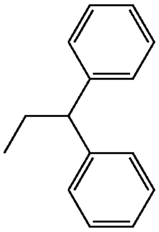 |
| 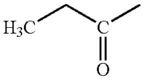 | 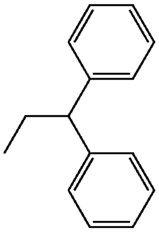 |
| 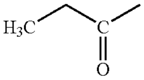 | 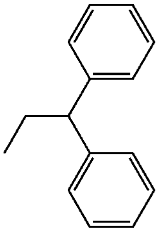 |
| 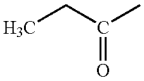 | —H |
| $R^1$ | $R^3$ |
|---|---|
| 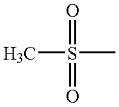 | —Cl |
| 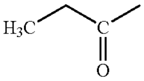 | 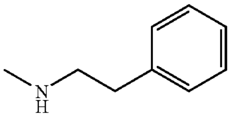 |
-continued
| | |
|---|---|
| 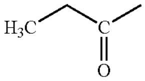 | 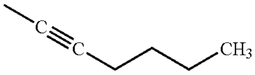 |
| 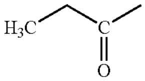 | —Cl |
| 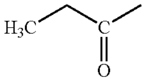 | 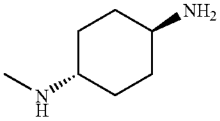 |
| 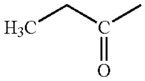 | 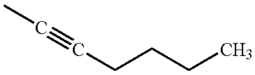 |
| 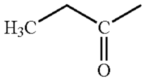 | 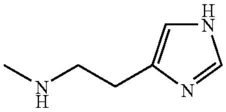 |
| 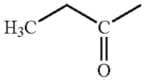 | 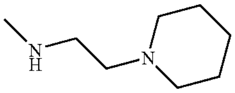 |
| 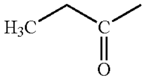 | 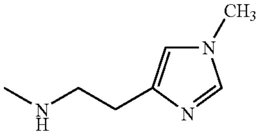 |
| 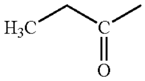 | 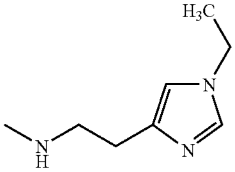 |
| 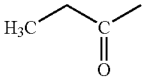 | 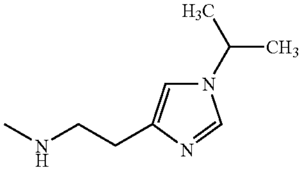 |
| 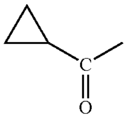 | —Cl |
| 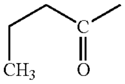 | —Cl |
| 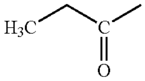 | —Cl |
| 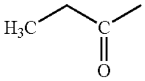 | 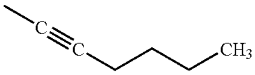 |

-continued
| | |
|---|---|
| 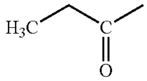 | 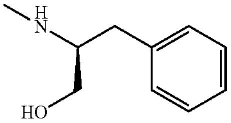 |
| 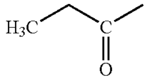 | 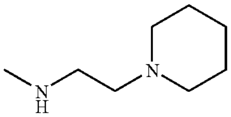 |
| 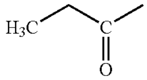 | 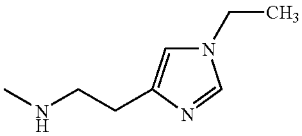 |
| 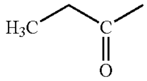 | 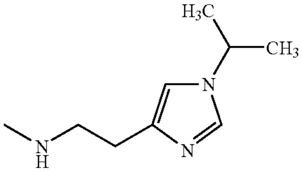 |
| 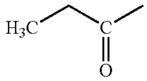 | 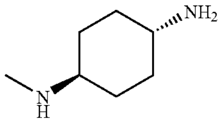 |
| 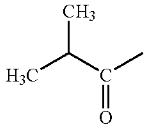 | 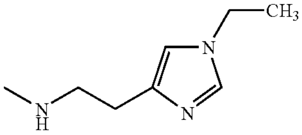 |
| 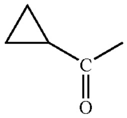 | 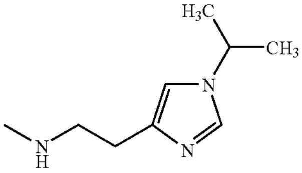 |
| 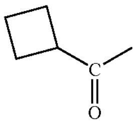 | 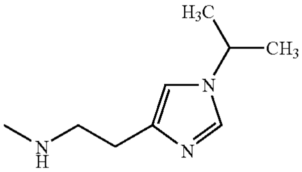 |
| 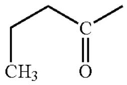 | 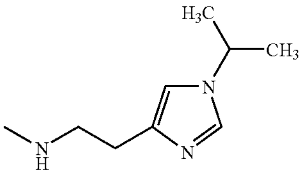 |
| 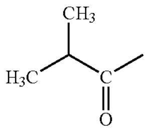 | 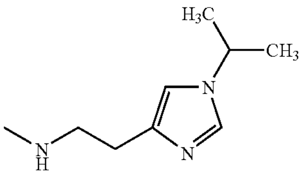 |
-continued
| | |
|---|---|
| 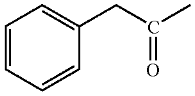 | 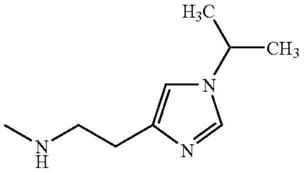 |
| 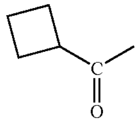 | 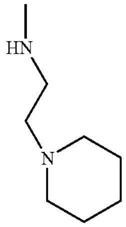 |
| 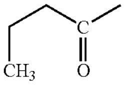 | 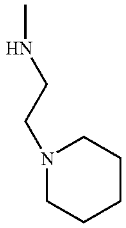 |
| 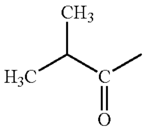 | 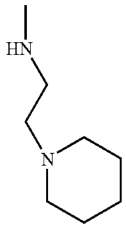 |
| 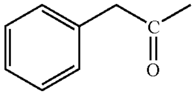 | 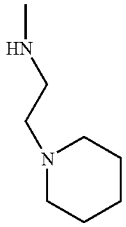 |
| 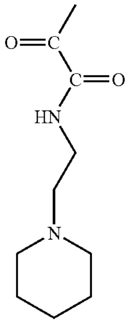 | 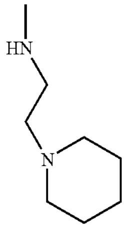 |
| 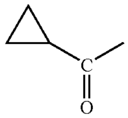 | 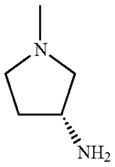 |

-continued
| | |
|---|---|
| 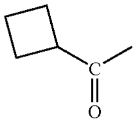 | 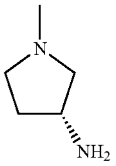 |
| 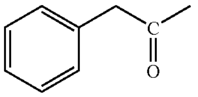 | 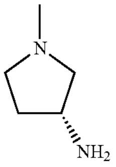 |
| 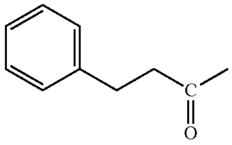 | 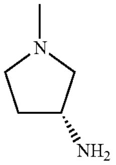 |
| 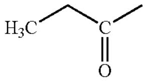 | 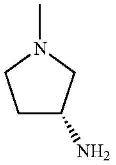 |
| 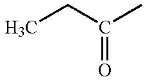 | 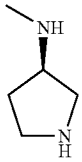 |
| 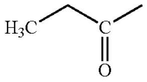 | 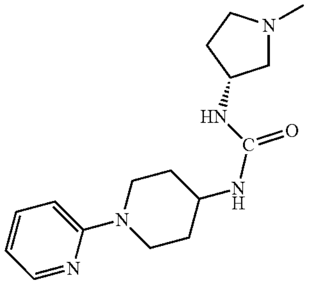 |
| 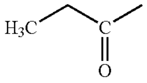 | 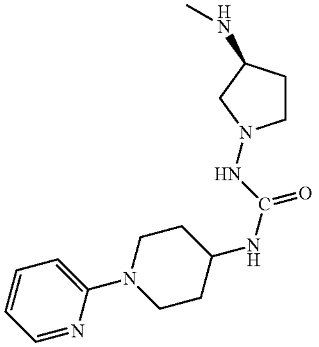 |
-continued
| | |
|---|---|
| 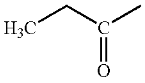 | 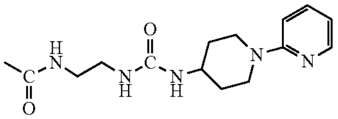 |
| 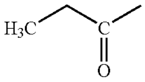 | 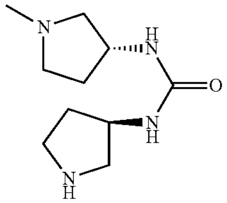 |
| 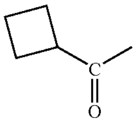 | 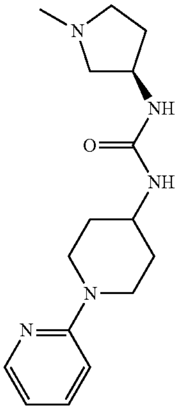 |
| 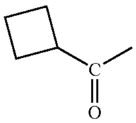 | 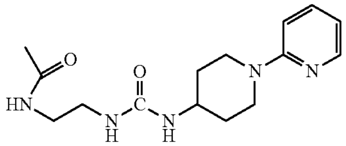 |
| 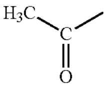 | 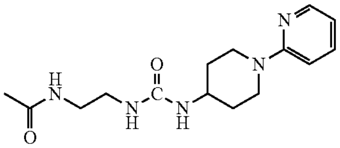 |
| 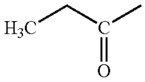 | 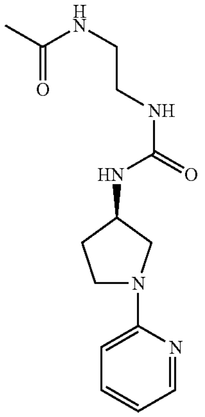 |
| 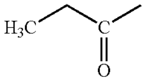 | 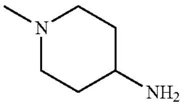 |

-continued
| | |
|---|---|
| 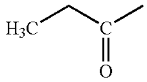 | 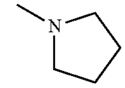 |
| 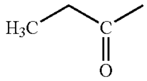 | 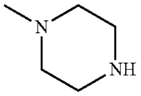 |
| 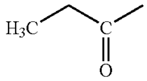 | —Cl |
| 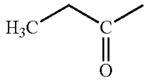 | —Cl |
| 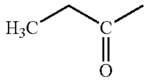 | —Cl |
| 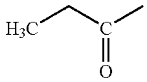 | —Cl |
| 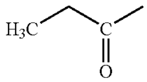 | 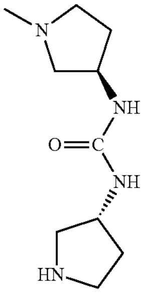 |
| 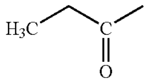 | 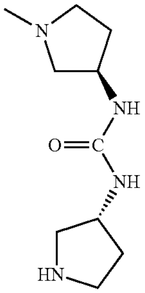 |
| 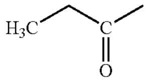 | 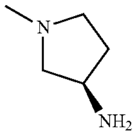 |
| 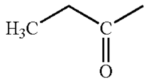 | 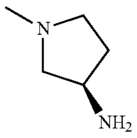 |
-continued
| | |
|---|---|
| 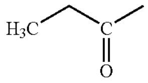 | 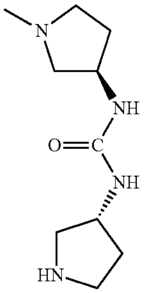 |
| 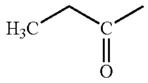 | 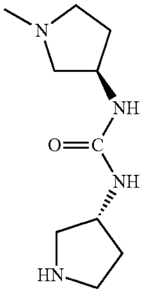 |
| 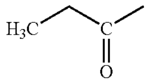 | 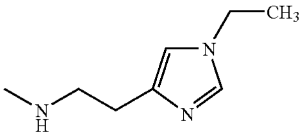 |
| 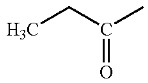 | 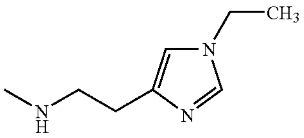 |
| 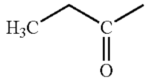 | 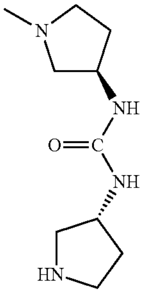 |
| 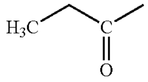 | 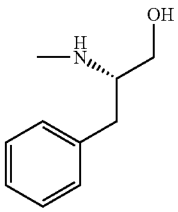 |
| 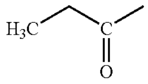 | 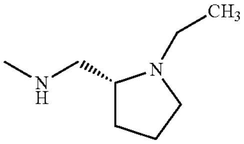 |

-continued
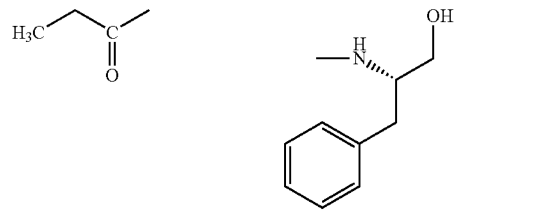
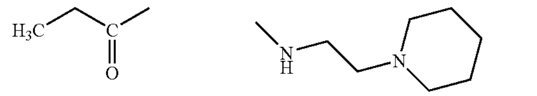
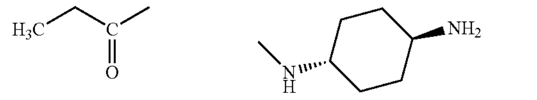
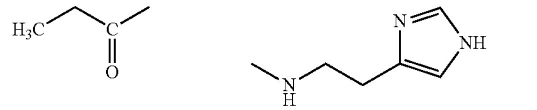
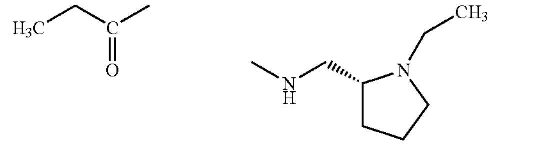
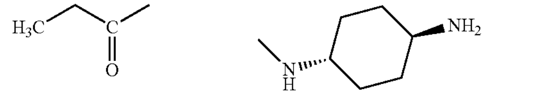
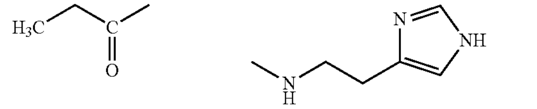
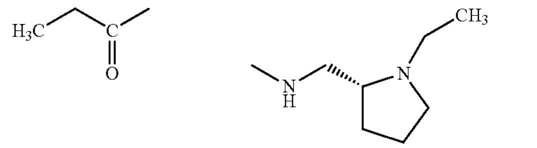
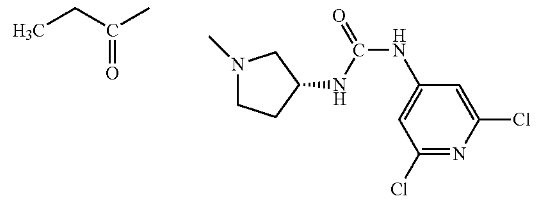
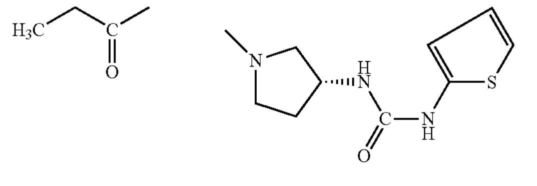
-continued
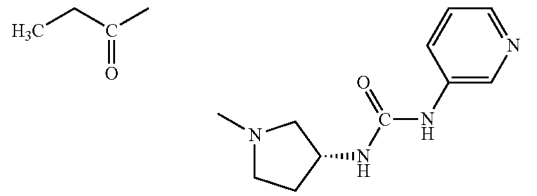
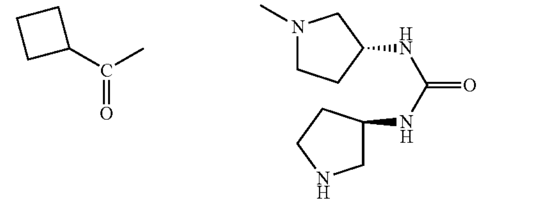
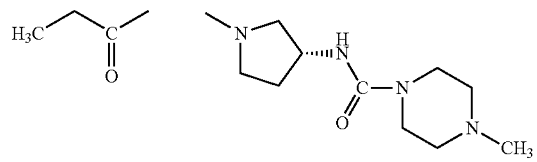
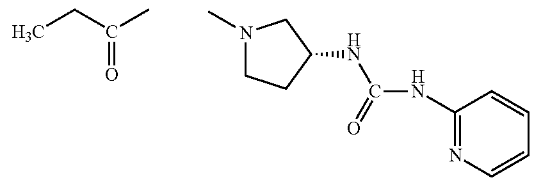
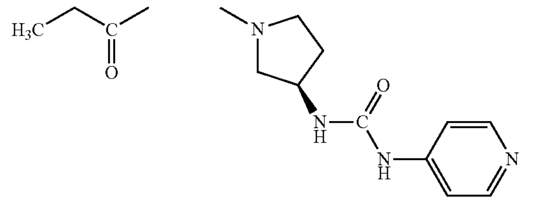
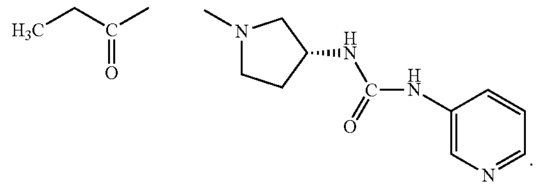
.
2. A pharmaceutical composition comprising as active ingredient a compound according to claim 1 and a pharmaceutically acceptable diluent or carrier.
3. A pharmaceutical composition according to claim 2, further comprising an anti-inflammatory, bronchodilatory, antihistamine or anti-tussive drug substance.

4. A compound of formula I

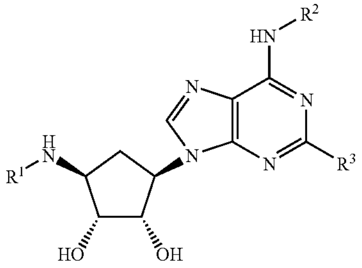

I or a pharmaceutically acceptable salt thereof, wherein $R^1$, $R^2$ and $R^3$ are as shown in the following table

| $R^1$ | $R^2$ | $R^3$ |
|---|---|---|
| 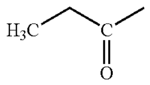 | 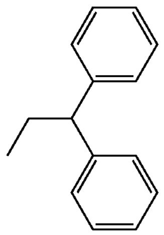 | 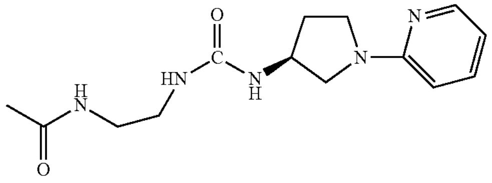 |
| 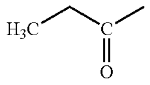 | 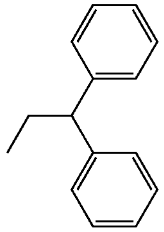 | 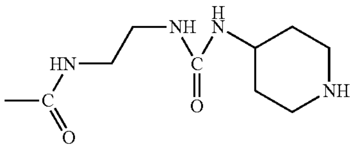 |
| 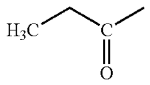 | 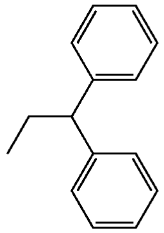 | 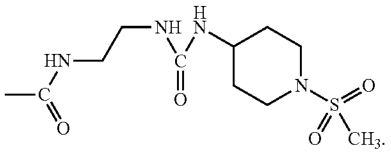 |

5. A pharmaceutical composition comprising as active ingredient a compound according to claim 4 and a pharmaceutically acceptable diluent or carrier.

6. A pharmaceutical composition according to claim 5, further comprising an anti-inflammatory, bronchodilatory, antihistamine or anti-tussive drug substance.

* * * * *